(12) United States Patent
Kitamoto et al.

(10) Patent No.: US 9,586,905 B2
(45) Date of Patent: Mar. 7, 2017

(54) BENZOAZEPINE DERIVATIVE AND MEDICAL USE THEREOF

(71) Applicant: SANWA KAGAKU KENKYUSHO CO., LTD., Nagoya-shi, Aichi (JP)

(72) Inventors: Katsunori Kitamoto, Kuwana (JP); Nobuyoshi Kasugai, Kawana (JP); Hiroyo Kataoka, Kuwana (JP); Yasushi Ohsawa, Ogaki (JP); Yuka Kuno, Kuwana (JP); Hiroki Fujieda, Kuwana (JP); Keita Sakai, Inabe (JP); Hiroki Nagano, Kuwana (JP); Naoki Takahashi, Kuwana (JP); Toru Izuchi, Kuwana (JP); Mitsuaki Takeuchi, Kuwana (JP); Daisuke Kurumazuka, Kuwana (JP); Toshiyuki Miyazawa, Kuwana (JP); Satoko Harada, Kuwana (JP); Izumi Gotoh, Kuwana (JP); Yukiyasu Asano, Hashima (JP); Yurie Yamada, Osaka (JP); Morio Okabe, Shizuoka (JP)

(73) Assignee: SANWA KAGAKU KENKYUSHO CO., LTD., Nagoya-shi (JP)

( * ) Notice: Subject to any disclaimer, the term of this patent is extended or adjusted under 35 U.S.C. 154(b) by 0 days.

(21) Appl. No.: 14/438,920

(22) PCT Filed: Dec. 26, 2013

(86) PCT No.: PCT/JP2013/084937
§ 371 (c)(1),
(2) Date: Apr. 28, 2015

(87) PCT Pub. No.: WO2014/104209
PCT Pub. Date: Jul. 3, 2014

(65) Prior Publication Data
US 2015/0291533 A1 Oct. 15, 2015

(30) Foreign Application Priority Data

Dec. 26, 2012 (JP) .................. 2012-281908

(51) Int. Cl.
*A61K 31/55* (2006.01)
*C07D 223/16* (2006.01)
(Continued)

(52) U.S. Cl.
CPC ......... *C07D 223/16* (2013.01); *C07D 403/10* (2013.01); *C07D 403/12* (2013.01);
(Continued)

(58) Field of Classification Search
CPC .... A61K 31/55; C07D 223/16; C07D 403/02; C07D 403/14; C07D 413/02; C07D 413/14
(Continued)

(56) References Cited

U.S. PATENT DOCUMENTS 4,952,573 A 8/1990 LeClerc et al.
5,258,510 A 11/1993 Ogawa et al.
(Continued)

FOREIGN PATENT DOCUMENTS

JP H04-154765 A 5/1992
JP H04-321669 A 11/1992
(Continued)

OTHER PUBLICATIONS

Lennon et al., "Azabenzocycloheptenones, Part XVII. Some Substitution Reactions in Tetrahydro-1-benzazepin-5-ones," J. Chem. Soc., Perkin Trans.I, 1974, vol. 1974, pp. 1828-1833.
(Continued)

*Primary Examiner* — Brenda Coleman
(74) *Attorney, Agent, or Firm* — Oliff PLC

(57) ABSTRACT

A compound having a V2 receptor agonistic activity is provided. Providing a pharmaceutical composition which contains, as an active ingredient, a compound represented by general formula (I) described below:

[Formula 1]

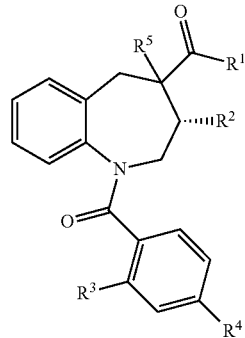

(I)

[$R^1$ is formula described below:

[Formula 2]

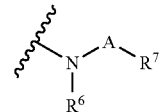

(A is a lower alkylene group which may be substituted with lower alkyl group; $R^6$ is a hydrogen atom; $R^7$ is a hydroxyl group, an aromatic heterocyclic group which may be substituted with lower alkyl group, carbamoyl group); $R^2$ is a hydrogen atom or lower alkyl group; $R^3$ is lower alkyl group which may be substituted with 1-3 fluorine atoms, or halo- (Continued)

gen atom; $R^4$ is a five-membered aromatic monocyclic heterocyclic group, five-membered non-aromatic monocyclic heterocyclic group, (provided each heterocyclic groups contain at least one nitrogen atom and may be substituted with a lower alkyl group); and $R^5$ is a lower alkyl group, halogen atom], or pharmacologically acceptable salt thereof.

14 Claims, No Drawings

(51) Int. Cl.
| | | |
|---|---|---|
| C07D 403/02 | (2006.01) | |
| C07D 403/14 | (2006.01) | |
| C07D 413/02 | (2006.01) | |
| C07D 413/14 | (2006.01) | |
| C07D 403/10 | (2006.01) | |
| C07D 413/10 | (2006.01) | |
| C07D 403/12 | (2006.01) | |
| C07D 413/12 | (2006.01) | |

(52) U.S. Cl.
CPC ......... *C07D 403/14* (2013.01); *C07D 413/10* (2013.01); *C07D 413/12* (2013.01); *C07D 413/14* (2013.01)

(58) Field of Classification Search
USPC ..................................... 514/213.01; 540/593
See application file for complete search history.

(56) References Cited

U.S. PATENT DOCUMENTS

| | | |
|---|---|---|
| 5,559,230 A | 9/1996 | Ogawa et al. |
| 5,753,677 A | 5/1998 | Ogawa et al. |
| 5,985,869 A | 11/1999 | Ogawa et al. |
| 6,096,736 A | 8/2000 | Ogawa et al. |
| 2008/0076754 A1 | 3/2008 | Xiang et al. |
| 2008/0161294 A1 | 7/2008 | Suzuki et al. |

FOREIGN PATENT DOCUMENTS

| | | |
|---|---|---|
| JP | H09-221476 A | 8/1997 |
| JP | H10-81668 A | 3/1998 |
| JP | H11-1456 A | 1/1999 |
| JP | H11-60488 A | 3/1999 |
| JP | 2000-351768 A | 12/2000 |
| JP | 2004-323372 A | 11/2004 |
| JP | 2010-504352 A | 2/2010 |
| WO | 95/34540 A1 | 12/1995 |
| WO | 97/22591 A1 | 6/1997 |
| WO | 2005/037795 A2 | 4/2005 |
| WO | 2006/104008 A1 | 10/2006 |

OTHER PUBLICATIONS

Apr. 8, 2014 International Search Report issued in International Application No. PCT/JP2013/084937.

BENZOAZEPINE DERIVATIVE AND MEDICAL USE THEREOF

TECHNICAL FIELD

The present invention relates to a useful novel benzoazepine derivative as a medical product and a medical use thereof. The compound has various medical uses as a V2 receptor agonist.

BACKGROUND ART

Arginine vasopressin is synthesized in the hypothalamic area and is a peptide composed of 9 amino acids, which is excreted from the posterior pituitary. Receptors of arginine vasopressin are classified into three kinds of subtypes of V1a, V1b, and V2, a V1a receptor exists in the liver, muscular tissue vascular cells, blood platelets, peripheral tissues, and central nerve system, a V1b receptor exists in the central nerve system, and a V2 receptor exists in the kidney collecting tubule cells. When arginine vasopressin is connected to a V2 receptor, reabsorption of water is promoted in the kidney collecting tubule and a urinary volume is decreased. Therefore, when arginine vasopressin is in short, polyuria is caused, and examples of diseases due to polyuria include central diabetes insipidus, childhood nocturnal enuresis, nocturia, and overactive bladder. Accordingly, a V2 receptor agonist is useful as a preventive or therapeutic agent of these diseases. In addition, a V2 receptor agonist has release actions of a blood VIII factor and a Von Willebrand factor and can thus treat hemorrhagic diseases (such as hemophilia and Von Willebrand disease).

Conventionally, desmopressin that is a peptide (arginine vasopressin in which an amino group of the 1st cysteine is deleted and the 8th arginine is converted into d type) has been used for treatments of central diabetes insipidus and nocturnal enuresis as a V2 receptor agonist. However, an oral agent of desmopressin is very low in a biological availability and a high dosage is required in order to attain its effects. Furthermore, a preparation of desmopressin is expensive, also, there is a concern about occurrence of side effects caused by fluctuation of absorption among individuals, and a preparation of desmopressin is not necessarily satisfied in view of safety. Accordingly, creation of a medical drug having a high biological availability and less fluctuation of absorption has been desired.

On the other hand, a metabolic reaction due to cytochrome P-450 (CYP) plays a dominant role in disappearance of a drug from a body, and when a drug metabolized by CYP having the same molecular species competes against each other in the metabolic enzyme, some sort of metabolic inhibition is assumed to be caused. Inhibition of CYP may lead to variation in a blood concentration and a tissue concentration of a drug, change in treatment effects, and occurrence of serious side effects. Therefore, creation of a medical drug having low affinity to CYP and less concern about enzymatic inhibition has been desired.

So far, benzoheterocyclic derivatives (Patent Literatures 1 to 3), benzoazepine derivatives (Patent Literatures 4 and 5), an amide derivative (Patent Literature 6), a benzodiazepine derivative (Patent Literature 7) have been reported as a compound having a vasopressin receptor agonistic action, and a substituted spiro benzoazepine derivative (Patent Literature 8) has been reported as a compound having a vasopressin receptor antagonistic action; however, these compounds are different from the compound of the present application in the structure having a carbonyl group on the 4th carbon of benzoazepine.

PRIOR ART DOCUMENTS

Patent Literatures

Patent Literature 1: WO No. 95/34540
Patent Literature 2: JP-A No. 09-221476
Patent Literature 3: JP-A No. 2000-351768
Patent Literature 4: WO No. 97/22591
Patent Literature 5: JP-A No. 11-60488
Patent Literature 6: JP-A No. 11-1456
Patent Literature 7: WO No. 2006/104008
Patent Literature 8: WO No. 2005/37795

SUMMARY OF THE INVENTION

Problems to be Solved by the Invention

Objects of the present invention are to provide a compound having a V2 receptor agonistic action and to provide a preventive or therapeutic agent for central diabetes insipidus, nocturnal enuresis, nocturia, overactive bladder, hemophilia, or Von Willebrand disease based on the V2 receptor agonistic action.

Solutions to the Problems

For the present invention, in view of the above described points, a compound having a novel basic structure was considered to be effective as means for solving the above described problems, and intensive investigations have been repeated for the purpose of creation of a novel V2 receptor agonist. As a result, it was found that a compound represented by the general formula (I) described below and a salt thereof have excellent V2 receptor agonistic actions and completion of the present invention was thus attained.

That is, according to the present invention, provided is a compound represented by the general formula (I):

[Formula 1]

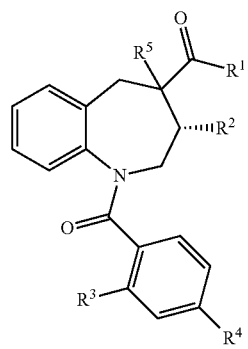

(I)

[wherein $R^1$ is a hydroxyl group, a lower alkoxy group, or the formula described below:

[Formula 2]

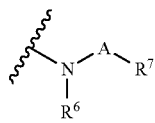

(wherein A is absent or is a lower alkylene group which may be substituted with a lower alkyl group; $R^6$ is a hydrogen atom or a lower alkyl group; $R^7$ is a hydrogen atom, a hydroxyl group, an aromatic heterocyclic group which may be substituted with a lower alkyl group, a non-aromatic heterocyclic group which may be substituted with an oxo group, or a carbamoyl group which may be substituted with a lower alkyl group); $R^2$ is a hydrogen atom or a lower alkyl group; $R^3$ is a lower alkyl group which may be substituted with 1 to 3 fluorine atoms, or a halogen atom; $R^4$ is a lower alkoxy group which may be substituted with a halogen atom, a five-membered aromatic monocyclic heterocyclic group, or a five-membered non-aromatic monocyclic heterocyclic group (provided that each of these heterocyclic groups contains at least one nitrogen atom and may be substituted with a lower alkyl group); and $R^5$ is a hydrogen atom, a lower alkyl group, or a halogen atom], or a pharmacologically acceptable salt thereof; and the compound is called "the compound of the present invention". Various embodiments of the compound of the present invention will be listed below.

One embodiment of the present invention is a compound, wherein, in the above described general formula (I), $R^1$ is a hydroxyl group, a lower alkoxy group, or the formula described below:

[Formula 3]

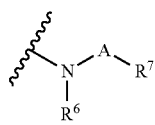

[wherein A is absent or is a lower alkylene group which may be substituted with a lower alkyl group; $R^6$ is a hydrogen atom or a lower alkyl group; $R^7$ is a hydrogen atom, a hydroxyl group, an aromatic heterocyclic group which may be substituted with a lower alkyl group, a non-aromatic heterocyclic group which may be substituted with an oxo group, or a carbamoyl group which may be substituted with a lower alkyl group, provided that the case in which A is a lower alkylene group which may be substituted with a lower alkyl group and both $R^6$ and $R^7$ are hydrogen atoms, and the case in which A is absent, $R^6$ is a lower alkyl group, and $R^7$ is a hydrogen atom, are excluded].

Another embodiment of the present invention is a compound, wherein, in the above described general formula (I), $R^1$ is the formula described below:

[Formula 4]

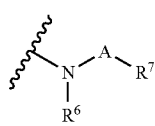

[wherein A is absent or is a lower alkylene group which may be substituted with a lower alkyl group; $R^6$ is a hydrogen atom or a lower alkyl group; $R^7$ is a hydrogen atom, a hydroxyl group, an oxadiazole group which may be substituted with a lower alkyl group, a pyrrolidine group which may be substituted with an oxo group, or a carbamoyl group which may be substituted with 1 or 2 lower alkyl groups, provided that the case in which A is a lower alkylene group which may be substituted with a lower alkyl group and both $R^6$ and $R^7$ are hydrogen atoms, and the case in which A is absent, $R^6$ is a lower alkyl group, and $R^7$ is a hydrogen atom, are excluded].

Another embodiment of the present invention is a compound, wherein, in the above described general formula (I), $R^1$ is the formula described below:

[Formula 5]

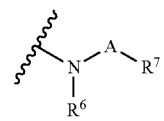

[wherein A is a lower alkylene group which may be substituted with a lower alkyl group; $R^6$ is a hydrogen atom; $R^7$ is a hydroxyl group, an oxadiazole group which may be substituted with a lower alkyl group, or a carbamoyl group].

Another embodiment of the present invention is a compound, wherein, in the above described general formula (I), $R^4$ is a lower alkoxy group which may be substituted with 1 to 3 fluorine atoms, a pyrrolidine group which may be substituted with 1 to 4 lower alkyl groups, a pyrazole group which may be substituted with 1 to 3 lower alkyl groups, or an oxazolyl group which may be substituted with 1 or 2 lower alkyl groups.

Another embodiment of the present invention is a compound, wherein, in the above described general formula (I), $R^4$ is a group selected from the following group:

[Formula 6]

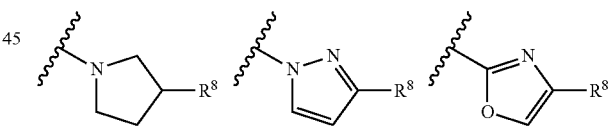

[wherein $R^8$ is a hydrogen atom or a lower alkyl group].

Another embodiment of the present invention is a compound, wherein, in the above described general formula (I), $R^4$ is a group selected from the following group:

[Formula 7]

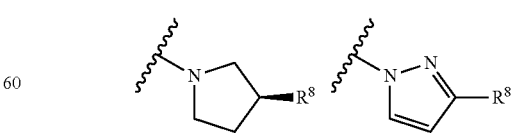

[wherein $R^8$ is a lower alkyl group.]

Another embodiment of the present invention is a compound, wherein $R^5$ is a methyl group or a fluorine atom in the above described general formula (I).

Another embodiment of the present invention is a compound, wherein $R^3$ is a methyl group, a trifluoromethyl group, or a chlorine atom in the above described general formula (I).

Another embodiment of the present invention is a compound, wherein, in the above described general formula (I), $R^1$ is the formula described below:

[Formula 8]

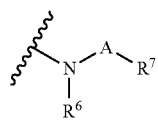

[wherein A is a lower alkylene group which may be substituted with a lower alkyl group; $R^6$ is a hydrogen atom; $R^7$ is a hydroxyl group, an oxadiazole group which may be substituted with a lower alkyl group, or a carbamoyl group], $R^2$ is a hydrogen atom, $R^3$ is a methyl group, a trifluoromethyl group, or a chlorine atom, $R^4$ is a group selected from the following group:

[Formula 9]

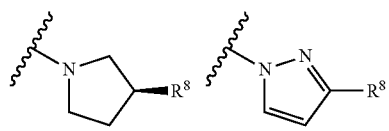

[wherein $R^8$ is a lower alkyl group], and $R^5$ is a methyl group or a fluorine atom.

The present invention also provides a compound represented by the general formula (II), which is an intermediate of the compound of the present invention represented by the above described general formula (I):

[Formula 10]

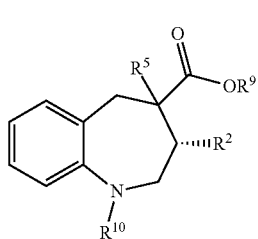

[wherein $R^2$ is a hydrogen atom or a lower alkyl group; $R^5$ is a hydrogen atom, a methyl group, an ethyl group, or a halogen atom; $R^9$ is a hydrogen atom or a protecting group of a carboxy group; and $R^{10}$ is a hydrogen atom or a protecting group of an amino group, provided that the case in which both $R^2$ and $R^5$ are hydrogen atoms is excluded].

The present invention also provides a pharmaceutical composition containing the compound of the present invention as an active ingredient. That is, the pharmaceutical composition of the present invention is used for prevention or treatment of disease selected from the group consisting of central diabetes insipidus, nocturnal enuresis, nocturia, overactive bladder, hemophilia, and Von Willebrand disease.

Effects of the Invention

The compound of the present invention has an excellent V2 receptor agonistic action, and is useful as a preventive or therapeutic agent for a disease selected from the group consisting of central diabetes insipidus, nocturnal enuresis, nocturia, overactive bladder, hemophilia, and Von Willebrand disease. Note that the main compound of the present invention selectively acts on a V2 receptor, and has a low inhibition activity to drug metabolizing enzymes CYP3A4 and CYP2C9, as compared to conventionally known compounds having a V2 receptor agonistic action, and what is more, also in view of physical properties as a medical product such as solubility and membrane permeability and in view of kinetics such as plasma clearance and distribution volume, has excellent properties and therefore, the present invention is a safe and useful medical drug which is excellent in dissociation of various side effects (cytotoxicity, actions to hERG and CYP) and medicinal benefits.

EMBODIMENTS OF THE INVENTION

Hereinbelow, the compound of the present invention will be explained.

[Formula 11]

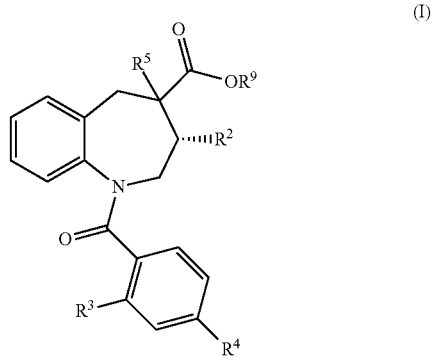

The compound of the present invention is a compound wherein $R^1$, $R^2$, $R^3$, $R^4$, and $R^5$ are defined as described below in the compound expressed by the above described general formula (I), or a pharmacologically acceptable salt thereof.

$R^1$ is a hydroxyl group, a lower alkoxy group, or the formula described below:

[Formula 12]

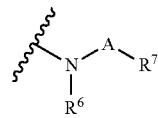

[wherein A is absent or is a lower alkylene group which may be substituted with a lower alkyl group; $R^6$ is a hydrogen atom or a lower alkyl group; $R^7$ is a hydrogen atom, a hydroxyl group, an aromatic heterocyclic group which may be substituted with a lower alkyl group, a non-aromatic heterocyclic group which may be substituted with an oxo group, or a carbamoyl group which may be substituted with a lower alkyl group]; among them, $R^1$ is preferably a hydroxyl group, a lower alkoxy group, or the formula described below:

[Formula 13]

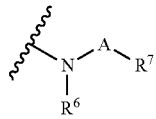

[wherein A is absent or is a lower alkylene group which may be substituted with a lower alkyl group; $R^6$ is a hydrogen atom or a lower alkyl group; $R^7$ is a hydrogen atom, a hydroxyl group, an aromatic heterocyclic group which may be substituted with a lower alkyl group, a non-aromatic heterocyclic group which may be substituted with an oxo group, or a carbamoyl group which may be substituted with a lower alkyl group, provided that the case in which A is a lower alkylene group which may be substituted with a lower alkyl group and both $R^6$ and $R^7$ are hydrogen atoms, and the case in which A is absent, $R^6$ is a lower alkyl group, and $R^7$ is a hydrogen atom, are excluded]; and among them, $R^1$ is particularly preferably the formula described below:

[Formula 14]

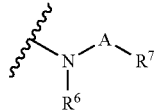

[wherein A is absent or is a lower alkylene group which may be substituted with a lower alkyl group; $R^6$ is a hydrogen atom or a lower alkyl group; $R^7$ is a hydrogen atom, a hydroxyl group, an oxadiazole group which may be substituted with a lower alkyl group, a pyrrolidine group which may be substituted with an oxo group, or a carbamoyl group which may be substituted with 1 or 2 lower alkyl groups, provided that the case in which A is a lower alkylene group which may be substituted with a lower alkyl group and both $R^6$ and $R^7$ are hydrogen atoms, and the case in which A is absent, $R^6$ is a lower alkyl group, and $R^7$ is a hydrogen atom, are excluded]; and among them, A is preferably a lower alkylene group which may be substituted with a lower alkyl group, $R^6$ is preferably a hydrogen atom, and $R^7$ is preferably a hydroxyl group, an oxadiazole group which may be substituted with a lower alkyl group, or a carbamoyl group.

$R^2$ is a hydrogen atom or a lower alkyl group, and is preferably a hydrogen atom. $R^3$ is a lower alkyl group which may be substituted with 1 to 3 fluorine atoms, or a halogen atom, and is preferably a methyl group, a trifluoromethyl group, or a chlorine atom among them.

$R^4$ is a lower alkoxy group which may be substituted with a halogen atom, a five-membered aromatic monocyclic heterocyclic group, or a five-membered non-aromatic monocyclic heterocyclic group (provided that each of these heterocyclic groups contains at least one nitrogen atom and may be substituted with a lower alkyl group). Among them, $R^4$ is preferably a group selected from the following group:

[Formula 15]

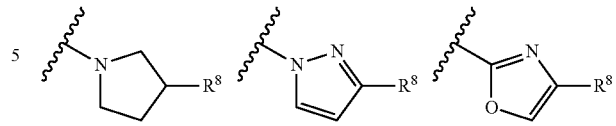

[wherein $R^8$ is a hydrogen atom or a lower alkyl group]; and among them, $R^4$ is particularly preferably a group selected from the following group:

[Formula 16]

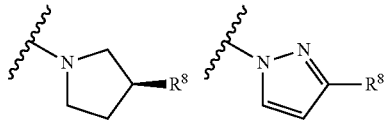

[wherein $R^8$ is a lower alkyl group].

$R^5$ is a hydrogen atom, a lower alkyl group, or a halogen atom and, among them, $R^5$ is preferably a methyl group or a fluorine atom.

A particularly preferable compound of the present invention is a compound in which, in the general formula (I), $R^1$ is the formula described below:

[Formula 17]

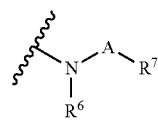

[wherein A is a lower alkylene group which may be substituted with a lower alkyl group, $R^6$ is a hydrogen atom, $R^7$ is a hydroxyl group, an oxadiazole group which may be substituted with a lower alkyl group, or a carbamoyl group], $R^2$ is a hydrogen atom, $R^3$ is a methyl group, a trifluoromethyl group, or a chlorine atom, $R^4$ is a group selected from the following group:

[Formula 18]

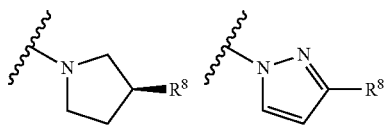

[wherein $R^8$ is a lower alkyl group], and $R^5$ is a methyl group or a fluorine atom.

In addition, the description uses definitions as described below.

A "lower alkoxy group" means a —O—(C1 to C3 alkyl) group, and examples thereof include a methoxy group, an ethoxy group, an n-propoxy group, and an i-propoxy group.

A "lower alkyl group" means a linear alkyl group having 1 to 3 carbon atoms, and examples thereof include a methyl group, an ethyl group, and an n-propyl group.

A "lower alkylene group" means a linear alkylene group having 1 to 3 carbon atoms, and examples thereof include a methylene group, an ethylene group, and an n-propylene group.

An "aromatic heterocyclic group" means a monocyclic to tricyclic aromatic ring group which contains at least one hetero atom such as nitrogen, oxygen and sulfur, and examples thereof include a pyridyl group, a thienyl group, a furyl group, a pyrazinyl group, a pyridazinyl group, a thiazolyl group, a pyrimidinyl group, a pyrazolyl group, a pyrrolyl group, an oxazolyl group, an oxadiazolyl group, an isothiazolyl group, an isoxazolyl group, an imidazolyl group, a quinoline group, a quinazoline group, a purine group, and an acridine group.

A "non-aromatic heterocyclic group" means a 3 to 10-membered non-aromatic ring group which may partially have unsaturated bonds and contains at least one hetero atom such as nitrogen, oxygen and sulfur, and examples thereof include a pyrrolidinyl group, a piperidinyl group, an azepinyl group, a morpholinyl group, a thiomorpholinyl group, a piperazinyl group, a pyrazolidinyl group, a piperazinyl group, an indolyl group, a 1,2-dihydroisoquinolyl group, and a 1,2,3,4-tetrahydroquinoxalinyl group.

A "halogen atom" means a fluorine atom, a chlorine atom, a bromine atom, or an iodine atom.

A "5-membered aromatic or non-aromatic monocyclic heterocyclic group" means a monocyclic group which may have an unsaturated bond and contains at least one hetero atom such as nitrogen, oxygen and sulfur, and examples thereof include a pyrrolidinyl group, a thienyl group, a furyl group, a pyrazolyl group, an oxazolyl group, an oxadiazolyl group, and an imidazolyl group.

A "pharmacologically acceptable salt" means a salt that has biological effectiveness and characteristics of a compound expressed by the general formula (I) and is not disadvantageous also in biological and other aspects. Such a pharmacologically acceptable salt is included in the scope of the present invention. Examples of the pharmacologically acceptable salt include salts with amino acids (for example, salts with lysine, arginine, and the like), alkali metal addition salts (for example, salts with sodium, potassium, and the like), alkali earth metal addition salts (for example, salts with calcium, magnesium, and the like), organic amine addition salts (for example, salts with diethylamine, diethanolamine, piperazine, and the like), inorganic acid addition salts (for example, salts with hydrochloric acid, hydrobromic acid, sulfuric acid, nitric acid, and the like), and organic acid addition salts (for example, salts with formic acid, acetic acid, trifluoroacetic acid, and the like). A formation reaction of these addition salts can be carried out according to a general method.

In the case of converting into the above described general formula (I) by a reaction due to an enzyme, gastric acid, or the like, under physiological conditions in a living body, these compounds are included in the scope of the present invention. Examples thereof include, when $R^1$ in a compound expressed by the general formula (I) forms a carboxy group with a hydroxyl group, compounds in which the carboxy group is subjected to esterification (for example, ethyl esterification, carboxymethyl esterification, and pivaloyloxymethylation) or amidation (for example, methylamidation). In addition, when a group expressed by $R^1$ has a hydroxyl group, examples thereof include compounds in which the hydroxyl group is subjected to acylation (for example, acetylation, propionylation and t-butylcarbonylation), alkoxycarbonylation (for example, methoxycarbonylation, ethoxycarbonylation and t-butoxycarbonylation), or succinylation.

Next, a compound that is an intermediate of the compound of the present invention will be explained.

[Formula 19]

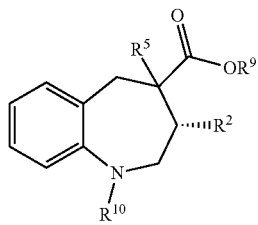

(II)

An intermediate compound of the compound of the present invention is a compound expressed by the above described general formula (II) wherein $R^2$ is a hydrogen atom or a lower alkyl group, $R^5$ is a hydrogen atom, a methyl group, an ethyl group, or a halogen atom, $R^9$ is a hydrogen atom or a protecting group of a carboxy group, and $R^{10}$ is a hydrogen atom or a protecting group of an amino group (provided that the case in which both of $R^2$ and $R^5$ are hydrogen atoms is excluded).

Herein, "a protecting group of a carboxy group" means a group generally known as a protecting group of a carboxy group inorganic synthesis, and examples thereof include (1) a linear or branched lower alkyl group having 1 to 4 carbon atoms (for example, methyl group, ethyl group, i-propyl group, and t-butyl group), (2) a halogeno lower alkyl group (for example, 2-ethyl iodide group and 2,2,2-trichloroethyl group), (3) a lower alkoxymethyl group (for example, methoxymethyl group, ethoxymethyl group, and i-butoxymethyl group), (4) a lower aliphatic acyloxymethyl group (for example, butyryloxymethyl group and pivaloyloxymethyl group), (5) a 1-lower alkoxycarbonyloxyethyl group (for example, 1-methoxycarbonyloxyethyl group and 1-ethoxycarbonyloxyethyl group), (6) an aralkyl group (for example, benzyl, p-methoxybenzyl group, o-nitrobenzyl group, and p-nitrobenzyl group), (7) a benzhydryl group, and (8) a phthalidyl group.

In addition, "a protecting group of an amino group" means a group generally known as a protecting group of an amino group in organic synthesis, and examples thereof include (1) a substituted or unsubstituted lower alkanoyl group (for example, formyl group, acetyl group, chloroacetyl group, dichloroacetyl group, propionyl group, phenyl acetyl group, phenoxyacetyl group, and thienylacetyl group), (2) a substituted or unsubstituted lower alkoxycarbonyl group (for example, benzyloxycarbonyl group, t-butoxycarbonyl group, p-nitrobenzyloxycarbonyl group, and 9-fluorenylmethyloxycarbonyl group), (3) a substituted or unsubstituted lower alkyl group (for example, methyl group, t-butyl group, 2,2,2-trichloroethyl group, trityl group, p-methoxybenzyl group, p-nitrobenzyl group, diphenylmethyl group, and pivaloyloxymethyl group), (4) a substituted silyl group (for example, trimethylsilyl group and t-butyldimethylsilyl group), and (5) a substituted or unsubstituted benzylidene group (for example, benzylidene group, salicylidene group, p-nitrobenzylidene group, m-chlorbenzylidene group, 3,5-di(t-butyl)-4-hydroxybenzylidene group, and 3,5-di(t-butyl)benzylidene group).

When one or more asymmetric carbons are present in the compound of the present invention, the invention includes any compound of isomer based on the asymmetric carbons and any combination thereof. In addition, when geometric isomerism or tautomerism is present in the compound of the invention, the invention includes any geometric isomer or tautomer thereof. Furthermore, the compound of the present invention also includes a solvate with a solvent which is acceptable as a medical product, such as water, ethanol and isopropanol.

The compound represented by the general formula (I), which is the compound of the present invention, can be manufactured by a method shown in the reaction step formula I described below, a method described in examples, or a method of combining known methods:

[Reaction Step Formula I]

[Formula 20]

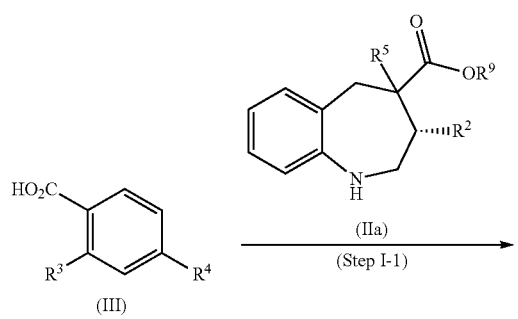

(III)

(IIa)

(Step I-1)

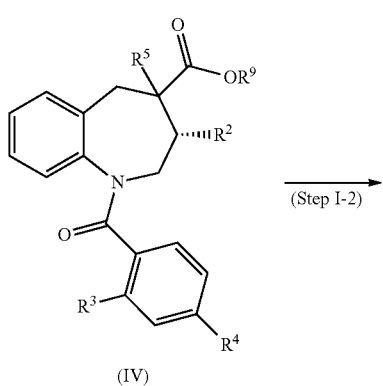

(IV)

(Step I-2)

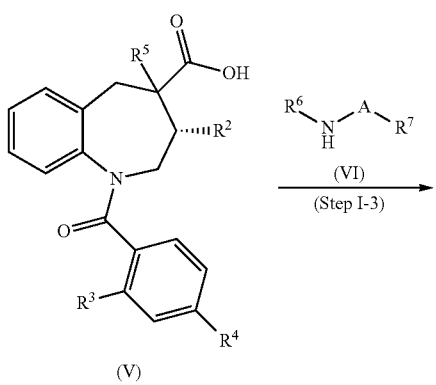

(V)

(VI)

(Step I-3)

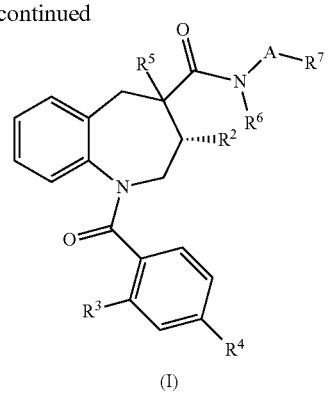

(I)

[wherein $R^2$ is a hydrogen atom or a lower alkyl group; $R^3$ is a lower alkyl group which may be substituted with 1 to 3 fluorine atoms, or a halogen atom; $R^4$ is a lower alkoxy group which may be substituted with a halogen atom, a five-membered aromatic monocyclic heterocyclic group, or a five-membered non-aromatic monocyclic heterocyclic group (provided that each of these heterocyclic groups contains at least one nitrogen atom and may be substituted with a lower alkyl group); $R^5$ is a hydrogen atom, a lower alkyl group, or a halogen atom; A is absent or is a lower alkylene group which may be substituted with a lower alkyl group; $R^6$ is a hydrogen atom or a lower alkyl group; $R^7$ is a hydrogen atom, a hydroxyl group, an aromatic heterocyclic group which may be substituted with a lower alkyl group, a non-aromatic heterocyclic group which may be substituted with an oxo group, or a carbamoyl group which may be substituted with a lower alkyl group; and $R^9$ is a protecting group of a carboxy group].

[Step I-1]

A compound expressed by the general formula (III) is formed into an acid chloride in a suitable solvent (for example, toluene and methylene chloride) using a chlorinating agent (for example, thionyl chloride and oxalyl chloride) under the presence or absence of an additive (for example, N,N-dimethylformamide), and then reacted with a compound expressed by the general formula (IIa) in a suitable solvent (for example, toluene, methylene chloride, tetrahydrofuran and acetonitrile), using a base (for example, triethylamine, N,N-diethylaniline and pyridine) to thus obtain a compound expressed by the general formula (IV). The reaction temperature is from 0° C. to the boiling point of the solvent, and the reaction time is from 30 minutes to 48 hours. In addition, the compounds expressed by the general formula (III) and the general formula (IIa) are products available as commercial products, but can also be manufactured by a method of the reaction step formulas II to IV described below.

[Step 1-2]

In reference to the method described in "Protecting Groups in Organic Synthesis, 3rd Edition, Wiley (1999)", a protecting group $R^9$ in the compound expressed by the general formula (IV) is removed to thus obtain a compound expressed by the general formula (V).

[Step 1-3]

A compound expressed by the general formula (V) and a compound expressed by the general formula (VI) are reacted in a suitable solvent (for example, N,N-dimethylformamide, methylene chloride and tetrahydrofuran), using a condensing agent (for example, 1-ethyl-3-(3-dimethylaminopropyl) carbodiimide hydrochloride and dicyclohexylcarbodiimide)

under the presence or absence of an additive (for example, diisopropylethylamine, 4-dimethylaminopyridine and 1-hydroxybenzotriazole) to thus obtain a compound expressed by the general formula (I). The reaction temperature is from 0° C. to the boiling point of the solvent, and the reaction time is from 30 minutes to 48 hours. In addition, the compound expressed by the general formula (VI) is a product available as a commercial product, but can also be manufactured by a known method.

The compound expressed by the general formula (III), which is used as a starting material in the reaction step formula I, can be manufactured by methods shown in the reaction step formulas II and III described below, methods described in reference examples, or known methods:

[Reaction Step Formula II]

[Formula 21]

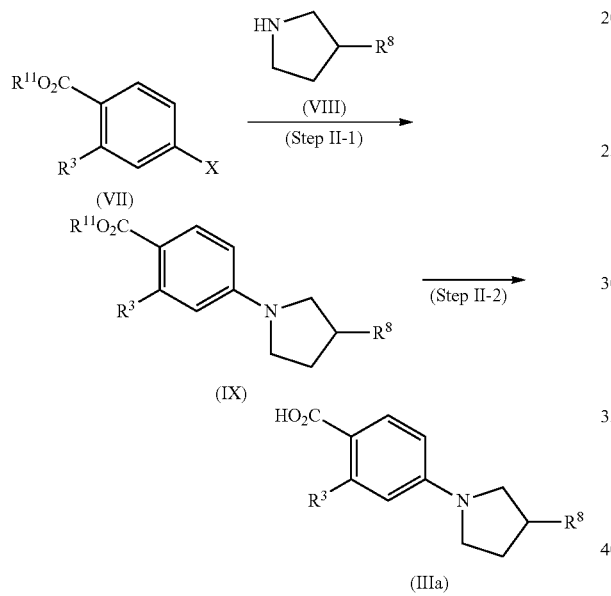

[wherein $R^3$ is a lower alkyl group which may be substituted with 1 to 3 fluorine atoms or a halogen atom; $R^8$ is a lower alkyl group; $R^{11}$ is a protecting group of a carboxy group; and X is a halogen atom or a leaving group such as triflate and mesylate].

[Step II-1]

A compound expressed by the general formula (VII) and a compound expressed by the general formula (VIII) are reacted in a suitable solvent (for example, N,N-dimethylformamide, dimethyl sulfoxide and N-methyl-2-pyrrolidone) using a base (for example, potassium carbonate and sodium carbonate) to thus obtain a compound expressed by the general formula (IX). The reaction temperature is from 0° C. to the boiling point of the solvent, and the reaction time is from 30 minutes to 48 hours. In addition, the compounds expressed by the general formulas (VII) and (VIII) are products available as commercial products, but can also be manufactured by a known method.

[Step II-2]

In reference to the method described in "Protecting Groups in Organic Synthesis, 3rd Edition, Wiley (1999)", a protecting group $R^{11}$ in the compound expressed by the general formula (IX) is removed to thus obtain a compound expressed by the general formula (IIIa).

[Reaction Step Formula III]

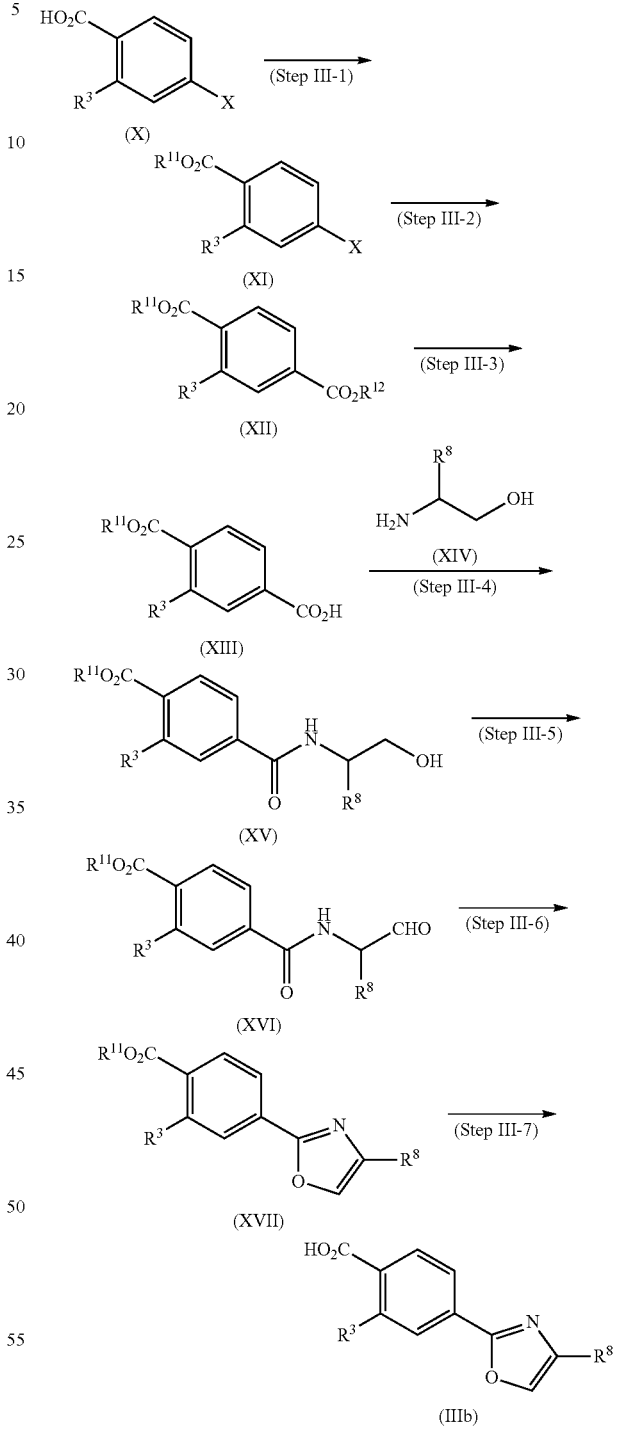

[In the formula, $R^3$ is a lower alkyl group which may be substituted with 1 to 3 fluorine atoms or a halogen atom; $R^8$ is a lower alkyl group; $R^{11}$ is a protecting group of a carboxy group; $R^{12}$ is a protecting group of a carboxy group, which can be distinguished from $R^{11}$ in deprotection; and X is a halogen atom or a leaving group such as triflate and mesylate.]

[Step III-1]

A compound expressed by the general formula (X) is formed into an acid chloride in a suitable solvent (for example, toluene and methylene chloride) using a chlorinating agent (for example, thionyl chloride and oxalyl chloride) under the presence or absence of an additive (for example, N,N-dimethylformamide), then reacted with alcohols (for example, methanol, ethanol, isopropanol and benzyl alcohol) in a suitable solvent (for example, toluene, methylene chloride, tetrahydrofuran and acetonitrile), using a base (for example, triethylamine, N,N-diethylaniline and pyridine) to thus obtain a compound expressed by the general formula (XI). The reaction temperature is from 0° C. to the boiling point of the solvent, and the reaction time is from 30 minutes to 48 hours. In addition, the compound expressed by the general formula (X) is a product available as a commercial product, but can also be manufactured by a known method.

[Step III-2]

A compound expressed by the general formula (XI) is reacted in a suitable solvent (for example, dimethyl sulfoxide, N,N-dimethylformamide, methanol and ethanol) using a base (for example, triethylamine, diisopropylethylamine and cesium carbonate), a palladium catalyst (for example, palladium acetate, palladium chloride, [1,1'-bis(diphenylphosphino)ferrocene]palladium dichloride, and tetrakis(triphenylphosphine)palladium) in a carbon monoxide atmosphere, in the presence or absence of an additive (for example, 1,3-bis(triphenylphosphino) propane and 1,1'-bis(diphenylphosphino) ferrocene) to thus obtain a compound expressed by the general formula (XII). The reaction temperature is from 40° C. to the boiling point of the solvent, and the reaction time is from 30 minutes to 48 hours.

[Step III-3]

In reference to the method described in "Protecting Groups in Organic Synthesis, 3rd Edition, Wiley (1999)", a protecting group $R^{12}$ in the compound expressed by the general formula (XII) is removed to thus obtain a compound expressed by the general formula (XIII).

[Step III-4]

A compound expressed by the general formula (XIII) and a compound expressed by the general formula (XIV) are reacted in a suitable solvent (for example, N,N-dimethylformamide, methylene chloride, and tetrahydrofuran) using a condensing agent (for example, 1-ethyl-3-(3-dimethylaminopropyl)carbodiimide hydrochloride and dicyclohexylcarbodiimide) in the presence or absence of an additive (for example, diisopropylethylamine, 4-dimethylaminopyridine and 1-hydroxybenzotriazole) to thus obtain a compound expressed by the general formula (XV). The reaction temperature is from 0° C. to the boiling point of the solvent, and the reaction time is from 30 minutes to 48 hours. In addition, the compound expressed by the general formula (XIV) is a product available as a commercial product, but can also be manufactured by a known method.

[Step III-5]

A compound expressed by the general formula (XV) is reacted in a suitable solvent (for example, methylene chloride and tetrahydrofuran) using an oxidant (for example, a Dess-Martin reagent and a pyridine sulfur trioxide complex) in the presence or absence of an additive (dimethyl sulfoxide) to thus obtain a compound expressed by the general formula (XVI). The reaction temperature is from 0° C. to room temperature, and the reaction time is from 30 minutes to 48 hours.

[Step III-6]

A compound expressed by the general formula (XVI) is reacted in a suitable solvent (for example, methylene chloride and acetonitirile) using a chlorinating agent (for example, hexachloroethane and 1,2-dibromo-1,1,2,2-tetrachloroethane) and a base (for example, diisopropylethylamine, pyridine and triethylamine) in the presence of an additive (triphenylphosphine) to thus obtain a compound expressed by the general formula (XVII). The reaction temperature is from 0° C. to room temperature, and the reaction time is from 30 minutes to 5 hours.

[Step III-7]

In reference to the method described in "Protecting Groups in Organic Synthesis, 3rd Edition, Wiley (1999)", a protecting group $R^{11}$ in the compound expressed by the general formula (XVII) is removed to thus obtain a compound expressed by the general formula (IIIb).

The compound expressed by the general formula (IIa), which is used as a starting material in the reaction step formula I, can be manufactured by methods shown in the reaction step formulas IV to VI described below, methods described in reference examples, or a method of combining known methods.

[Reaction Step Formula IV]

[Formula 23]

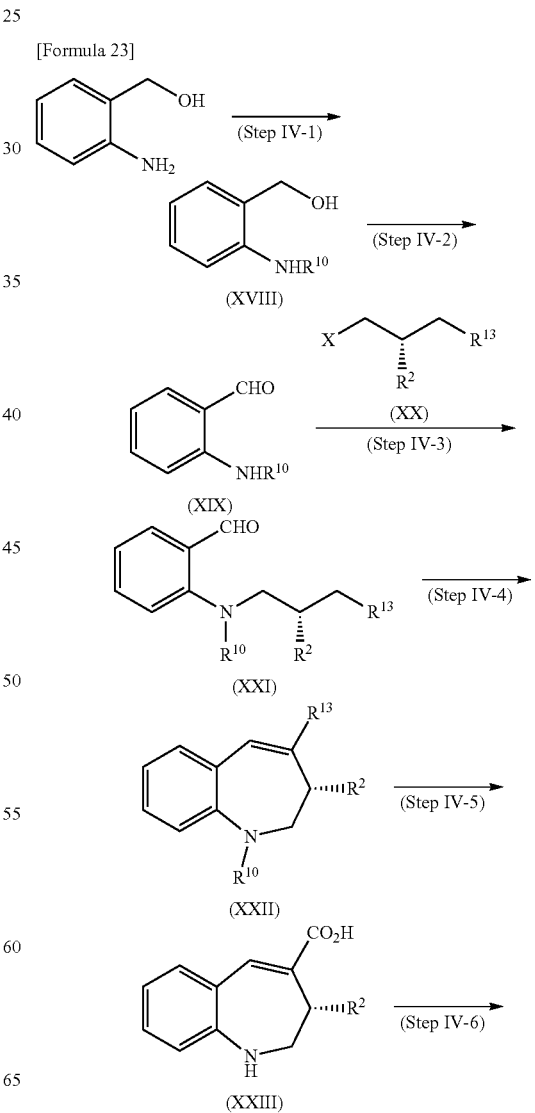

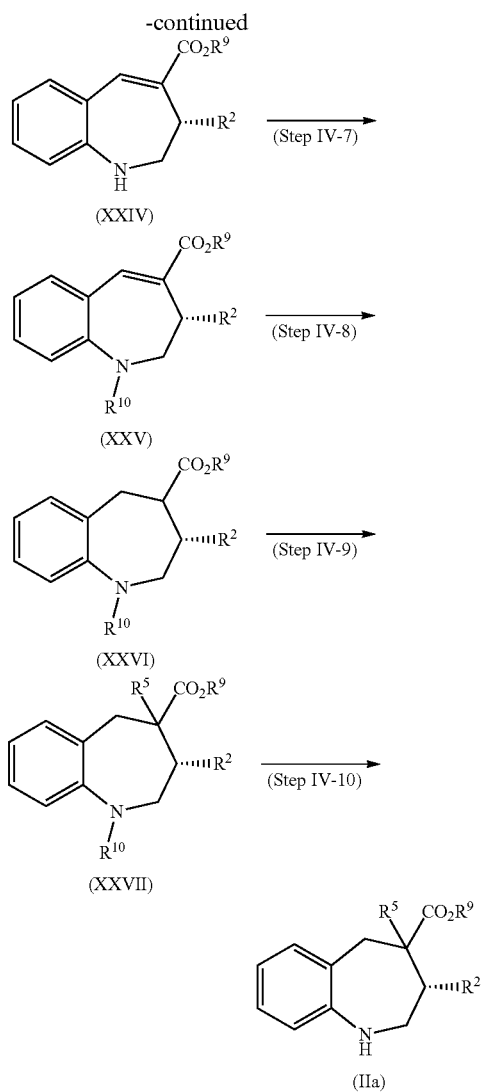

[In the formula, $R^2$ is a hydrogen atom or a lower alkyl group; $R^5$ is a lower alkyl group or a halogen atom; $R^9$ is a protecting group of a carboxy group; $R^{10}$ is a protecting group of a nitrogen atom; $R^{13}$ is a cyano group or a carboxylic acid derivative (for example, methyl ester and ethyl ester).]

[Step IV-1]

In reference to the method described in "Protecting Groups in Organic Synthesis, 3rd Edition, Wiley (1999)", a nitrogen atom of (2-aminophenyl)methanol is protected with $R^{10}$ to thus obtain a compound expressed by the general formula (VIII). In addition, (2-aminophenyl)methanol is available as a commercial product.

[Step IV-2]

A compound expressed by the general formula (XVIII) is reacted in a suitable solvent (for example, methylene chloride, chloroform, acetone and tetrahydrofuran) using manganese (IV) oxide to thus obtain a compound expressed by the general formula (XIX). The reaction temperature is from 0° C. to the boiling point of the solvent, and the reaction time is from 30 minutes to 48 hours.

[Step IV-3]

A compound expressed by the general formula (XIX) and a compound expressed by the general formula (XX) are reacted in a suitable solvent (for example, N,N-dimethylformamide and dimethyl sulfoxide) using a base (for example, potassium carbonate and sodium hydride) to thus obtain a compound expressed by the general formula (XXI). The reaction temperature is from 0° C. to the boiling point of the solvent, and the reaction time is from 30 minutes to 48 hours. In addition, a compound expressed by the general formula (XX) can be manufactured by a method of the reaction step formula VII described below.

[Step IV-4]

A compound expressed by the general formula (XXI) is reacted in a suitable solvent (for example, diethyl carbonate and ethanol) using a base (for example, sodium ethoxide and potassium t-butoxide) in the presence or absence of an additive (for example, sodium bromide, lithium bromide and sodium iodide) to thus obtain a compound expressed by the general formula (XXII).

[Step IV-5]

A compound expressed by the general formula (XXII) is reacted in a suitable solvent (for example, acetic acid and water) using an acid (for example, sulfuric acid and hydrochloric acid) to thus obtain a compound expressed by the general formula (XXIII). The reaction temperature is from room temperature to the boiling point of the solvent, and the reaction time is from 12 hours to 7 days.

[Step IV-6]

In reference to the method described in "Protecting Groups in Organic Synthesis, 3rd Edition, Wiley (1999)", a carboxy group in a compound expressed by the general formula (XXIII) is protected with $R^9$ to thus obtain a compound expressed by the general formula (XXIV).

[Step IV-7]

In reference to the method described in "Protecting Groups in Organic Synthesis, 3rd Edition, Wiley (1999)", a nitrogen atom in a compound expressed by the general formula (XXIV) is protected with $R^{10}$ to thus obtain a compound expressed by the general formula (XXV).

[Step IV-8]

A compound expressed by the general formula (XXV) is reacted in a suitable solvent (for example, methanol, ethanol and 1,4-dioxane) using a palladium catalyst (for example, palladium on carbon and Pearlman's catalyst) in a hydrogen atmosphere to thus obtain a compound expressed by the general formula (XXVI). The reaction temperature is from room temperature to 60° C., and the reaction time is from 1 hour to 48 hours.

[Step IV-9]

A compound expressed by the general formula (XXVI) and an electrophilic agent (for example, methyl iodide, methyl bromide, ethyl iodide and N-fluorobenzenesulfonimide) are reacted in a suitable solvent (for example, tetrahydrofuran and diethyl ether) using a base (for example, lithium diisopropylamine, n-butyl lithium and t-butyl lithium) to thus obtain a compound expressed by the general formula (XXVII). The reaction temperature is from −78° C. to 0° C., and the reaction time is from 30 minutes to 24 hours.

[Step IV-10]

In reference to the method described in "Protecting Groups in Organic Synthesis, 3rd Edition, Wiley (1999)", a protecting group $R^{10}$ in the compound expressed by the general formula (XXVII) is removed to thus obtain a compound expressed by the general formula (IIa).

[Reaction Step Formula V]

[Formula 24]

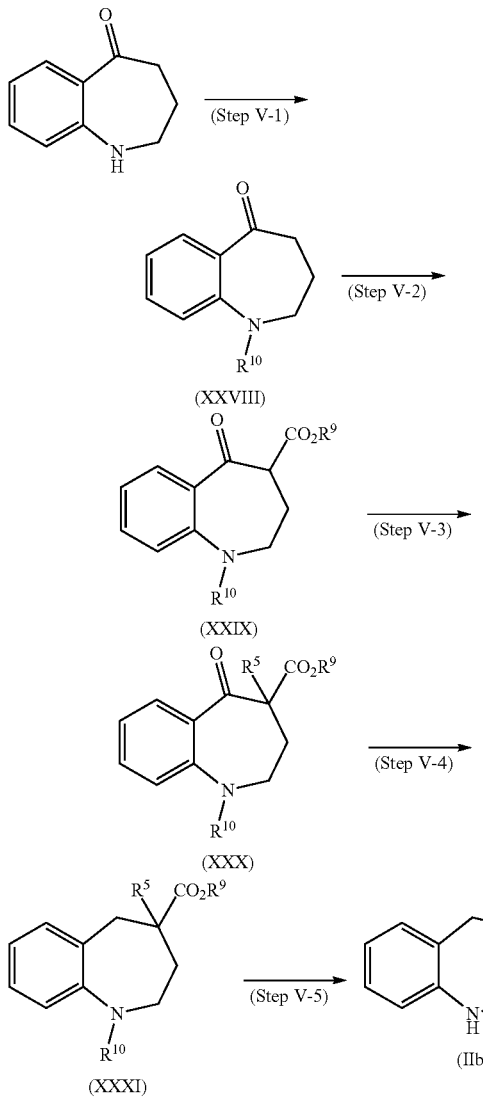

[In the formula, $R^5$ is a lower alkyl group or a halogen atom; $R^9$ is a protecting group of a carboxy group; and $R^{10}$ is a protecting group of a nitrogen atom.]

[Step V-1]

In reference to the method described in "Protecting Groups in Organic Synthesis, 3rd Edition, Wiley (1999)", a nitrogen atom in 3,4-dihydro-1H-benzo[b]azepine-5(2H)-one is protected with $R^{10}$ to thus obtain a compound expressed by the general formula (XXVIII). In addition, 3,4-dihydro-1H-benzo[b]azepine-5(2H)-one is available as a commercial product.

[Step V-2]

A compound expressed by the general formula (XXVIII) is reacted in a suitable solvent (for example, dimethyl carbonate and diethyl carbonate) using a base (for example, sodium methoxide and sodium ethoxide) to thus obtain a compound expressed by the general formula (XXIX). The reaction temperature is from 0° C. to the boiling point of the solvent, and the reaction time is from 30 minutes to 5 hours.

[Step V-3]

A compound expressed by the general formula (XXIX) and an electrophilic agent (for example, methyl iodide, methyl bromide, ethyl iodide and N-fluorobenzenesulfonimide) are reacted in a suitable solvent (for example, tetrahydrofuran, acetone and ethanol) using a base (for example, potassium carbonate, cesium carbonate and sodium hydride) to thus obtain a compound expressed by the general formula (XXX). The reaction temperature is from 0° C. to the boiling point of the solvent, and the reaction time is from 30 minutes to 48 hours.

[Step V-4]

A compound expressed by the general formula (XXX) and a reducing agent (for example, triethylsilane) are reacted in a suitable solvent (for example, methylene chloride and tetrahydrofuran) using an acid (for example, trifluoroacetic acid, methanesulfonic acid and boron trifluoride diethyl ether complex) to thus obtain a compound expressed by the general formula (XXXI). The reaction temperature is from 0° C. to the boiling point of the solvent, and the reaction time is from 30 minutes to 48 hours.

[Step V-5]

In reference to the method described in "Protecting Groups in Organic Synthesis, 3rd Edition, Wiley (1999)", a protecting group $R^{10}$ in the compound expressed by the general formula (XXXI) is removed to thus obtain a compound expressed by the general formula (IIb).

[Reaction Step Formula VI]

[Formula 25]

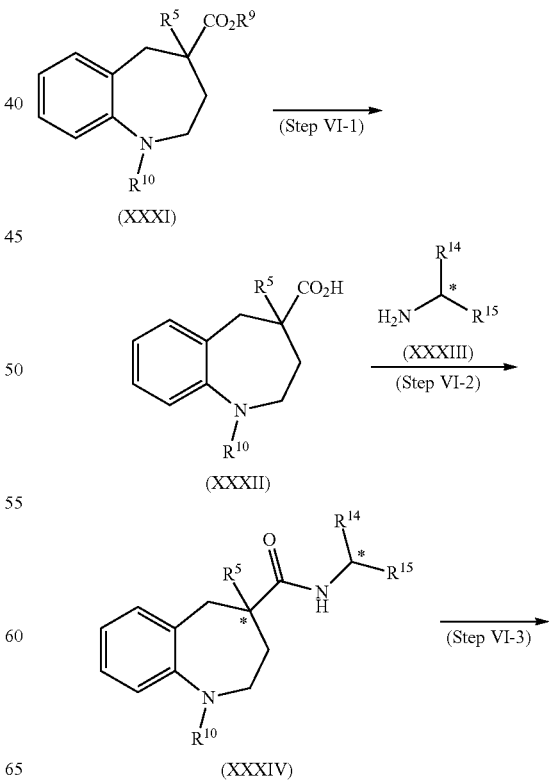

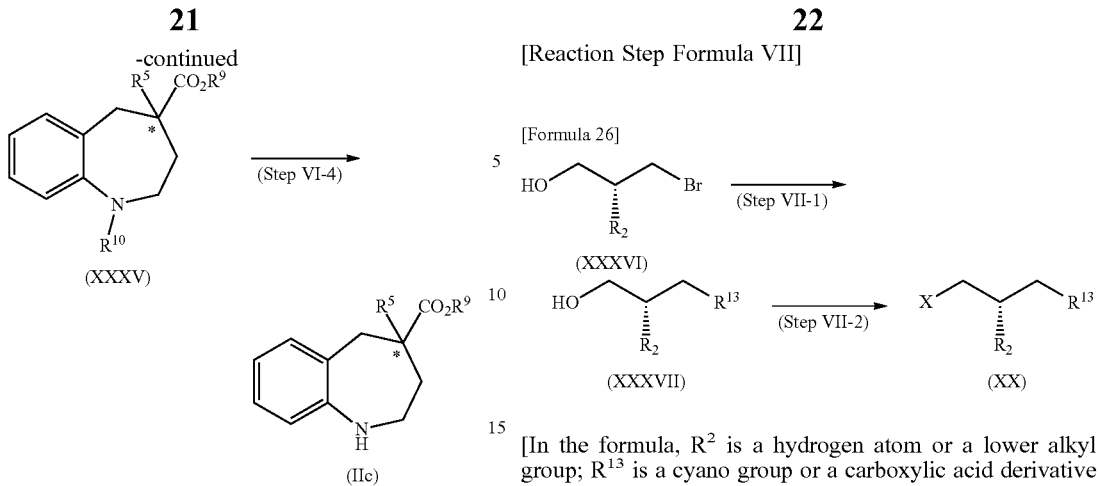

[Reaction Step Formula VII]

[In the formula, $R^5$ is a hydrogen atom, a lower alkyl group, or a halogen atom; $R^9$ is a protecting group of a carboxy group; $R^{10}$ is a protecting group of a nitrogen atom; $R^{14}$ and $R^{15}$ are alkyl groups which are different from each other and may be substituted or aryl groups which may be substituted.]

[Step VI-1]

In reference to the method described in "Protecting Groups in Organic Synthesis, 3rd Edition, Wiley (1999)", a protecting group $R^9$ in the compound expressed by the general formula (XXXI) is removed to thus obtain a compound expressed by the general formula (XXXII).

[Step VI-2]

A compound expressed by the general formula (XXXII) and a compound expressed by the general formula (XXXIII) are reacted in a suitable solvent (for example, N,N-dimethylformamide, methylene chloride and tetrahydrofuran) using a condensing agent (for example, 1-ethyl-3-(3-dimethylaminopropyl)carbodiimide hydrochloride and dicyclohexyl carbodiimide) in the presence or absence of an additive (for example, diisopropylethylamine, 4-dimethylaminopyridine and 1-hydroxybenzotriazole) to thus obtain a compound expressed by the general formula (XXXIV). The reaction temperature is from 0° C. to the boiling point of the solvent, and the reaction time is from 30 minutes to 48 hours.

[Step VI-3]

A compound expressed by the general formula (XXXIV) is reacted in a suitable solvent (for example, methanol, ethanol and benzyl alcohol) using an acid (for example, sulfuric acid and hydrochloric acid) to thus obtain a compound expressed by the general formula (XXXV). The reaction temperature is from room temperature to the boiling point of the solvent, and the reaction time is from 30 minutes to 72 hours.

[Step VI-4]

In reference to the method described in "Protecting Groups in Organic Synthesis, 3rd Edition, Wiley (1999)", a protecting group $R^{10}$ in the compound expressed by the general formula (XXXV) is removed to thus obtain a compound expressed by the general formula (IIc).

The compound expressed by the general formula (XX), which is used in the reaction step formula IV, can be manufactured by the method shown in the reaction step formula VII described below, methods described in reference examples, or a method of combining known methods.

[In the formula, $R^2$ is a hydrogen atom or a lower alkyl group; $R^{13}$ is a cyano group or a carboxylic acid derivative (for example, methyl ester and ethyl ester); and X is a halogen atom or a leaving group such as triflate and mesylate.]

[Step VII-1]

A compound expressed by the general formula (XXXVI) is reacted in a suitable solvent (for example, N,N-dimethylformamide, dimethyl sulfoxide and acetonitrile) using a cyanating agent (for example, sodium cyanide and potassium cyanide) in a presence or absence of an additive (for example, tetrabutyl ammonium bromide, sodium iodide and 18-crown-6-ether) to thus obtain a compound expressed by the general formula (XXXVII). The reaction temperature is from room temperature to the boiling point of the solvent, and the reaction time is from 30 minutes to 24 hours.

[Step VII-2]

A compound expressed by the general formula (XXXVII) and a nucleophilic agent (for example, thionyl chloride, methanesulfonyl chloride, and tri fluoromethanesulfonyl anhydride) are reacted in a suitable solvent (for example, methylene chloride and toluene), using a base (for example, triethylamine, diisopropylethylamine, and pyridine) to thus obtain a compound expressed by the general formula (XX). The reaction temperature is from 0° C. to room temperature, and the reaction time is from 30 minutes to 24 hours.

Some of other compounds used as starting materials, intermediates or reagents, which are necessary for manufacturing the compound of the present invention, are available as commercial products and also can be manufactured in reference to known methods.

It may be effective to introduce a suitable protecting group into a substituent (for example, hydroxyl group, amino group, and carboxy group), which is contained in the compound of the present invention or a compound used for production of the compound, in a stage of a starting material or an intermediate for production of the compound in some cases, and a protecting group described in "Protecting Groups in Organic Synthesis, 3rd Edition, Wiley (1999)" described above may be suitably selected if needed.

In order to isolate or purify the compound of the present invention and a compound used for production of the compound from a reaction solution, a generally used method can be used. For example, solvent extraction, ion exchange resin, column chromatography using silica gel, alumina, or the like, as a carrier, high performance liquid chromatography (HPLC) preparative isolation, thin layer chromatography, a scavenger resin, recrystallization, and the like, can be used, and these isolation and purification methods can be used solely or in combination. Isolation and purification may be carried out every time after each reaction, or after completion of some reactions.

When the compound in the description has an asymmetric carbon and optical isomers exist, these optical isomers can be divided as diastereomers by a general optical resolution method of an racemic compound, for example, fractional crystallization of recrystallizing diastereomers as a diastereomer salt formed with a general optically active compound, or a reaction with a general optically active compound, in a general method such as chromatography. In addition, each optical isomer can be isolated also by high performance liquid chromatography (HPLC) preparative isolation using a column for separation of an optical active material.

The compound of the present invention produced as described above acts as a V2 receptor agonist and is therefore used as a pharmaceutical composition for prevention or treatment of central diabetes insipidus, nocturnal enuresis, nocturia, overactive bladder, hemophilia, or Von Willebrand disease. Note that the main compound in the compound of the invention selectively acts on a V2 receptor and is thus advantageous from the viewpoint of side effects. In addition, as compared to conventionally known compounds having a V2 receptor agonistic action, the compound of the present invention has a low inhibition action to drug metabolizing enzymes CYP3A4 and CYP2C9, and furthermore, in view of physical properties as a pharmaceutical product such as solubility and membrane permeability and in view of kinetics such as plasma clearance and distribution volume, has excellent properties and therefore, the present invention can be safely used.

As an administration form when the compound of the present invention is used as a medical drug, various administration forms described in the general rules for preparations in "the Japanese Pharmacopoeia" can be selected according to purposes. For example, when the compound is prepared into a tablet form, in general, components capable of oral intake used in this field may be selected. For example, the components correspond to vehicles such as lactose, crystalline cellulose, sucrose and potassium phosphate. Furthermore, various additives which are usually regularly used in the drug formulation field such as a binder, a disintegrating agent, a lubricant and a deflocculating agent may be blended if desired.

An amount of the compound of the present invention contained in the preparation of the present invention as an active ingredient is not particularly limited, and suitably selected from a wide range. An administration amount of the compound of the present invention is suitably determined according to its usage, an age, sex and other conditions of a patient, and an extent of a disease, and in the case of oral administration, an amount of the compound of the present invention in one day is from about 1 μg to 100 mg per 1 kg of the body weight, preferably appropriately from about 10 μg to 20 mg, and more preferably appropriately from about 50 μg to 5 mg, and such an amount can be suitably administered 1 to 4 times separately in one day. However, since an administration amount and the number of times are determined in consideration of concerned situations including an extent of symptom to be treated, selection of a compound to be administered, and a selected administration route, the above described administration amount ranges and numbers of times do not limit the scope of the present invention.

EXAMPLES

Hereinbelow, the content of the present invention will be more specifically explained in reference to examples, reference examples and pharmacological test examples, and the technical range of the present invention is not limited to the described contents.

Nuclear magnetic resonance ($^1$H-NMR) spectra in the following examples and reference examples were described using tetramethylsilane as a standard substance and expressing a chemical shift value as a δ value (ppm). For division patterns, a single line was shown by "s", a double line was shown by "d", a triple line was shown by "t", a quadruple line was shown by "q", a quintuple line was shown by "quin", a multiple line was shown by "m", and a broad line was shown by "br". Mass analysis was conducted in electrospray ionization (ESI). In tables, methyl group was shown by "Me" and ethyl group was shown by "Et".

Reference Example 1

(S)-2-methyl-4-(3-methylpyrrolidine-1-yl)benzoic acid methyl ester 4-fluoro-2-methyl benzoic acid methyl ester (970 mg) was dissolved into N-methyl-2-pyrrolidone (20 mL), thereto was added (S)-3-methylpyrrolidine hydrochloride (772 mg) in the presence of potassium carbonate (2.39 g), and the reaction mixture was then stirred at 120° C. for 6 hours. The reaction solution was returned to room temperature, added with ethyl acetate, washed with saturated saline, and dried with anhydrous sodium sulfate. After filtration, the filtrate was concentrated with a reduced pressure and the obtained residue was purified by silica gel column chromatography (ethyl acetate/hexane=1/6) to thus obtain the title compound (720 mg) as a colorless oily substance.

$^1$H-NMR (400 MHz, CDCl$_3$) δ7.88 (d, J=8.0 Hz, 1H), 6.34-6.30 (m, 2H), 3.82 (s, 3H), 3.51-3.47 (m, 1H), 3.45-3.39 (m, 1H), 3.36-3.29 (m, 1H), 2.92-2.88 (m, 1H), 2.59 (s, 3H), 2.45-2.32 (m, 1H), 2.17-2.10 (m, 1H), 1.68-1.58 (m, 1H), 1.13 (d, J=8.0 Hz, 3H).

ESI/MS (m/z) 234 (M+H)$^+$.

Reference Example 2

(S)-2-methyl-4-(3-methylpyrrolidine-1-yl)benzoic acid (S)-2-methyl-4-(3-methylpyrrolidine-1-yl)benzoic acid methyl ester (710 mg) was dissolved into methanol (7 mL), thereto were added water (6 mL) and lithium hydroxide monohydrate (383 mg), and the reaction mixture was stirred at 60° C. for 6 hours. The reaction solution was concentrated with a reduced pressure, added with ethyl acetate to be acidified with an aqueous 5% citric acid solution, and the organic phase was then washed with saturated saline and dried with anhydrous sodium sulfate. After filtration, the filtrate was concentrated with a reduced pressure to thus obtain the title compound (660 mg) as a white solid.

$^1$H-NMR (400 MHz, CDCl$_3$) δ12.36 (brs, 1H), 8.00 (d, J=8.0 Hz, 1H), 6.36 (d, J=8.0 Hz, 1H), 6.31 (s, 1H), 3.51-3.48 (m, 1H), 3.47-3.41 (m, 1H), 3.37-3.31 (m, 1H), 2.93-2.89 (m, 1H), 2.62 (s, 3H), 2.42-2.35 (m, 1H), 2.18-2.10 (m, 1H), 1.68-1.59 (m, 1H), 1.13 (d, J=8.0 Hz, 3H).

ESI/MS (m/z) 220 (M+H)$^+$, 218 (M−H)$^-$.

Reference Example 3

4-bromo-2-methyl benzoic acid benzyl ester 4-bromo-2-methyl benzoic acid (2.15 g) was dissolved into thionyl chloride (5.0 mL) and N,N-dimethyl formamide (100 μL) and the reaction mixture was stirred at 50° C. for 2 hours. The reaction solution was concentrated with a reduced pressure, the obtained residue was dissolved into methylene chloride (10 mL), thereto were added a benzyl alcohol (1.0 mL) and pyridine (1.6 mL), and the reaction mixture was stirred at room temperature for 30 minutes. An aqueous saturated sodium hydrogen carbonate solution was added to the reaction solution and the reaction solution was extracted with methylene chloride. The organic phase was washed with water and saturated saline in sequence, and dried with anhydrous sodium sulfate. After filtration, the filtrate was concentrated with a reduced pressure, and the obtained residue was purified by silica gel column chromatography (hexane/ethyl acetate=1/0 to 6/1) to thus obtain the title compound (2.65 g).

$^1$H-NMR (400 MHz, CDCl$_3$) δ7.82 (d, J=8.4 Hz, 1H), 7.47-7.30 (m, 7H), 5.33 (s, 2H), 2.58 (s, 3H).

Reference Example 4

4-[(benzyloxy) carbonyl]-3-methyl benzoic acid methyl ester 4-bromo-2-methyl benzoic acid benzyl ester (4.86 g) was dissolved into a mixed solvent of dimethyl sulfoxide (48 mL) and methanol (48 mL), and thereto were added palladium acetate (358 mg), 1,3-bis(diphenylphosphino)propane (657 mg) and diisopropylethylamine (5.4 mL), and the reaction mixture was replaced with carbon monoxide and stirred at 60° C. overnight. The reaction solution was added with water and extracted with ethyl acetate. The organic phase was washed with water and saturated saline in sequence, and then dried with anhydrous sodium sulfate. After filtration, the filtrate was concentrated with a reduced pressure, and the obtained residue was purified by silica gel column chromatography (hexane/ethyl acetate=24/1 to 3/1) to thus obtain the title compound (3.91 g).

$^1$H-NMR (400 MHz, CDCl$_3$) δ7.97 (d, J=8.1 Hz, 1H), 7.94-7.90 (m, 1H), 7.87 (dd, J=8.1, 1.7 Hz, 1H), 7.49-7.43 (m, 2H), 7.43-7.33 (m, 3H), 5.36 (s, 2H), 3.93 (s, 3H), 2.63 (s, 3H).

ESI/MS (m/z) 285 (M+H)$^+$.

Reference Example 5

4-[(benzyloxy)carbonyl]-3-methyl benzoic acid

4-[(benzyloxy) carbonyl]-3-methyl benzoic acid methyl ester (3.03 g) was dissolved into a mixed solvent of tetrahydrofuran (30 mL) and water (30 mL), thereto was added lithium hydroxide monohydrate (671 mg) and the reaction mixture was stirred at room temperature for 2 hours. The reaction solution was added with 1 M hydrochloric acid to be acidified, and then extracted with ethyl acetate. The organic phase was washed with water and saturated saline in sequence, and dried with anhydrous sodium sulfate. After filtration, the filtrate was concentrated with a reduced pressure to thus obtain the title compound (2.84 g) as a white solid.

$^1$H-NMR (400 MHz, DMSO) δ13.21 (s, 1H), 7.92 (d, J=8.0 Hz, 1H), 7.90-7.77 (m, 2H), 7.53-7.30 (m, 5H), 5.35 (s, 2H), 2.55 (s, 3H).

ESI/MS (m/z) 269 (M–H)$^-$.

Reference Example 6

4-[(1-hydroxypropane-2-yl)carbamoyl]-2-methyl benzoic acid benzyl ester

4-[(benzyloxy)carbonyl]-3-methyl benzoic acid (1.24 g) was dissolved into N,N-dimethylformamide (23 mL), thereto were added 1-ethyl-3-(3-dimethylaminopropyl)carbodiimide hydrochloride (1.76 g), 1-hydroxybenzotriazole (1.41 g), diisopropylethylamine (3.1 mL) and DL-2-amino-1-propanol (730 μL), and the reaction mixture was stirred at 40° C. overnight. The reaction solution was added with an aqueous saturated sodium hydrogen carbonate solution and extracted with ethyl acetate. The organic phase was washed with water and saturated saline in sequence, and dried with anhydrous sodium sulfate. After filtration, the filtrate was concentrated with a reduced pressure, and the obtained residue was purified by silica gel column chromatography (chloroform/ethyl acetate=1/2) to thus obtain the title compound (1.07 g).

$^1$H-NMR (400 MHz, CDCl$_3$) δ7.90 (d, J=8.1 Hz, 1H), 7.60 (s, 1H), 7.56 (d, J=8.1 Hz, 1H), 7.48-7.29 (m, 5H), 6.71 (brs, 1H), 5.32 (s, 2H), 4.31-4.15 (m, 1H), 3.73 (dd, J=11.1, 3.7 Hz, 1H), 3.61 (dd, J=11.1, 5.5 Hz, 1H), 3.37 (brs, 1H), 2.56 (s, 3H), 1.25 (d, J=6.8 Hz, 3H).

ESI/MS (m/z) 328 (M+H)$^+$, 326 (M–H)$^-$.

Reference Example 7

2-methyl-4-[(1-oxopropane-2-yl)carbamoyl]benzoic acid benzyl ester

4-[(1-hydroxypropane-2-yl) carbamoyl]-2-methyl benzoic acid benzyl ester (1.07 g) was dissolved into methylene chloride (16 mL), thereto was added a Dess-Martin reagent (2.08 g) at 0° C., and the reaction mixture was stirred at room temperature for 1 hour. The reaction solution was added with an aqueous saturated sodium hydrogen carbonate solution and extracted with methylene chloride. The organic phase was washed with an aqueous saturated sodium hydrogen carbonate solution and saturated saline in sequence, and then dried with anhydrous sodium sulfate. After filtration, the filtrate was concentrated with a reduced pressure, and the obtained residue was purified by silica gel column chromatography (hexane/ethyl acetate=1/1 to 2/5) to thus obtain the title compound (846 mg).

$^1$H-NMR (400 MHz, CDCl$_3$) δ9.64 (s, 1H), 7.98 (d, J=8.1 Hz, 1H), 7.68 (s, 1H), 7.66-7.59 (m, 1H), 7.48-7.31 (m, 5H), 7.01 (brs, 1H), 5.35 (s, 2H), 4.79-4.62 (m, 1H), 2.63 (s, 3H), 1.49 (d, J=7.4 Hz, 3H).

ESI/MS (m/z) 326 (M+H)$^+$, 324 (M–H)$^-$.

Reference Example 8

2-methyl-4-(4-methyloxazol-2-yl)benzoic acid benzyl ester

Triphenylphosphine (2.05 g) and hexachloroethane (1.85 g) were dissolved into acetonitrile (18 mL), thereto was added an acetonitrile solution (8 mL) containing 2-methyl-4-[(1-oxopropane-2-yl)carbamoyl]benzoic acid benzyl ester (846 mg), and the reaction mixture was stirred at room temperature for 10 minutes. The reaction mixture was added with pyridine (1.3 mL) and stirred at room temperature for 1 hour. The reaction solution was added with water and extracted with ethyl acetate. The organic phase was washed with water and saturated saline in sequence, and then dried with anhydrous sodium sulfate. After filtration, the filtrate was concentrated with a reduced pressure, and the obtained residue was purified by silica gel column chromatography (hexane/ethyl acetate=12/1 to 5/2) to thus obtain the title compound (691 mg).

$^1$H-NMR (400 MHz, CDCl$_3$) δ8.02 (d, J=8.2 Hz, 1H), 7.95-7.90 (m, 1H), 7.89-7.82 (m, 1H), 7.50-7.30 (m, 6H), 5.36 (s, 2H), 2.66 (s, 3H), 2.26 (d, J=1.2 Hz, 3H).

ESI/MS (m/z) 308 (M+H)$^+$.

Reference Example 9

2-methyl-4-(4-methyloxazol-2-yl)benzoic acid 2-methyl-4-(4-methyloxazol-2-yl)benzoic acid benzyl ester (69.0 mg) was dissolved into methanol (8 mL), thereto was added an aqueous 1 M sodium hydroxide solution (4 mL), and the reaction mixture was stirred at 50° C. for 3 hours. The reaction solution was concentrated with a reduced pressure, the obtained residue was added with 1 M hydrochloric acid to be acidified, and the precipitated crystal was then obtained by filtration and washed with water to thus obtain the title compound (429 mg) as a white crystal.

$^1$H-NMR (400 MHz, DMSO) δ7.97 (q, J=1.2 Hz, 1H), 7.93 (d, J=8.1 Hz, 1H), 7.90-7.86 (m, 1H), 7.86-7.79 (m, 1H), 2.59 (s, 3H), 2.18 (d, J=1.2 Hz, 3H).

ESI/MS (m/z) 218 (M+H)$^+$, 216 (M−H)$^-$.

Reference Example 10

1-tosyl-2,3-dihydro-1H-benzo[b]azepine-4-carboxylic acid ethyl ester (2-aminophenyl)methanol (13.4 g) was dissolved into chloroform (400 mL) and cooled to 0° C. Thereto were added pyridine (11 mL) and p-toluenesulfonyl chloride (24.8 g) and the reaction mixture was stirred at room temperature for 17 hours. The reaction solution was diluted with water and added with 6 M hydrochloric acid to be acidified, and then extracted with chloroform. The organic phase was washed with an aqueous saturated sodium hydrogen carbonate solution and saturated saline in sequence, and then dried with anhydrous sodium sulfate. After filtration, the filtrate was concentrated with a reduced pressure to thus obtain N-[2-(hydroxymethyl)phenyl]-4-methylbenzenesulfonamide.

The above described N-[2-(hydroxymethyl)phenyl]-4-methylbenzenesulfonamide (32.0 g) was dissolved into acetone (480 mL), thereto was added manganese (IV) oxide (75.0 g), and the reaction mixture was heated to reflux for 24 hours. After filtration, the reaction solution was washed with ethyl acetate. The filtrate was concentrated with a reduced pressure, and the residue was diluted with water and extracted with ethyl acetate. The organic phase was washed with saturated saline, and then dried with anhydrous sodium sulfate. After filtration, the filtrate was concentrated with a reduced pressure to thus obtain N-(2-formylphenyl)-4-methylbenzenesulfonamide.

The above described N-(2-formylphenyl)-4-methylbenzenesulfonamide (24.0 g) was dissolved into N,N-dimethylformamide (300 mL), thereto were added ethyl bromobutyrate (36.4 g) and potassium carbonate (36.1 g), and the reaction mixture was stirred at 80° C. for 36 hours. The reaction solution was diluted with water and extracted with ethyl acetate. The organic phase was washed with an aqueous saturated sodium hydrogen carbonate solution and saturated saline in sequence, and then dried with anhydrous sodium sulfate. After filtration, the filtrate was concentrated with a reduced pressure to thus obtain 4-EN-(2-formylphenyl)-4-methylphenylsulfoneamide]butyric acid ethyl ester.

The above described 4-[N-(2-formylphenyl)-4-methylphenylsulfoneamide]butyric acid ethyl ester was dissolved into diethyl carbonate (480 mL), thereto was added a 20% sodium ethoxide-ethanol solution (43.1 g), and the reaction mixture was stirred at room temperature for 4 hours. The reaction solution was diluted with water and added with 6 M hydrochloric acid to be acidified, and then extracted with ethyl acetate. The organic phase was washed with saturated saline, and then dried with anhydrous sodium sulfate. After filtration, the residue obtained by concentrating the filtrate with a reduced pressure was purified by silica gel column chromatography (ethyl acetate/hexane=1/10 to 1/4) to thus obtain the title compound (18.2 g) as a yellow white oily substance.

$^1$H-NMR (400 MHz, CDCl$_3$) δ6.97-6.87 (m, 1H), 6.61-6.53 (m, 1H), 6.48 (d, J=7.9 Hz, 1H), 3.86 (s, 1H), 3.14-3.00 (m, 2H), 2.86-2.76 (m, 2H), 1.86-1.74 (m, 2H), 1.69-1.60 (m, 2H).

Reference Example 11

2,3-dihydro-1H-benzo[b]azepine-4-carboxylic acid methyl ester 1-tosyl-2,3-dihydro-1H-benzo[b]azepine-4-carboxylic acid ethyl ester (18.2 g) was dissolved into acetic acid (180 mL), thereto were added sulfuric acid (90 mL) and water (9 mL), and the reaction mixture was stirred at 90° C. for 36 hours. The reaction solution was cooled to 0° C., and diluted with methylene chloride and water. The mixed solution was added with 5 M sodium hydroxide to be neutralized, and then extracted with methylene chloride. The organic phase was washed with saturated saline, and dried with anhydrous sodium sulfate. After filtration, the filtrate was concentrated with a reduced pressure to thus obtain 2,3-dihydro-1H-benzo[b]azepine-4-carboxylic acid.

The above described 2,3-dihydro-1H-benzo[b]azepine-4-carboxylic acid was dissolved into methanol (180 mL), thereto was dropped sulfuric acid (10 mL) at room temperature, and the reaction mixture was heated to reflux for 17 hours. The reaction solution was concentrated with a reduced pressure, and the obtained residue was diluted with water, and then added with 5 M sodium hydroxide to be neutralized, thereafter extracting with ethyl acetate. The organic phase was washed with saturated saline, and then dried with anhydrous sodium sulfate. After filtration, the residue obtained by concentrating the filtrate with a reduced pressure was purified by silica gel column chromatography (ethyl acetate/hexane=1/10 to 1/4) to thus obtain the title compound (8.30 g) as a yellow white solid.

$^1$H-NMR (400 MHz, CDCl$_3$) δ7.65 (s, 1H), 7.29-7.23 (m, 1H), 7.13-7.06 (m, 1H), 6.78-6.72 (m, 1H), 6.63-6.57 (m, 1H), 4.55 (s, 1H), 3.80 (s, 3H), 3.42-3.34 (m, 2H), 2.89-2.83 (m, 2H).

Reference Example 12

1-tosyl-3,4-dihydro-1H-benzo[b]azepine-5(2H)-one 3,4-dihydro-1H-benzo[b]azepine-5(2H)-one (10.0 g) was dissolved into pyridine (30 mL), thereto was added p-toluenesulfonyl chloride (13.6 g) under an ice bath and the reaction mixture was stirred at room temperature for 12 hours. The reaction solution was added with water (60 mL)

and then stirred at room temperature for 40 minutes. The obtained crystal was collected by filtration and washed with water, and then dried to thus obtain the title compound (18.9 g) as a light yellow white solid.

$^1$H-NMR (400 MHz, CDCl$_3$) δ7.71 (ddd, J=7.8, 1.7, 0.4 Hz, 1H), 7.59 (d, J=8.3 Hz, 2H), 7.55-7.46 (m, 2H), 7.41-7.35 (m, 1H), 7.23-7.30 (m, 2H), 3.86 (t, J=6.6 Hz, 2H), 2.45-2.39 (m, 5H), 2.00-1.91 (m, 2H).

ESI/MS (m/z) 316 (M+H)$^+$.

Reference Example 13

5-oxo-1-tosyl-2,3,4,5-tetrahydro-1H-benzo[b] azepine-4-carboxylic acid methyl ester 1-tosyl-3,4-dihydro-1H-benzo[b]azepine-5(2H)-one (47.3 g) was dissolved into dimethyl carbonate (300 mL), thereto was added sodium methoxide (48.6 g) at room temperature and the reaction mixture was stirred at 70° C. for 40 minutes. Then, the reaction solution was cooled to room temperature and charged into iced water, thereafter extracting with ethyl acetate, the reaction solution was washed with water and saturated saline and then dried with anhydrous sodium sulfate. The obtained residue was added with methanol and the precipitated crystal was collected by filtration to thus obtain the title compound (43.8 g).

$^1$H-NMR (400 MHz, CDCl$_3$) δ11.9 (brs, 1H), 7.81-7.10 (m, 8H), 4.10 (t, J=6.4 Hz, 2H), 3.75-3.69 (m, 3H), 2.57-2.17 (m, 5H).

Reference Example 14

4-methyl-5-oxo-1-tosyl-2,3,4,5-tetrahydro-1H-benzo [b]azepine-4-carboxylic acid methyl ester (racemate)

5-oxo-1-tosyl-2,3,4,5-tetrahydro-1H-benzo[b]azepine-4-carboxylic acid methyl ester (100 mg) was dissolved into acetone (2 mL), thereto were added potassium carbonate (74.1 mg) and methyl iodide (33 μL), and the reaction mixture was heated to reflux for 1.5 hours. The reaction solution was added with water, extracted with ethyl acetate, then washed with saturated saline, and dried with anhydrous sodium sulfate. The reaction solution was concentrated with a reduced pressure, and the obtained residue was purified by column chromatography (hexane/ethyl acetate=4/1 to 2/1) to thus obtain the title compound (99.2 mg) as a white solid.

$^1$H-NMR (400 MHz, CDCl$_3$) δ7.55 (d, J=8.4 Hz, 2H), 7.46-7.31 (m, 4H), 7.28-7.21 (m, 2H), 4.08-3.99 (m, 1H), 3.87-3.77 (m, 1H), 3.61 (s, 3H), 2.47-2.31 (m, 4H), 1.89-1.78 (m, 1H), 1.31 (s, 3H).

ESI/MS (m/z) 388 (M+H)$^+$.

Herein, "racemate" is expressed to be a racemic compound in a quaternary carbon atom when the quaternary carbon atom is an asymmetric carbon, as shown in, for example, the formula described below;

[Formula 27]

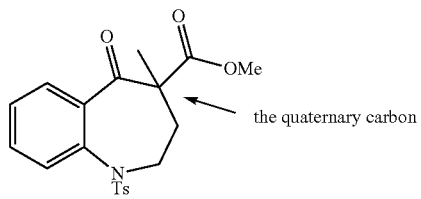

the quaternary carbon

In addition, the following compound obtained by using the above described compound and a raw material having a racemate in the quaternary carbon atom in the same manner is expressed by (racemate) in the end of its denomination.

Example 1

4-methyl-1-tosyl-2,3,4,5-tetrahydro-1H-benzo[b] azepine-4-carboxylic acid methyl ester (racemate)

4-methyl-5-oxo-1-tosyl-2,3,4,5-tetrahydro-1H-benzo[b] azepine-4-carboxylic acid methyl ester (racemate: 74.0 mg) was dissolved into methylene chloride (2 mL), thereto were added trifluoroacetic acid (29 μL), triethylsilane (120 μL), methanesulfonic acid (19 μL), and a boron trifluoride diethyl ether complex (36 μL) under an ice bath, and the reaction mixture was directly stirred at 30 minutes, and stirred at room temperature for 2 hours. The reaction solution was added with an aqueous saturated sodium hydrogen carbonate solution, extracted with ethyl acetate, then washed with water and saturated saline, and dried with anhydrous sodium sulfate. The reaction solution was concentrated with a reduced pressure, and the obtained residue was purified by column chromatography (hexane/ethyl acetate=9/1 to 1/1) to thus obtain the title compound (34.2 mg).

$^1$H-NMR (400 MHz, CDCl$_3$) δ7.62 (d, J=8.3 Hz, 2H), 7.33-7.06 (m, 6H), 4.14-3.37 (m, 5H), 2.69 (d, J=13.8 Hz, 1H), 2.53-2.37 (m, 4H), 2.21-2.09 (m, 1H) 1.83-1.54 (m, 1H), 1.12 (brs, 3H).

ESI/MS (m/z) 374 (M+H)$^+$.

Example 2

4-methyl-2,3,4,5,-tetrahydro-1H-benzo[b]azepine-4-carboxylic acid methyl ester (racemate)

4-methyl-1-tosyl-2,3,4,5-tetrahydro-1H-benzo[b] azepine-4-carboxylic acid methyl ester (racemate: 434 mg) was dissolved into methanol (12 mL), thereto was added magnesium (283 mg), and the reaction mixture was stirred at 60° C. for 30 minutes. The reaction solution was added with an aqueous saturated ammonium chloride solution and stirred at room temperature for 1 hour, and then extracted with ethyl acetate. The organic phase was washed with saturated saline and then dried with anhydrous sodium sulfate. After filtration, the filtrate was concentrated with a reduced pressure, and the obtained residue was purified by a silica gel chromatography (hexane/ethyl acetate=3/2) to thus obtain the title compound (255 mg) as a yellow oily substance.

$^1$H-NMR (400 MHz, CDCl$_3$) δ7.09 (dd, J=7.4, 1.6 Hz, 1H), 7.04 (td, J=7.4, 1.6 Hz, 1H), 6.81 (td, J=7.4, 1.2 Hz, 1H), 6.67 (dd, J=7.4, 1.2 Hz, 1H), 3.71 (brs, 1H), 3.62 (s, 3H), 3.18-3.05 (m, 3H), 2.79 (d, J=13.7 Hz, 1H), 2.26 (dddd, J=13.9, 7.0, 2.6, 1.1 Hz, 1H), 1.70 (ddd, J=13.9, 9.1, 3.2 Hz, 1H), 1.24 (s, 3H).

ESI/MS (m/z) 220 (M+H)$^+$.

Example 3

4-methyl-1-tosyl-2,3,4,5-tetrahydro-1H-benzo[b] azepine-4-carboxylic acid (racemate)

4-methyl-1-tosyl-2,3,4,5-tetrahydro-1H-benzo[b] azepine-4-carboxylic acid methyl ester (racemate: 4.82 g) was dissolved into a mixed solvent of tetrahydrofuran (35 mL) and methanol (35 mL), thereto was added 1 M sodium hydroxide (37 mL), and the reaction mixture was stirred at 50° C. for 11 hours. The reaction solution was concentrated with a reduced pressure, and the obtained residue was added with water and extracted with ethyl acetate. The aqueous phase was added with 6 M hydrochloric acid to be acidified and then extracted with methylene chloride, and the organic phase was washed with saturated saline and then dried with anhydrous sodium sulfate. After filtration, the filtrate was concentrated with a reduced pressure to thus obtain the title compound (3.92 g) as a white solid.

$^1$H-NMR (400 MHz, CDCl$_3$) δ7.62 (d, J=8.3 Hz, 2H), 7.27-7.12 (m, 6H), 3.98-3.49 (m, 2H), 2.71 (d, J=14.0 Hz, 1H), 2.49 (d, J=14.0 Hz, 1H), 2.43 (s, 3H), 2.19-2.13 (m, 1H), 1.78-1.71 (m, 1H), 1.16 (brs, 3H).

ESI/MS (m/z) 360 (M+H)$^+$, 358 (M−H)$^−$.

Reference Example 15

N—[(R)-2-hydroxy-1-phenylethyl]-4-methyl-1-tosyl-2,3,4,5-tetrahydro-1H-benzo[b]azepine-4-carboxamide (chiral A)

Reference Example 16

N—[(R)-2-hydroxy-1-phenylethyl]-4-methyl-1-tosyl-2,3,4,5-tetrahydro-1H-benzo[b]azepine-4-carboxamide (chiral B)

4-methyl-1-tosyl-2,3,4,5-tetrahydro-1H-benzo[b] azepine-4-carboxylic acid (racemate: 1.00 g) was dissolved into N,N-dimethylformamide (20 mL), thereto were added 1-hydroxybenzotriazole (563 mg), 1-ethyl-3-(3-dimethylaminopropyl)carbodiimide hydrochloride (800 mg) and (R)-(−)-2-phenylglycinol (572 mg), and the reaction mixture was stirred at room temperature for 3 hours. The reaction solution was added with water and extracted with ethyl acetate, and the organic phase was then washed with an aqueous saturated sodium hydrogen carbonate solution and saturated saline in sequence and then dried with anhydrous sodium sulfate. After filtration, the filtrate was concentrated with a reduced pressure, and the obtained residue was purified by silica gel chromatography (hexane/ethyl acetate=1/1) to thus obtain the title compounds [Reference Example 15 (chiral A): 526 mg and Reference Example 16 (chiral B): 629 mg] as colorless oily substances.

Reference Example 15 (chiral A)

$^1$H-NMR (400 MHz, CDCl$_3$) δ7.59 (d, J=8.3 Hz, 2H), 7.32-7.23 (m, 9H), 7.17 (td, J=7.4, 1.4 Hz, 1H), 7.09 (dd, J=7.4, 1.4 Hz, 1H), 6.96 (brs, 1H), 6.16 (d, J=6.9 Hz, 1H), 4.94-4.90 (m, 1H), 3.88-3.74 (m, 1H), 3.81 (dd, J=5.3, 5.3 Hz, 2H), 3.63-3.49 (m, 1H), 2.64 (d, J=14.3 Hz, 1H), 2.52 (d, J=14.3 Hz, 1H), 2.40 (s, 3H), 2.29-2.23 (m, 1H), 1.72-1.65 (m, 1H), 1.12 (brs, 3H).

ESI/MS (m/z) 479 (M+H)$^+$, 477 (M−H)$^−$.

Reference Example 16 (chiral B)

$^1$H-NMR (400 MHz, CDCl$_3$) δ7.62 (d, J=8.3 Hz, 2H), 7.37-7.20 (m, 9H), 7.17 (d, J=8.0 Hz, 2H), 7.12 (dd, J=7.0, 1.8 Hz, 1H), 6.16 (d, J=6.9 Hz, 1H), 4.96-4.92 (m, 1H), 3.78-3.74 (m, 4H), 2.64 (d, J=14.1 Hz, 1H), 2.59-2.53 (m, 1H), 2.42 (s, 3H), 2.27-2.22 (m, 1H), 1.70-1.62 (m, 1H), 1.11 (brs, 3H).

ESI/MS (m/z) 479 (M+H)$^+$, 477 (M−H)$^−$.

Herein, "chiral A" is expressed to be an optically active highly polar isomer in a quaternary carbon atom when the quaternary carbon atom is an asymmetric carbon, as shown in, for example, the formula described below;

[Formula 28]

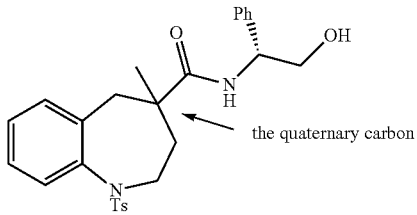

the quaternary carbon

In addition, the above described compound and the following compound obtained by using a raw material having an optically active highly polar isomer in the quaternary carbon atom in the same manner is expressed by (chiral A) in the end of its denomination.

Herein, "chiral B" is expressed to be an optically active low polar isomer in a quaternary carbon atom when the quaternary carbon atom is an asymmetric carbon, as shown in, for example, the formula described below;

[Formula 29]

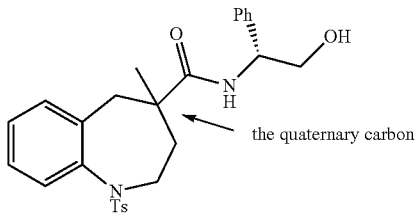

the quaternary carbon

In addition, the above described compound and the following compound obtained by using a raw material having an optically active low polar isomer in the quaternary carbon atom in the same manner is expressed by (chiral B) in the end of its denomination.

Example 4

4-methyl-1-tosyl-2,3,4,5-tetrahydro-1H-benzo[b] azepine-4-carboxylic acid methyl ester (chiral A)

N—[(R)-2-hydroxy-1-phenylethyl]-4-methyl-1-tosyl-2,3,4,5-tetrahydro-1H-benzo[b]azepine-4-carboxamide (chiral A: 526 mg) was dissolved into methanol (11 mL), thereto was added concentrated sulfuric acid (2.2 mL), and the reaction mixture was stirred at 80° C. for 11 hours. The reaction solution was concentrated with a reduced pressure, the obtained residue was added with water and extracted with ethyl acetate. The organic phase was washed with an aqueous saturated sodium hydrogen carbonate solution and saturated saline in sequence, and then dried with anhydrous sodium sulfate. After filtration, the filtrate was concentrated with a reduced pressure, and the obtained residue was purified by silica gel chromatography (hexane/ethyl acetate=2/1) to thus obtain the title compound (434 mg) as a colorless oily substance.

$^1$H-NMR (400 MHz, CDCl$_3$) δ7.62 (d, J=8.3 Hz, 2H), 7.28-7.25 (m, 2H), 7.23-7.14 (m, 3H), 7.12-7.08 (m, 1H), 4.00-3.87 (m, 1H), 3.64-3.48 (m, 1H), 3.53 (s, 3H), 2.69 (d, J=13.8 Hz, 1H), 2.47 (d, J=13.8 Hz, 1H), 2.43 (s, 3H), 2.18-2.13 (m, 1H), 1.76-1.70 (m, 1H), 1.12 (brs, 3H).
ESI/MS (m/z) 374 (M+H)$^+$.

Example 5

4-methyl-2,3,4,5,-tetrahydro-1H-benzo[b]azepine-4-carboxylic acid methyl ester (chiral A)

A reaction was carried out in the same method as Example 2 by using 4-methyl-1-tosyl-2,3,4,5-tetrahydro-1H-benzo[b]azepine-4-carboxylic acid methyl ester (chiral A) in place of 4-methyl-1-tosyl-2,3,4,5-tetrahydro-1H-benzo[b]azepine-4-carboxylic acid methyl ester (racemate) to thus obtain the title compound.
$^1$H-NMR (400 MHz, CDCl$_3$) δ7.09 (dd, J=7.4, 1.4 Hz, 1H), 7.04 (td, J=7.4, 1.4 Hz, 1H), 6.81 (td, J=7.4, 1.4 Hz, 1H), 6.67 (dd, J=7.4, 1.4 Hz, 1H), 3.71 (brs, 1H), 3.62 (s, 3H), 3.18-3.05 (m, 3H), 2.79 (d, J=13.7 Hz, 1H), 2.26 (dddd, J=13.9, 7.0, 2.6, 1.1 Hz, 1H), 1.70 (ddd, J=13.9, 9.1, 3.2 Hz, 1H), 1.24 (s, 3H).
ESI/MS (m/z) 220 (M+H)$^+$.

Reference Example 17

1-tosyl-2,3,4,5-tetrahydro-1H-benzo[b]azepine-4-carboxylic acid ethyl ester (racemate)

1-tosyl-2,3-dihydro-1H-benzo[b]azepine-4-carboxylic acid ethyl ester (631 mg) was dissolved into ethanol (8 mL), thereto was added palladium 10% on carbon (63.0 mg), and the reaction mixture was stirred under a hydrogen atmosphere at 50° C. for 14.5 hours. After the palladium on carbon was filtrated with celite, the filtrate was concentrated with a reduced pressure to thus obtain the title compound (634 mg) as a white solid.
$^1$H-NMR (400 MHz, CDCl$_3$) δ7.66-7.58 (m, 2H), 7.31-7.23 (m, 3H), 7.22-7.12 (m, 3H), 4.20-3.96 (m, 2H), 3.65-3.38 (m, 1H), 2.75-2.57 (m, 2H), 2.55-2.45 (m, 1H), 2.42 (s, 3H), 2.15-1.96 (m, 3H), 1.19 (t, J=7.1 Hz, 3H).

Example 6

4-fluoro-1-tosyl-2,3,4,5-tetrahydro-1H-benzo[b]azepine-4-carboxylic acid ethyl ester (racemate)

1-tosyl-2,3,4,5-tetrahydro-1H-benzo[b]azepine-4-carboxylic acid ethyl ester (racemate: 1.00 g) was dissolved into tetrahydrofuran (25 mL) and the reaction mixture was cooled to −78° C. Thereto was dropped a 2 M lithium diisopropylamide-tetrahydrofuran solution (1.7 mL) at −78° C., and the reaction solution was then stirred for 30 minutes. A tetrahydrofuran solution (10 mL) containing N-fluorobenzenesulfoneimide (1.27 g) was dropped to the reaction solution at the same temperature and the solution was stirred for 10 minutes, and the temperature was then increased to −40° C. and the reaction solution was further stirred for 10 minutes. The reaction solution was added with an aqueous saturated ammonium chloride solution and extracted with ethyl acetate. The organic phase was washed with water and saturated saline in sequence, and dried with anhydrous sodium sulfate. After filtration, the filtrate was concentrated with a reduced pressure, and the obtained residue was purified by silica gel column chromatography (ethyl acetate/hexane=1/6) to thus obtain the title compound (936 mg) as a white solid.
$^1$H-NMR (400 MHz, CDCl$_3$) δ7.66-7.61 (m, 2H), 7.31-7.19 (m, 5H), 7.16-7.11 (m, 1H), 4.25-4.16 (m, 2H), 3.63-3.41 (m, 1H), 3.01-2.80 (m, 2H), 2.56-2.37 (m, 4H), 2.15-2.03 (m, 2H), 1.30-1.25 (m, 3H).
ESI/MS (m/z) 392 (M+H)$^+$.

Example 7

4-fluoro-2,3,4,5-tetrahydro-1H-benzo[b]azepine-4-carboxylic acid methyl ester (racemate)

A reaction was carried out in the same method as Example 2 by using 4-fluoro-1-tosyl-2,3,4,5-tetrahydro-1H-benzo[b]azepine-4-carboxylic acid ethyl ester (racemate) in place of 4-methyl-1-tosyl-2,3,4,5-tetrahydro-1H-benzo[b]azepine-4-carboxylic acid methyl ester (racemate) to thus obtain the title compound.
$^1$H-NMR (400 MHz, CDCl$_3$) δ7.65-7.60 (m, 2H), 6.88 (td, J=7.9, 1.2 Hz, 1H), 6.78 (dd, J=7.9, 1.2 Hz, 1H), 3.82 (s, 3H), 3.45-3.06 (m, 4H), 2.28-2.46 (m, 1H), 2.24-2.11 (m, 1H).
ESI/MS (m/z) 224 (M+H)$^+$.

Example 8

4-fluoro-1-tosyl-2,3,4,5-tetrahydro-1H-benzo[b]azepine-4-carboxylic acid (racemate)

A reaction was carried out in the same method as Example 3 by using 4-fluoro-1-tosyl-2,3,4,5-tetrahydro-1H-benzo[b]azepine-4-carboxylic acid ethyl ester (racemate) in place of 4-methyl-1-tosyl-2,3,4,5-tetrahydro-1H-benzo[b]azepine-4-carboxylic acid methyl ester (racemate) to thus obtain the title compound.
1H-NMR (400 MHz, CDCl$_3$) δ7.63 (d, J=8.3 Hz, 2H), 7.32-7.21 (m, 5H), 7.17-7.12 (m, 1H), 4.23 (d, J=13.7 Hz, 1H), 3.55-3.42 (m, 1H), 3.05-2.87 (m, 2H), 2.63-2.39 (m, 4H), 2.16-2.09 (m, 1H).
ESI/MS (m/z) 364 (M+H)$^+$.

Reference Example 18

4-fluoro-N—[(R)-2-hydroxy-1-phenylethyl]-1-tosyl-2,3,4,5-tetrahydro-1H-benzo[b]azepine-4-carboxamide (chiral A)

Reference Example 19

4-fluoro-N—[(R)-2-hydroxy-1-phenylethyl]-1-tosyl-2,3,4,5-tetrahydro-1H-benzo[b]azepine-4-carboxamide (chiral B)

Reactions were carried out in the same methods as Reference Examples 15 and 16 by using 4-fluoro-1-tosyl-2,3,4,5-tetrahydro-1H-benzo[b]azepine-4-carboxylic acid (racemate) in place of 4-methyl-1-tosyl-2,3,4,5-tetrahydro-1H-benzo[b]azepine-4-carboxylic acid (racemate) to thus obtain the title compounds [Reference Example 18 (chiral A) and Reference Example 19 (chiral B)].

Reference Example 18 (chiral A)

$^1$H-NMR (400 MHz, CDCl$_3$) δ7.59 (d, J=8.3 Hz, 2H), 7.46-7.17 (m, 10H), 7.07-7.02 (m, 1H), 7.01-6.94 (m, 1H), 5.07-5.01 (m, 1H), 4.35 (d, J=14.8 Hz, 1H), 3.92-3.86 (m, 2H), 3.48-3.36 (m, 1H), 2.91-2.73 (m, 1H), 2.69-2.47 (m, 3H), 2.39 (s, 3H), 2.08-1.92 (m, 1H).
ESI/MS (m/z) 483 (M+H)$^+$.

Reference Example 19 (chiral B)

¹H-NMR (400 MHz, CDCl₃) δ7.58 (d, J=8.3 Hz, 2H), 7.44 (dd, J=7.8, 1.4 Hz, 1H), 7.39-7.21 (m, 9H), 7.12 (dd, J=7.4, 1.5 Hz, 1H), 7.00-6.97 (m, 1H), 5.06-5.02 (m, 1H), 4.32 (dt, J=14.8, 4.0 Hz, 1H), 3.92-3.89 (m, 2H), 3.39 (dd, J=13.8, 13.8 Hz, 1H), 2.91-2.72 (m, 2H), 2.58-2.41 (m, 1H), 2.41 (s, 3H), 2.03 (dd, J=6.6, 5.8 Hz, 1H), 1.94-1.87 (m, 1H).
ESI/MS (m/z) 483 (M+H)⁺.

Example 9

4-fluoro-1-tosyl-2,3,4,5-tetrahydro-1H-benzo[b]azepine-4-carboxylic acid methyl ester (chiral A)

A reaction was carried out in the same method as Example 4 by using 4-fluoro-N—[(R)-2-hydroxy-1-phenylethyl]-1-tosyl-2,3,4,5-tetrahydro-1H-benzo[b]azepine-4-carboxamide (chiral A) in place of N—[(R)-2-hydroxy-1-phenylethyl]-4-methyl-1-tosyl-2,3,4,5-tetrahydro-1H-benzo[b]azepine-4-carboxamide (chiral A) to thus obtain the title compound.
¹H-NMR (400 MHz, CDCl₃) δ7.64 (d, J=8.3 Hz, 2H), 7.31-7.19 (m, 5H), 7.13 (dd, J=5.1, 2.5 Hz, 1H), 4.25-4.07 (m, 1H), 3.77 (s, 3H), 3.61-3.42 (m, 1H), 3.09-2.80 (m, 2H), 2.57-2.39 (m, 4H), 2.15-2.04 (m, 1H).
ESI/MS (m/z) 378 (M+H)⁺.

Example 10

4-fluoro-2,3,4,5-tetrahydro-1H-benzo[b]azepine-4-carboxylic acid methyl ester (chiral A)

A reaction was carried out in the same method as Example 2 by using 4-fluoro-1-tosyl-2,3,4,5-tetrahydro-1H-benzo[b]azepine-4-carboxylic acid methyl ester (chiral A) in place of 4-methyl-1-tosyl-2,3,4,5-tetrahydro-1H-benzo[b]azepine-4-carboxylic acid methyl ester (racemate) to thus obtain the title compound.
¹H-NMR (400 MHz, CDCl₃) δ7.65-7.60 (m, 2H), 6.88 (td, J=7.9, 1.2 Hz, 1H), 6.78 (dd, J=7.9, 1.2 Hz, 1H), 3.82 (s, 3H), 3.45-3.06 (m, 4H), 2.28-2.46 (m, 1H), 2.24-2.11 (m, 1H).
ESI/MS (m/z) 224 (M+H)⁺.

Example 11

4-methyl-1-tosyl-2,3,4,5-tetrahydro-1H-benzo[b]azepine-4-carboxylic acid ethyl ester (racemate)

A reaction was carried out in the same method as Example 6 by using methyl iodide in place of N-fluorobenzene sulfoneimide to thus obtain the title compound.
¹H-NMR (400 MHz, CDCl₃) δ7.62 (d, J=8.3 Hz, 2H), 7.31-7.08 (m, 6H), 4.08-3.86 (m, 3H), 3.71-3.41 (m, 1H), 2.67 (d, J=13.9 Hz, 1H), 2.52-2.39 (m, 4H), 2.21-2.10 (m, 1H), 1.82-1.63 (m, 1H), 1.21-1.02 (m, 6H).
ESI/MS (m/z) 388 (M+H)⁺.

Example 12

4-methyl-2,3,4,5-tetrahydro-1H-benzo[b]azepine-4-carboxylic acid ethyl ester (racemate)

A reaction was carried out in the same method as Example 2 by using 4-methyl-1-tosyl-2,3,4,5-tetrahydro-1H-benzo[b]azepine-4-carboxylic acid ethyl ester (racemate) in place of 4-methyl-1-tosyl-2,3,4,5-tetrahydro-1H-benzo[b]azepine-4-carboxylic acid methyl ester (racemate) to thus obtain the title compound.
¹H-NMR (400 MHz, CDCl₃) δ7.12-7.06 (m, 1H), 7.03 (td, J=7.5, 1.4 Hz, 1H), 6.81 (td, J=7.5, 1.4 Hz, 1H), 6.67 (dd, J=7.5, 1.4 Hz, 1H), 4.06 (q, J=7.2 Hz, 2H), 3.71 (brs, 1H), 3.20-3.63 (m, 3H), 2.79 (d, J=13.8 Hz, 1H), 2.31-2.22 (m, 1H), 1.74-1.64 (m, 1H), 1.24 (s, 3H), 1.19 (t, J=7.2 Hz, 3H).
ESI/MS (m/z) 234 (M+H)⁺.

Reference Example 20

1-(t-butoxycarbonyl)-2,3-dihydro-1H-benzo[b]azepine-4-carboxylic acid methyl ester 2,3-dihydro-1H-benzo[b]azepine-4-carboxylic acid methyl ester (114 g) was dissolved into tetrahydrofuran (1.2 L), thereto were added 4-dimethylaminopyridine (6.85 g) and di-t-butyl dicarbonate (490 g), and the reaction mixture was stirred at 80° C. for 5 hours. Then, the reaction solution was further added with 4-dimethylaminopyridine (68.5 g) and di-t-butyl dicarbonate (184 g), and stirred at 80° C. for 15 hours. The reaction solution was concentrated with a reduced pressure and added with ethyl acetate, and the organic phase was washed with an aqueous 20% citric acid solution, an aqueous saturated sodium hydrogen carbonate solution and a saturated saline in sequence, and dried with anhydrous sodium sulfate. After filtration, the residue obtained by concentrating the filtrate with a reduced pressure was purified by silica gel column chromatography (ethyl acetate/hexane=1/6) to thus obtain the title compound (141 g) as a light yellow solid.
¹H-NMR (400 MHz, CDCl₃) δ7.67 (s, 1H), 7.41-7.27 (m, 3H), 7.19 (t, J=8.0 Hz, 1H), 3.82 (s, 3M), 3.65 (s, 2H), 2.89 (t, J=4.0 Hz, 2H), 1.47 (s, 9H).
ESI/MS (m/z) 304 (M+H)⁺.

Reference Example 21

1-(t-butoxycarbonyl)-2,3,4,5-tetrahydro-1H-benzo[b]azepine-4-carboxylic acid methyl ester A reaction was carried out in the same method as Example 17 by using 1-(t-butoxycarbonyl)-2,3-dihydro-1H-benzo[b]azepine-4-carboxylic acid methyl ester in place of 1-tosyl-2,3-dihydro-1H-benzo[b]azepine-4-carboxylic acid ethyl ester to thus obtain the title compound.
¹H-NMR (400 MHz, CDCl₃) δ7.26-7.12 (m, 4H), 4.45-4.25 (m, 1H), 3.69 (s, 3H), 3.00-2.10 (m, 4H), 2.10-2.00 (m, 2H), 1.53-1.36 (m, 9H).
ESI/MS (m/z) 306 (M+H)⁺.

Example 13

1-(t-butoxycarbonyl)-4-ethyl-2,3,4,5-tetrahydro-1H-benzo[b]azepine-4-carboxylic acid methyl ester (racemate)

A reaction was carried out in the same method as Example 6 by using 1-(t-butoxycarbonyl)-2,3,4,5-tetrahydro-1H-benzo[b]azepine-4-carboxylic acid methyl ester in place of 1-tosyl-2,3,4,5-tetrahydro-1H-benzo[b]azepine-4-carboxylic acid ethyl ester and using ethyl iodide in place of N-fluorobenzene sulfoneimide to thus obtain the title compound.

¹H-NMR (400 MHz, CDCl₃) δ7.21-7.08 (m, 4H), 4.30 (s, 1H), 3.59 (s, 3H), 3.00-2.83 (m, 3H), 2.23-2.18 (m, 1H), 1.69-1.37 (m, 12H), 0.85 (t, J=8.0 Hz, 3H).
ESI/MS (m/z) 334 (M+H)⁺.

Example 14

1-(t-butoxycarbonyl)-4-ethyl-2,3,4,5-tetrahydro-1H-benzo[b]azepine-4-carboxylic acid (racemate)

A reaction was carried out in the same method as Example 3 by using 1-(t-butoxycarbonyl)-4-ethyl-2,3,4,5-tetrahydro-1H-benzo[b]azepine-4-carboxylic acid methyl ester (racemate) in place of 4-methyl-1-tosyl-2,3,4,5-tetrahydro-1H-benzo[b]azepine-4-carboxylic acid methyl ester (racemate) to thus obtain the title compound.
¹H-NMR (400 MHz, CDCl₃) δ7.26-7.10 (m, 4H), 4.29-2.83 (m, 4H), 2.20-2.16 (m, 1H), 1.68-1.37 (m, 12H), 0.91-0.87 (m, 3H).
ESI/MS (m/z) 320 (M+H)⁺, 318 (M−H)⁻.

Reference Example 22

4-ethyl-4-{[(R)-2-hydroxy-1-phenylethyl]carbamoyl}-2,3,4,5-tetrahydro-1H-benzo[b]azepine-1-carboxylic acid t-butyl ester (chiral A)

Reference Example 23

4-ethyl-4-{[(R)-2-hydroxy-1-phenylethyl]carbamoyl}-2,3,4,5-tetrahydro-1H-benzo[b]azepine-1-carboxylic acid t-butyl ester (chiral B)

Reactions were carried out in the same methods as Reference Examples 15 and 16 by using 1-(t-butoxycarbonyl)-4-ethyl-2,3,4,5-tetrahydro-1H-benzo[b]azepine-4-carboxylic acid (racemate) in place of 4-methyl-1-tosyl-2,3,4,5-tetrahydro-1H-benzo[b]azepine-4-carboxylic acid (racemate) to thus obtain the title compounds [Reference Example 22 (chiral A) and Reference Example 23 (chiral B)].

Reference Example 22 (chiral A)

¹H-NMR (400 MHz, CDCl₃) δ7.33-6.93 (m, 9H), 6.31 (s, 1H), 4.98 (s, 1H), 4.30-3.83 (m, 3H), 2.96-2.27 (m, 4H), 1.68-1.37 (m, 13H), 0.95-0.91 (m, 3H).
ESI/MS (m/z) 439 (M+H)⁺, 437 (M−H)⁻.

Reference Example 23 (chiral B)

¹H-NMR (400 MHz, CDCl₃) δ7.35-7.14 (m, 9H), 6.25 (brs, 1H), 4.97-4.94 (m, 1H), 4.36-4.23 (m, 1H), 3.77-3.70 (m, 2H), 3.00-2.95 (m, 2H), 2.38-2.20 (m, 2H), 1.71-1.53 (m, 3H), 1.37 (s, 9H), 0.86 (t, J=7.7 Hz, 3H).
ESI/MS (m/z) 439 (M+H)⁺, 437 (M−H)⁻.

Example 15

4-ethyl-2,3,4,5-tetrahydro-1H-benzo[b]azepine-4-carboxylic acid methyl ester (chiral A)

A reaction was carried out in the same method as Example 4 by using 4-ethyl-4-{[(R)-2-hydroxy-1-phenyl ethyl]carbamoyl}-2,3,4,5-tetrahydro-1H-benzo[b]azepine-1-carboxylic acid t-butyl ester (chiral A) in place of N—[(R)-2-hydroxy-1-phenylethyl]-4-methyl-1-tosyl-2,3,4,5-tetrahydro-1H-benzo[b]azepine-4-carboxamide (chiral A) to thus obtain the title compound.
¹H-NMR (400 MHz, CDCl₃) δ7.09 (d, J=8.0 Hz, 1H), 7.03 (t, J=8.0 Hz, 1H), 6.80 (t, J=8.0 Hz, 1H), 6.65 (d, J=8.0 Hz, 1H), 3.72 (brs, 1H), 3.61 (s, 3H), 3.22-2.83 (m, 4H), 2.28-2.22 (m, 1H), 1.76-1.51 (m, 3H), 0.85 (t, J=8.0 Hz, 3H).
ESI/MS (m/z) 234 (M+H)⁺.

Reference Example 24

(S)-3-cyano-2-methylpropyl methane sulfonic acid ester (R)-3-bromo-2-methyl-1-propanol (30.1 g) was dissolved into dimethyl sulfoxide (130 mL), thereto was added sodium cyanide (10.1 g), and the reaction mixture was stirred at 60° C. for 1.5 hours. The reaction solution was added with water and extracted with methylene chloride 4 times. The organic phase was washed with water and saturated saline in sequence, and then dried with anhydrous sodium sulfate. After filtration, the filtrate was concentrated with a reduced pressure to thus obtain (S)-4-hydroxy-3-methylbutanenitrile.
The above described (S)-4-hydroxy-3-methylbutanenitrile was dissolved into methylene chloride (400 mL), thereto were added triethylamine (44 mL) and methanesulfonyl chloride (18.4 mL) at 0° C., and the reaction mixture was then stirred at 0° C. for 30 minutes. The reaction solution was added with 1 M hydrochloric acid to be acidified, and then extracted with methylene chloride. The organic phase was washed with water and saturated saline in sequence, and then dried with anhydrous sodium sulfate. After filtration, the filtrate was concentrated with a reduced pressure to thus obtain the title compound (29.9 g) as a colorless oily substance.
¹H-NMR (400 MHz, CDCl₃) δ4.25 (dd, J=10.3, 4.7 Hz, 1H), 4.08 (dd, J=10.3, 7.5 Hz, 1H), 3.06 (s, 3H), 2.57-2.41 (m, 2H), 2.41-2.25 (m, 1H), 1.18 (d, J=6.9 Hz, 3H).

Reference Example 25

(S)—N-(3-cyano-2-methylpropyl)-N-(2-formylphenyl)-4-methylbenzenesulfonamide

N-(2-formylphenyl)-4-methylbenzenesulfonamide (33.0 g) and (S)-3-cyano-2-methylpropyl methane sulfonic acid ester (23.3 g) were dissolved into N,N-dimethylformamide (480 mL), thereto were added lithium bromide (15.6 g) and potassium carbonate (24.9 g), and the reaction mixture was stirred at 70° C. for 18 hours. The reaction solution was added with water and extracted with ethyl acetate. The organic phase was washed with water and saturated saline in sequence, and dried with anhydrous sodium sulfate. After filtration, the filtrate was concentrated with a reduced pressure, and the obtained residue was purified by silica gel column chromatography (hexane/ethyl acetate=3/1 to 1/2) to thus obtain the title compound (23.5 g) as a yellow oily substance.
¹H-NMR (400 MHz, CDCl₃) δ10.45-10.38 (m, 1H), 8.04 (dd, J=7.1, 2.3 Hz, 1H), 7.56-7.45 (m, 2H), 7.43-7.39 (m, 2H), 7.28 (d, J=8.3 Hz, 2H), 6.82-6.71 (m, 1H), 3.85-3.64 (m, 1H), 3.50-3.21 (m, 1H), 2.62-2.39 (m, 1H), 2.45 (s, 3H), 2.35 (dd, J=6.4, 2.4 Hz, 1H), 2.13-1.95 (m, 1H), 1.20-1.04 (m, 3H).
ESI/MS (m/z) 357 (M+H)⁺.

Reference Example 26

(S)-3-methyl-1-tosyl-2,3-dihydro-1H-benzo[b]azepine-4-carbonitrile (S)—N-(3-cyano-2-methylpropyl)-N-(2-formylphenyl)-4-m ethylbenzenesulfonamide (17.7 g) was dissolved into diethyl carbonate (830 mL), thereto was added a 20% sodium ethoxide-ethanol solution (24 mL), and the reaction mixture was stirred at room temperature for 4 hours. The reaction solution was diluted with water and extracted with ethyl acetate. The organic phase was washed with saturated saline and then dried with anhydrous sodium sulfate. After filtration, the residue obtained by concentrating the filtrate with a reduced pressure was purified by silica gel column chromatography (ethyl acetate/hexane=1/9 to 1/1) to thus obtain the title compound (9.00 g).

$^1$H-NMR (400 MHz, CDCl$_3$) δ7.65 (dd, J=8.0, 1.0 Hz, 1H), 7.46-7.33 (m, 1H), 7.42 (d, J=8.4 Hz, 2H), 7.29 (td, J=7.5, 1.0 Hz, 1H), 7.21-7.18 (m, 3H), 6.71 (d, J=1.8 Hz, 1H), 4.40 (dd, J=13.5, 4.2 Hz, 1H), 3.23-3.01 (m, 2H), 2.39 (s, 3H), 1.21 (d, J=6.6 Hz, 3H).

ESI/MS (m/z) 339 (M+H)$^+$, 337 (M−H)$^−$.

Reference Example 27

(S)-3-methyl-2,3-dihydro-1H-benzo[b]azepine-4-carboxylic acid methyl ester

A reaction was carried out in the same method as Reference Example 11 by using (S)-3-methyl-1-tosyl-2,3-dihydro-1H-benzo[b]azepine-4-carbo nitrile in place of 1-tosyl-2,3-dihydro-1H-benzo[b]azepine-4-carboxylic acid ethyl ester to thus obtain the title compound.

$^1$H-NMR (400 MHz, CDCl$_3$) δ7.62 (s, 1H), 7.27 (dd, J=7.8, 1.6 Hz, 1H), 7.11 (ddd, J=8.3, 7.2, 1.6 Hz, 1H), 6.73 (ddd, J=7.8, 7.2, 1.2 Hz, 1H), 6.69-6.61 (m, 1H), 4.57 (brs, 1H), 3.80 (s, 3H), 3.42-3.25 (m, 2H), 3.04 (d, J=12.8 Hz, 1H), 1.15 (d, J=6.8 Hz, 3H).

ESI/MS (m/z) 218 (M+H)$^+$.

Example 16

(3S)-1-(t-butoxycarbonyl)-3-methyl-2,3,4,5-tetrahydro-1H-benzo[b]azepine-4-carboxylic acid methyl ester (racemate)

(S)-3-methyl-2,3-dihydro-1H-benzo[b]azepine-4-carboxylic acid methyl ester (305 mg) was dissolved into tetrahydrofuran (3 mL), thereto were added di-t-butyl dicarbonate (1.1 mL) and 4-dimethylaminopyridine (305 mg), and the reaction mixture was heated to reflux for 17 hours. The reaction solution was diluted with water and extracted with ethyl acetate. The organic phase was washed with an aqueous saturated sodium hydrogen carbonate solution and saturated saline in sequence, and then dried with anhydrous sodium sulfate. After filtration, the residue obtained by concentrating the filtrate with a reduced pressure was purified by silica gel column chromatography (ethyl acetate/hexane=1/4 to 1/2) to thus obtain (3S)-1-(t-butoxycarbonyl)-3-methyl 2,3-dihydro-1H-benzo[b]azepine-4-carboxylic acid methyl ester.

The above described (3S)-1-(t-butoxycarbonyl)-3-methyl 2,3-dihydro-1H-benzo[b]azepine-4-carboxylic acid methyl ester was dissolved into ethanol (4 mL) and thereto was added palladium 10% on carbon (30.0 mg). After replacing the inside of the reaction container with hydrogen, the reaction solution was stirred at 50° C. for 4 hours. The reaction container was replaced with argon, and the reaction solution was then filtrated with celite and washed with ethyl acetate. The filtrate was added with water and separated, and the organic phase was then washed with saturated saline and dried with anhydrous sodium sulfate. After filtration, the filtrate was concentrated with a reduced pressure to thus obtain the title compound (251 mg).

$^1$H-NMR (400 MHz, CDCl$_3$) δ7.29-7.01 (m, 4H), 4.54-3.91 (m, 1H), 3.82-3.40 (m, 3H), 3.27-2.07 (m, 5H), 1.60-1.30 (m, 9H), 1.13-0.79 (m, 3H).

Example 17

(3S)-1-(t-butoxycarbonyl)-3,4-dimethyl-2,3,4,5-tetrahydro-1H-benzo[b]azepine-4-carboxylic acid methyl ester (racemate)

(3S)-1-(t-butoxycarbonyl)-3-methyl-2,3,4,5-tetrahydro-1H-benzo[b]azepine-4-carboxylic acid methyl ester (251 mg) was dissolved into tetrahydrofuran (5 mL) and cooled to −78° C. Thereto was dropped lithium diisopropylamide (1.8 M tetrahydrofuran solution) (870 μL) and the reaction mixture was stirred for 30 minutes. The reaction solution was added with methyl iodide (98 μL) and stirred at −40° C. for 1 hour. The reaction solution was diluted with water and extracted with ethyl acetate. The organic phase was washed with saturated saline and dried with anhydrous sodium sulfate. After filtration, the residue obtained by concentrating the filtrate with a reduced pressure was purified by silica gel column chromatography (ethyl acetate/hexane=1/10 to 1/4) to thus obtain the title compound (219 mg).

$^1$H-NMR (400 MHz, CDCl$_3$) δ7.25-7.04 (m, 4H), 4.22-4.04 (m, 1H), 3.74 (s, 3H), 3.23 (d, J=13.2 Hz, 1H), 2.71-2.35 (m, 3H), 1.60-1.31 (m, 9H), 0.85-0.69 (m, 3H).

Example 18

(3S)-3,4-dimethyl-2,3,4,5-tetrahydro-1H-benzo[b]azepine-4-carboxylic acid methyl ester (racemate)

(3S)-1-(t-butoxycarbonyl)-3,4-dimethyl-2,3,4,5-tetrahydro-1H-benzo[b]azepine-4-carboxylic acid methyl ester (racemate: 219 mg) was dissolved into methylene chloride (4.4 mL), thereto was added trifluoroacetic acid (730 μL), and the reaction mixture was stirred at room temperature for 1 hour. The reaction solution was cooled to 0° C. and diluted with methylene chloride and water. The mixed solution was added with 5 M sodium hydroxide to be neutralized, and then extracted with methylene chloride. The organic phase was washed with saturated saline, and then dried with anhydrous sodium sulfate. After filtration, the filtrate was concentrated with a reduced pressure to thus obtain the title compound (144 mg).

ESI/MS (m/z) 234 (M+H)$^+$.

Example 19

(3S)-3-methyl-2,3,4,5-tetrahydro-1H-benzo[b]azepine-4-carboxylic acid methyl ester (3S)-1-(t-butoxycarbonyl)-3-methyl-2,3,4,5-tetrahydro-1H-benzo[b]azepine-4-carboxylic acid methyl ester (racemate: 913 mg) was dissolved into methylene chloride (9 mL), thereto was added trifluoroacetic acid (3 mL), and the reaction mixture was stirred at room temperature for 1 hour. The reaction solution was cooled to 0° C. and diluted with methylene chloride and water. The mixed solution was added with 5 M sodium hydroxide to be neutralized, and then extracted with methylene chloride. The organic phase was washed with saturated saline, and then dried with anhydrous sodium sulfate. After filtration, the filtrate was concentrated with a reduced pressure to thus obtain the title compound (560 mg).
ESI/MS (m/z) 220 (M+H)$^+$.

Example 20

(3R)-4-fluoro-3-methyl-2,3,4,5-tetrahydro-1H-benzo[b]azepine-4-carboxylic acid methyl ester (racemate)

(3S)-1-(t-butoxycarbonyl)-3-methyl-2,3,4,5-tetrahydro-1H-benzo[b]azepine-4-carboxylic acid methyl ester (racemate: 571 mg) was dissolved into tetrahydrofuran (7 mL) and cooled to −78° C. Thereto was dropped a 2 M lithium diisopropylamide-tetrahydrofuran solution (1.8 mL) at −78° C. and then stirred for 30 minutes. A tetrahydrofuran solution (2 mL) containing N-fluorobenzenesulfonimide (1.13 g) was dropped to the reaction solution at the same temperature, the reaction solution was stirred for 10 minutes, and the temperature was then increased to −40° C., and the reaction solution was further stirred for 10 minutes. The reaction solution was added with an aqueous saturated ammonium chloride solution and extracted with ethyl acetate. The organic phase was washed with water and saturated saline in sequence, and dried with anhydrous sodium sulfate. After filtration, the filtrate was concentrated with a reduced pressure, and the obtained residue was purified by silica gel column chromatography (ethyl acetate/hexane=1/4) to thus obtain (3R)-1-(t-butoxycarbonyl)-4-fluoro-3-methyl-2,3,4,5-tetrahydro-1H-benzo[b]azepine-4-carboxylic acid methyl ester (racemate: 463 mg).

The above described (3R)-1-(t-butoxycarbonyl)-4-fluoro-3-methyl-2,3,4,5-tetrahydro-1H-benzo[b]azepine-4-carboxylic acid methyl ester (racemate: 456 mg) was dissolved into methylene chloride (5 mL), thereto was added trifluoroacetic acid (1.7 mL), and the reaction mixture was stirred at room temperature for 1 hour. The reaction solution was cooled to 0° C., and diluted with methylene chloride and water. The mixed solution was added with 5 M sodium hydroxide to be neutralized and then extracted with methylene chloride. The organic phase was washed with saturated saline, and then dried with anhydrous sodium sulfate. After filtration, the filtrate was concentrated with a reduced pressure to thus obtain the title compound (259 mg).
ESI/MS (m/z) 238 (M+H)$^+$.

Example 21

4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate)

2-methyl-4-(3-methyl-1H-pyrazol-1-yl)benzoic acid (507 mg) was suspended to thionyl chloride (5 mL), and the reaction solution was stirred at 50° C. for 30 minutes and then concentrated with a reduced pressure. The obtained residue was dissolved into methylene chloride (8 mL), thereto was added a methylene chloride solution (2 mL) containing 4-methyl-2,3,4,5-tetrahydro-1H-benzo[b]azepine-4-carboxylic acid methyl ester (racemate: 466 mg) and pyridine (430 µL), and the reaction mixture was then stirred at room temperature for 3 hours. The reaction solution was added with water and extracted with methylene chloride, and the organic phase was washed with an aqueous saturated sodium hydrogen carbonate solution and saturated saline in sequence, and dried with anhydrous sodium sulfate. After filtration, the filtrate was concentrated with a reduced pressure, and the obtained residue was purified by silica gel chromatography (hexane/ethyl acetate=2/1 to 1/1) to thus obtain the title compound (848 mg) as a yellow oily substance.
$^1$H-NMR (400 MHz, CDCl$_3$) δ7.84-7.42 (m, 2H), 7.16-5.56 (m, 6H), 6.27-6.19 (m, 1H), 4.85-4.61 (m, 1H), 3.79-3.44 (m, 4H), 3.13-2.80 (m, 3H), 2.53-2.29 (m, 6H), 1.99-1.93 (m, 1H), 1.43 (brs, 2H), 1.06 (brs, 1H).
ESI/MS (m/z) 418 (M+H)$^+$.

Example 22

4-methyl-1-[2-methyl-4-(3-methyl-1H-pyrazol-1-yl)benzoyl]-2,3,4,5-tetrahydro-1H-benzo[b]azepine-4-carboxylic acid (racemate)

4-methyl-1-[2-methyl-4-(3-methyl-1H-pyrazol-1-yl)benzoyl]-2 (3,4,5-tetrahydro-1H-benzo[b]azepine-4-carboxylic acid methyl ester (racemate: 848 mg) was dissolved into a mixed solvent of tetrahydrofuran (5 mL) and methanol (5 mL), thereto was added 5 M sodium hydroxide (2 mL) and the reaction mixture was stirred at 50° C. for 3.5 hours. The reaction solution was concentrated with a reduced pressure, and the obtained residue was added with water and extracted with ethyl acetate. The aqueous phase was added with 6 M hydrochloric acid to be acidified, and then extracted with methylene chloride, and the organic phase was washed with saturated saline and then dried with anhydrous sodium sulfate. After filtration, the filtrate was concentrated with a reduced pressure to thus obtain the title compound (819 mg) as a white solid.
$^1$H-NMR (400 MHz, CDCl$_3$) δ7.84-7.45 (m, 2H), 7.21-6.55 (m, 6H), 6.27-6.20 (m, 1H), 4.87-4.61 (m, 1H), 3.75-2.82 (m, 4H), 2.53-2.28 (m, 6H), 2.01-1.95 (m, 1H), 1.50 (brs, 2H), 1.10 (brs, 1H).
ESI/MS (m/z) 404 (M+H)$^+$, 402 (M−H)$^-$.

Example 23

N-(2-amino-2-oxoethyl)-N, 4-dimethyl-1-[2-methyl-4-(3-methyl-1H-pyrazol-1-yl)benzoyl]-2,3,4,5-tetrahydro-1H-benzo[b]azepine-4-carboxamide (racemate)

4-methyl-1-[2-methyl-4-(3-methyl-1H-pyrazol-1-yl)benzoyl]-2,3,4,5-tetrahydro-1H-benzo[b]azepine-4-carboxylic acid (racemate: 20.0 mg) was dissolved into methylene chloride (1.5 mL), thereto were added 1-hydroxybenzotriazole (13.4 mg), 1-ethyl-3-(3-dimethylaminopropyl) carbodiimide hydrochloride (19.0 mg), and N-methylglycinamide hydrochloride (12.4 mg), and the reaction mixture was stirred at room temperature for 17.5 hours. After the reaction solution was added with water and extracted with methylene chloride, the organic phase was washed with an aqueous saturated sodium hydrogen carbonate solution and saturated saline in sequence, and then dried with anhydrous sodium sulfate. After filtration, the filtrate was concentrated with a reduced pressure, and the obtained residue was purified by thin layer silica gel chromatography (chloroform/methanol=10/1) to thus obtain the title compound (2.00 mg) as a white solid.

$^1$H-NMR (400 MHz, CDCl$_3$) δ7.84-7.44 (m, 2H), 7.19-6.76 (m, 4H), 7.11 (dd, J=8.2, 2.0 Hz, 1H), 6.60 (d, J=7.4 Hz, 1H), 6.27-6.19 (m, 1H), 5.56 (brs, 1H), 5.33 (brs, 1H), 4.96-4.82 (m, 1H), 4.56-4.49 (m, 1H), 4.18-3.94 (m, 2H), 3.61-3.15 (m, 5H), 2.93-2.88 (m, 1H), 2.52-2.33 (m, 6H), 1.95-1.89 (m, 1H), 1.56 (brs, 2H), 1.26 (brs, 1H).

ESI/MS (m/z) 474 (M+H)$^+$, 472 (M−H)$^−$.

Compounds were synthesized according to the reaction formula described below in reference to the method of Example 21. The synthesized compounds and data were shown in Tables 1 and 2.

[Formula 30]

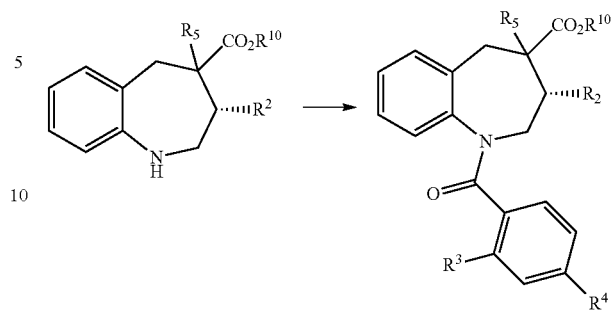

TABLE 1

| Example | Starting material | R$^2$ | R$^3$ | R$^4$ | R$^5$ | R$^{10}$ | ESI/MS(m/z) |
|---|---|---|---|---|---|---|---|
| 24 (chiral A) | Example 5 | H | Me | *–N-N pyrazole | Me | Me | 418(M + H)$^+$ |
| 25 (chiral A) | Example 5 | H | Me | *–N pyrrolidine | Me | Me | 407(M + H)$^+$ |
| 26 (racemate) | Example 12 | H | Me | *–N pyrrolidine (Me) | Me | Et | 435(M + H)$^+$ |
| 27 (racemate) | Example 12 | H | Me | *–N oxazole-Me | Me | Et | 433(M + H)$^+$ |
| 28 (chiral A) | Example 5 | H | Cl | *–N-N pyrazole | Me | Me | 438(M + H)$^+$ |
| 29 (racemate) | Example 12 | H | Cl | *–O-CH$_2$CH$_2$CH$_2$F | Me | Et | 448(M + H)$^+$ |
| 30 (chiral A) | Example 5 | H | Cl | *–O-CH$_2$CF$_3$ | Me | Me | 456(M + H)$^+$ |
| 31 (racemate) | Example 2 | H | Cl | *–N pyrrolidine | Me | Me | 427(M + H)$^+$ |
| 32 (racemate) | Example 2 | H | Cl | *–O-propyl | Me | Me | 416(M + H)$^+$ |
| 33 (racemate) | Example 2 | H | Cl | *–oxazole | Me | Me | 425(M + H)$^+$ |
| 34 (racemate) | Example 2 | H | Cl | *–N-N pyrazole | Me | Me | 424(M + H)$^+$ |

TABLE 1-continued

| Example | Starting material | R² | R³ | R⁴ | R⁵ | R¹⁰ | ESI/MS(m/z) |
|---|---|---|---|---|---|---|---|
| 35 (chiral A) | Example 5 | H | CF₃ | *-N-N= (3-methylpyrazol-1-yl) | Me | Me | 472(M + H)⁺ |
| 36 (chiral A) | Example 5 | H | CF₃ | *-N (pyrrolidin-1-yl) | Me | Me | 461(M + H)⁺ |
| 37 (chiral A) | Example 10 | H | Me | *-N-N= (3-methylpyrazol-1-yl) | F | Me | 422(M + H)⁺ |

TABLE 2

| Example | Starting material | R² | R³ | R⁴ | R⁵ | R¹⁰ | ESI/MS (m/z) |
|---|---|---|---|---|---|---|---|
| 38 (chiral A) | Example 10 | H | Me | *-N (pyrrolidinyl) | F | Me | 411 (M + H)⁺ |
| 39 (racemate) | Example 7 | H | Me | *-N (chiral pyrrolidinyl) | F | Me | 425 (M + H)⁺ |
| 40 (chiral A) | Example 15 | H | Me | *-N-N= (3-methylpyrazol-1-yl) | Et | Me | 432 (M + H)⁺ |
| 41 (racemate) | Example 18 | Me | Me | *-N-N= (3-methylpyrazol-1-yl) | Me | Me | 432 (M + H)⁺ |
| 42 (racemate) | Example 19 | Me | Cl | *-N (pyrrolidinyl) | H | Me | 427 (M + H)⁺ |
| 43 (racemate) | Example 20 | Me | Cl | *-N (pyrrolidinyl) | F | Me | 445 (M + H)⁺ |

Example 44

4-methyl-1-[2-methyl-4-(3-methyl-1H-pyrazol-1-yl)benzoyl]-2,3,4,5-tetrahydro-1H-benzo[b]azepine-4-carboxylic acid (chiral A)

A reaction was carried out in the same method as Example 22 by using 4-methyl-1-[2-methyl-4-(3-methyl-1H-pyrazol-1-yl)benzoyl]-2,3,4,5-tetrahydro-1H-benzo[b]azepine-4-carboxylic acid methyl ester (chiral A) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

¹H-NMR (400 MHz, CDCl₃) δ7.84-7.45 (m, 2H), 7.21-6.55 (m, 6H), 6.27-6.20 (m, 1H), 4.87-4.61 (m, 1H), 3.75-2.82 (m, 4H), 2.53-2.28 (m, 6H), 2.01-1.95 (m, 1H), 1.50 (brs, 2H), 1.10 (brs, 1H).
ESI/MS (m/z) 404 (M+H)⁺, 402 (M−H)⁻.

Example 45

4-methyl-1-[2-methyl-4-(pyrrolidine-1-yl)benzoyl]-2,3,4,5-tetrahydro-1H-benzo[b]azepine-4-carboxylic acid (chiral A)

A reaction was carried out in the same method as Example 22 by using 4-methyl-1-[2-methyl-4-(pyrrolidine-1-yl)benzoyl]-2,3,4,5-tetrahydro-1H-benzo[b]azepine-4-carboxylic acid methyl ester (chiral A) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.
ESI/MS (m/z) 393 (M+H)⁺, 391 (M−H)⁻.

Example 46

4-methyl-1-[2-methyl-4-(4-methyloxazol-2-yl)benzoyl]-2,3,4,5-tetrahydro-1H-benzo[b]azepine-4-carboxylic acid (racemate)

A reaction was carried out in the same method as Example 22 by using 4-methyl-1-[2-methyl-4(4-methyloxazol-2-yl)benzoyl]-2,3,4,5-tetrahydro-1H-benzo[b]azepine-4-carboxylic acid ethyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

¹H-NMR (400 MHz, CDCl₃) δ7.78 (s, 1H), 7.50-7.37 (m, 2H), 7.22-6.80 (m, 4H), 6.62-6.57 (m, 1H), 4.86-4.61 (m, 1H), 3.49-3.47 (m, 1H), 3.29-2.83 (m, 2H), 2.53 (s, 3H), 2.34-2.27 (m, 1H), 2.20 (d, J=1.2 Hz, 2H), 2.10 (s, 1H), 2.02-1.96 (m, 1H), 1.50 (brs, 2H), 1.10 (brs, 1H).
ESI/MS (m/z) 405 (M+H)⁺, 403 (M−H)⁻.

Example 47

1-[2-chloro-4-(3-methyl-1H-pyrazol-1-yl)benzoyl]-4-methyl-2,3,4,5-tetrahydro-1H-benzo[b]azepine-4-carboxylic acid (chiral A)

A reaction was carried out in the same method as Example 22 by using 1-[2-chloro-4-(3-methyl-1H-pyrazol-1-yl)benzoyl]-4-methyl-2,3,4,5-tetrahydro-1H-benzo[b]azepine-4-carboxylic acid methyl ester (chiral A) in place of 4-methyl-1-[2-methyl-4-(3-methyl-1H-pyrazol-1-yl)benzoyl]-2,3,4,5- tetrahydro-1H-benzo[b]azepine-4-carboxylic acid methyl ester (racemate) to thus obtain the title compound.

$^1$H-NMR (400 MHz, CDCl$_3$) δ7.84-7.70 (m, 1H), 7.64-7.60 (m, 1H), 7.52-6.83 (m, 6H), 6.30-6.21 (m, 1H), 4.80-4.59 (m, 1H), 3.51-2.77 (m, 3H), 2.47-1.95 (m, 5H), 1.62-1.07 (m, 3H).

ESI/MS (m/z) 424 (M+H)$^+$, 422 (M−H)$^−$.

Example 48

1-[2-chloro-4-(3-fluoropropoxy)benzoyl]-4-methyl-2,3,4,5-tetrahydro-1H-benzo[b]azepine-4-carboxylic acid (racemate)

A reaction was carried out in the same method as Example 22 by using 1-[2-chloro-4-(3-fluoropropoxy)benzoyl]-4-methyl-2,3,4,5-tetrahydro-1H-benzo[b]azepine-4-carboxylic acid ethyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

$^1$H-NMR (400 MHz, CDCl$_3$) δ7.38-6.78 (m, 6H), 6.54 (d, J=8.5 Hz, 1H), 4.83-4.51 (m, 3H), 4.16-3.97 (m, 2H), 3.76-3.48 (m, 1H), 3.28-2.77 (m, 2H), 2.44-2.21 (m, 1H), 2.13 (quin, J=5.9 Hz, 1H), 2.07 (quin, J=5.9 Hz, 1H), 2.02-1.95 (m, 1H), 1.47 (brs, 2H), 1.08 (brs, 1H).

ESI/MS (m/z) 420 (M+H)$^+$, 419 (M−H)$^−$.

Example 49

1-[2-chloro-4-(pyrrolidine-1-yl)benzoyl)-4-methyl-2,3,4,5-tetrahydro-1H-benzo[b]azepine-4-carboxylic acid (racemate)

A reaction was carried out in the same method as Example 22 by using 1-[2-chloro-4-(pyrrolidine-1-yl)benzoyl]-4-methyl-2,3,4,5-tetrahydro-1H-benzo[b]azepine-4-carboxylic acid methyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

$^1$H-NMR (400 MHz, CDCl$_3$) δ7.19 (d, J=7.3 Hz, 1H), 7.07-6.92 (m, 2H), 6.85-6.81 (m, 1H), 6.75 (d, J=8.5 Hz, 1H), 6.36 (d, J=2.3 Hz, 1H), 6.11 (dd, J=8.5, 2.3 Hz, 1H), 4.84-4.78 (m, 1H), 4.63-4.57 (m, 1H), 3.52-3.49 (m, 1H), 3.18-3.15 (m, 4H), 3.10-3.08 (m, 1H), 2.41-2.23 (m, 2H), 1.95 (ddd, J=6.6, 3.3, 3.3 Hz, 4H), 1.46 (brs, 2H), 1.09 (brs, 1H).

ESI/MS (m/z) 413 (M+H)$^+$, 411 (M−H)$^−$.

Example 50

1-(2-chloro-4-propoxybenzoyl)-4-methyl-2,3,4,5-tetrahydro-1H-benzo[b]azepine-4-carboxylic acid (racemate)

A reaction was carried out in the same method as Example 22 by using 1-(2-chloro-4-propoxybenzoyl)-4-methyl-2,3,4,5-tetrahydro-1H-benzo[b]azepine-4-carboxylic acid methyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

$^1$H-NMR (400 MHz, CDCl$_3$) δ7.20 (d, J=7.5 Hz, 1H), 7.13-6.81 (m, 4H), 6.77 (d, J=2.5 Hz, 1H), 6.53 (dd, J=8.5, 2.5 Hz, 1H), 4.82-4.58 (m, 1H), 3.80 (t, J=6.6 Hz, 2H), 3.50 (d, J=13.7 Hz, 1H), 3.27-3.04 (m, 2H), 2.45-2.24 (m, 1H), 2.02-1.94 (m, 1H), 1.73 (sext, J=7.2 Hz, 2H), 1.47 (brs, 2H), 1.08 (brs, 1H), 0.98 (t, J=7.2 Hz, 3H).

ESI/MS (m/z) 402 (M+H)$^+$, 400 (M−H)$^−$.

Example 51

1-[2-chloro-4-(oxazol-2-yl)benzoyl]-4-methyl-2,3,4,5-tetrahydro-1H-benzo[b]azepine-4-carboxylic acid (racemate)

A reaction was carried out in the same method as Example 22 by using 1-[2-chloro-4-(oxazol-2-yl)benzoyl]-4-methyl-2,3,4,5-tetrahydro-1H-benzo[b]azepine-4-carboxylic acid methyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

$^1$H-NMR (400 MHz, CDCl$_3$) δ7.95 (brs, 1H), 7.71-7.68 (m, 1H), 7.68 (s, 1H), 7.22 (s, 1H), 7.22-7.00 (m, 3H), 6.98-6.89 (m, 2H), 4.83-4.62 (m, 1H), 3.54-3.50 (m, 1H), 3.31-3.08 (m, 2H), 2.49-2.29 (m, 1H), 2.06-1.98 (m, 1H), 1.49 (brs, 2H), 1.09 (brs, 1H).

ESI/MS (m/z) 411 (M+H)$^+$, 409 (M−H)$^−$.

Example 52

1-[2-chloro-4-(1H-pyrazol-1-yl)benzoyl]-4-methyl-2,3,4,5-tetrahydro-1H-benzo[b]azepine-4-carboxylic acid (racemate)

A reaction was carried out in the same method as Example 22 by using 1-[2-chloro-4-(1H-pyrazol-1-yl)benzoyl]-4-methyl-2,3,4,5-tetrahydro-1H-benzo[b]azepine-4-carboxylic acid methyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

$^1$H-NMR (400 MHz, CDCl$_3$) δ7.83 (d, J=2.5 Hz, 1H), 7.68 (d, J=1.7 Hz, 1H), 7.67-7.65 (m, 1H), 7.38-7.34 (m, 1H), 7.21-6.86 (m, 5H), 6.44 (dd, J=2.5, 1.7 Hz, 1), 4.84-4.61 (m, 1H), 3.53-3.50 (m, 1H), 3.32-3.07 (m, 2H), 2.48-2.24 (m, 1H), 2.05-1.98 (m, 1H), 1.49 (brs, 2H), 1.09 (brs, 1H).

ESI/MS (m/z) 410 (M+H)$^+$, 408 (M−H)$^−$.

Example 53

4-methyl-1-[4-(3-methyl-1H-pyrazol-1-yl)-2-(trifluoromethyl)benzoyl]-2,3,4,5-tetrahydro-1H-benzo[b]azepine-4-carboxylic acid (chiral A)

A reaction was carried out in the same method as Example 22 by using 4-methyl-1-[4-(3-methyl-1H-pyrazol-1-yl)-2-(trifluoromethyl)benzoyl]-2,3,4,5-tetrahydro-1H-benzo[b]azepine-4-carboxylic acid methyl ester (chiral A) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (chiral A) to thus obtain the title compound.

$^1$H-NMR (400 MHz, CDCl$_3$) δ8.07-7.90 (m, 1H), 7.76-7.75 (m, 1H), 7.61-7.48 (m, 1H), 7.37-6.87 (m, 4H), 6.79-6.72 (m, 1H), 6.33-6.24 (m, 1H), 4.81-4.60 (m, 1H), 3.47-2.82 (m, 3H), 2.39-1.97 (m, 5H), 1.64-1.09 (m, 3H).

ESI/MS (m/z) 458 (M+H)$^+$, 456 (M−H)$^−$.

Example 54

4-fluoro-1-[2-methyl-4-(pyrrolidine-1-yl)benzoyl]-2,3,4,5-tetrahydro-1H-benzo[b]azepine-4-carboxylic acid (chiral A)

A reaction was carried out in the same method as Example 22 by using 4-fluoro-1-[2-methyl-4-(pyrrolidine-1-yl)benzoyl]-2,3,4,5-tetrahydro-1H-benzo[b]azepine-4-carboxylic acid methyl ester (chiral A) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

$^1$H-NMR (400 MHz, CDCl$_3$) δ7.24-7.16 (m, 1H), 7.14-6.94 (m, 2H), 6.76-6.47 (m, 2H), 6.37-6.23 (m, 1H), 6.09-5.94 (m, 1H), 5.03-4.82 (m, 1H), 3.78-2.86 (m, 7H), 2.71-2.38 (m, 4H), 2.29-2.13 (m, 1H), 2.09-1.84 (m, 4H).

ESI/MS (m/z) 397 (M+H)$^+$.

Example 55

(3S)-3,4-dimethyl-1-[2-methyl-4-(3-methyl-1H-pyrazol-1-yl)benzoyl]-2,3,4,5-tetrahydro-1H-benzo[b]azepine-4-carboxylic acid (racemate)

A reaction was carried out in the same method as Example 22 by using (3S)-3,4-dimethyl-1-[2-methyl-4-(3-methyl-1H-pyrazol-1-yl)benzoyl]-2,3,4,5-tetrahydro-1H-benzo[b]azepine-4-carboxylic acid methyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

ESI/MS (m/z) 418 (M+H)$^+$, 416 (M−H)$^−$.

Example 56

(3S)-1-[2-chloro-4-(pyrrolidine-1-yl)benzoyl]-3-methyl-2,3,4,5-tetrahydro-1H-benzo[b]azepine-4-carboxylic acid (racemate)

A reaction was carried out in the same method as Example 22 by using (3S)-1-[2-chloro-4-(pyrrolidine-1-yl)benzoyl]-3-methyl-2,3,4,5-tetrahydro-1H-benzo[b]azepine-4-carboxylic acid methyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

$^1$H-NMR (400 MHz, CDCl$_3$) δ7.18 (d, J=7.3 Hz, 1H), 7.08-6.93 (m, 2H), 6.90-6.72 (m, 2H), 6.38-6.36 (m, 1H), 6.15-6.09 (m, 1H), 6.15-6.09 (m, 1H), 4.96 (d, J=12.0 Hz, 1H), 3.40-3.29 (m, 1H), 3.18-3.15 (m, 4H), 2.96-2.90 (m, 1H), 2.50-2.42 (m, 2H), 2.23-2.17 (m, 1H), 1.97-1.93 (m, 4H), 1.17-1.04 (m, 3H).

ESI/MS (m/z) 413 (M+H)$^+$, 411 (M−H)$^−$.

Example 57

(3R)-1-[2-chloro-4-(pyrrolidine-1-yl)benzoyl]-4-fluoro-3-methyl-2,3,4,5-tetrahydro-1H-benzo[b]azepine-4-carboxylic acid (racemate)

A reaction was carried out in the same method as Example 22 by using (3R)-1-[2-chloro-4-(pyrrolidine-1-yl)benzoyl]-4-fluoro-3-methyl-2,3,4,5-tetrahydro-1H-benzo[b]azepine-4-carboxylic acid methyl ester (racemate) in place of 4-methyl-1-[2-methyl-4-(3-methyl-1H-pyrazol-1-yl)benzoyl]-2,3,4,5-tetrahydro-1H-benzo[b]azepine-4-carboxylic acid methyl ester (racemate) to thus obtain the title compound.

$^1$H-NMR (400 MHz, CDCl$_3$) δ7.14 (d, J=7.0 Hz, 1H), 7.09-7.02 (m, 2H), 6.88 (d, J=7.3 Hz, 1H), 6.76 (d, J=8.4 Hz, 1H), 6.35 (d, J=2.2 Hz, 1H), 6.12 (dd, J=8.4, 2.2 Hz, 1H), 4.81-4.77 (m, 1H), 3.71 (dd, J=44.3, 14.7 Hz, 1H), 3.20-3.14 (m, 5H), 2.89-2.74 (m, 2H), 1.95 (ddd, J=6.7, 3.6, 3.6 Hz, 4H), 1.06 (d, J=6.2 Hz, 3H).

ESI/MS (m/z) 431 (M+H)$^+$, 429 (M−H)$^−$.

Compounds were synthesized according to the reaction formula described below in reference to the method of Example 22. The synthesized compounds and data were shown in Table 3.

[Formula 31]

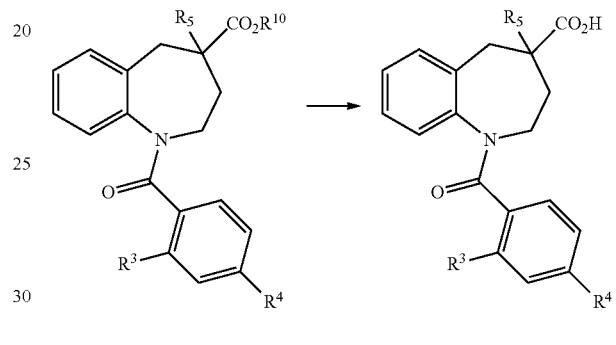

TABLE 3

| Example | Starting material | R$^3$ | R$^4$ | R$^5$ | R$^{10}$ | ESI/MS (m/z) |
|---|---|---|---|---|---|---|
| 58 (racemate) | Example 26 | Me | *—N⟨pyrrolidinyl⟩ | Me | Et | 407 (M + H)$^+$ 405 (M − H)$^−$ |
| 59 (chiral A) | Example 30 | Cl | *—O—CH$_2$—CF$_3$ | Me | Me | 442 (M + H)$^+$ 440 (M − H)$^−$ |
| 60 (chiral A) | Example 36 | CF$_3$ | *—N⟨pyrrolidinyl⟩ | Me | Me | 447 (M + H)$^+$ 445 (M − H)$^−$ |
| 61 (chiral A) | Example 37 | Me | *—N⟨pyrazolyl⟩ | F | Me | 408 (M + H)$^+$ 410 (M − H)$^−$ |
| 62 (racemate) | Example 39 | Me | *—N⟨pyrrolidinyl⟩ | F | Me | 411 (M + H)$^+$ 409 (M − H)$^−$ |
| 63 (chiral A) | Example 40 | Me | *—N⟨pyrazolyl⟩ | Et | Me | 418 (M + H)$^+$ 416 (M − H)$^−$ |

Compounds were synthesized according to the reaction formula described below in reference to the method of Example 23. The synthesized compounds were shown in Tables 4 to 6 and data was shown in Tables 7 to 9.

[Formula 32]

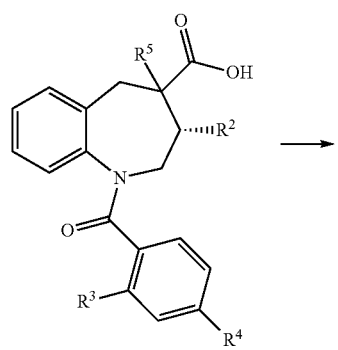 → 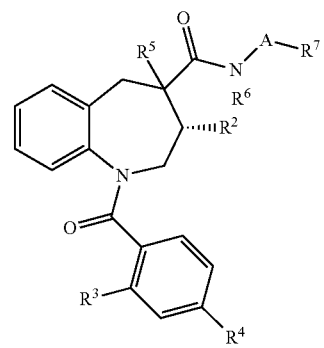

TABLE 4

| Example | Starting material | R² | R³ | R⁴ | *–N(R⁶)–A–R⁷ | R⁵ |
|---|---|---|---|---|---|---|
| 64 (racemate) | Example 22 | H | Me | *-pyrazol-1-yl (3-Me) | 2-oxopyrrolidin-3-ylamino | Me |
| 65 (chiral A) | Example 44 | H | Me | *-pyrazol-1-yl (3-Me) | *-NH-CH₂-(5-methyl-1,3,4-oxadiazol-2-yl) | Me |
| 66 (chiral A) | Example 44 | H | Me | *-pyrazol-1-yl (3-Me) | *-NH₂ | Me |
| 67 (chiral A) | Example 44 | H | Me | *-pyrazol-1-yl (3-Me) | *-NH-CH(Me)-CH₂OH | Me |
| 68 (chiral A) | Example 45 | H | Me | *-pyrrolidin-1-yl | *-NH-CH(Me)-C(O)NH₂ | Me |
| 69 (racemate) | Example 58 | H | Me | *-(3-methyl)pyrrolidin-1-yl | *-NH-CH₂-C(O)NH₂ | Me |
| 70 (racemate) | Example 58 | H | Me | *-(3-methyl)pyrrolidin-1-yl | *-NH-CH(Me)-CH₂OH | Me |
| 71 (racemate) | Example 46 | H | Me | *-(4-methyl-oxazol-2-yl) | *-NH-CH(Me)-C(O)NH₂ | Me |
| 72 (chiral A) | Example 47 | H | Cl | *-pyrazol-1-yl (3-Me) | *-NH-CH(Me)-CH₂OH | Me |

TABLE 4-continued

| Example | Starting material | R² | R³ | R⁴ | R⁵ | *—N(A-R⁷)(R⁶) |
|---|---|---|---|---|---|---|
| 73 (racemate) | Example 48 | H | Cl | *—O—CH₂CH₂CH₂F | Me | *—NH—CH(iPr)—C(=O)NH₂ (valine amide) |
| 74 (racemate) | Example 48 | H | Cl | *—O—CH₂CH₂CH₂F | Me | *—NH—C(CH₃)₂—C(=O)NH₂ |
| 75 (chiral A) | Example 59 | H | Cl | *—O—CH₂CF₃ | Me | *—NH₂ |
| 76 (chiral A) | Example 59 | H | Cl | *—O—CH₂CF₃ | Me | *—NH—CH(CH₃)—C(=O)NH₂ (alanine amide) |

TABLE 5

| Example | Starting material | R² | R³ | R⁴ | R⁵ | *—N(A-R⁷)(R⁶) |
|---|---|---|---|---|---|---|
| 77 (chiral A) | Example 59 | H | Cl | *—O—CH₂CF₃ | Me | *—NH—CH(CH₃)—CH₂OH |
| 78 (racemate) | Example 49 | H | Cl | *—N(pyrrolidinyl) | Me | *—NH—CH₂CH₂CH₃ |
| 79 (racemate) | Example 49 | H | Cl | *—N(pyrrolidinyl) | Me | *—NH—(5-methyl-1,3,4-oxadiazol-2-yl) |
| 80 (racemate) | Example 49 | H | Cl | *—N(pyrrolidinyl) | Me | *—NH—CH₂—C(=O)—NHEt |
| 81 (racemate) | Example 49 | H | Cl | *—N(pyrrolidinyl) | Me | *—NH—CH₂—C(=O)—NEt₂ |
| 82 (racemate) | Example 49 | H | Cl | *—N(pyrrolidinyl) | Me | *—NH—CH₂—(1,3,4-oxadiazol-2-yl) |

TABLE 5-continued

| Example | Starting material | R² | R³ | R⁴ | R⁵ | *—N(R⁶)—A—R⁷ |
|---|---|---|---|---|---|---|
| 83 (racemate) | Example 50 | H | Cl | *—O—CH₂CH₂CH₃ (propoxy) | Me | *—NH—CH(Me)—CH₂OH |
| 84 (racemate) | Example 50 | H | Cl | *—O—CH₂CH₂CH₃ (propoxy) | Me | *—NH—CH₂—C(=O)NH₂ |
| 85 (racemate) | Example 51 | H | Cl | *—(oxazol-2-yl) | Me | *—NH—CH(Me)—CH₂OH |
| 86 (racemate) | Example 51 | H | Cl | *—(oxazol-2-yl) | Me | *—NH—CH₂—C(=O)NH₂ |
| 87 (racemate) | Example 52 | H | Cl | *—(pyrazol-1-yl) | Me | *—NH—CH(Me)—CH₂OH |
| 88 (racemate) | Example 52 | H | Cl | *—(pyrazol-1-yl) | Me | *—NH—CH₂—C(=O)NH₂ |
| 89 (chiral A) | Example 53 | H | CF₃ | *—(3-methylpyrazol-1-yl) | Me | *—NH—CH(Me)—CH₂OH |

TABLE 6

| Example | Starting material | R² | R³ | R⁴ | R⁵ | *—N(R⁶)—A—R⁷ |
|---|---|---|---|---|---|---|
| 90 (chiral A) | Example 60 | H | CF₃ | *—(pyrrolidin-1-yl) | Me | *—NH—CH(Me)—C(=O)NH₂ |
| 91 (chiral A) | Example 61 | H | Me | *—(3-methylpyrazol-1-yl) | F | *—NH—CH(Me)—C(=O)NH₂ |
| 92 (chiral A) | Example 54 | H | Me | *—(2,3-dihydropyrrol-1-yl) | F | *—NH—CH₂—C(=O)NH₂ |
| 93 (chiral A) | Example 54 | H | Me | *—(2,3-dihydropyrrol-1-yl) | F | *—NH—CH(Me)—CH₂OH |

TABLE 6-continued

| Example | Starting material | R² | R³ | R⁴ | R⁵ | *–N(A-R⁷)(R⁵)(R⁶) |
|---|---|---|---|---|---|---|
| 94 (racemate) | Example 62 | H | Me | 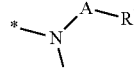 | F | *–NH₂ |
| 95 (racemate) | Example 62 | H | Me | 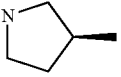 | F | 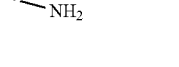 |
| 96 (chiral A) | Example 63 | H | Me | 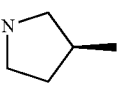 | Et | 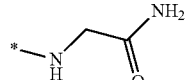 |
| 97 (racemate) | Example 55 | Me | Me | 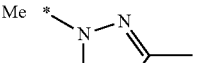 | Me | 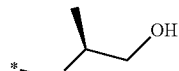 |
| 98 (racemate) | Example 56 | Me | Cl | 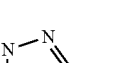 | H | 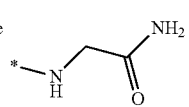 |
| 99 (racemate) | Example 56 | Me | Cl |  | H |  |
| 100 (racemate) | Example 57 | Me | Cl | 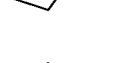 | F | 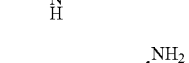 |
| 101 (racemate) | Example 57 | Me | Cl | 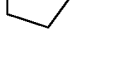 | F | 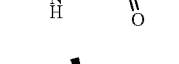 |

TABLE 7

| Example | ¹H-NMR (400 MHz, CDCl₃)δ | ESI/MS (m/z) |
|---|---|---|
| 64 (racemate) | 7.84-7.45 (m, 2H), 7.17-6.75 (m, 4H), 6.61-6.39 (m, 2H), 6.27-6.19 (m, 1H), 5.78 (brs, 1H), 5.67 (d, J = 7.9 Hz, 1H), 4.80-4.70 (m, 1H), 4.39-3.99 (m, 2H), 3.53-3.03 (m, 4H), 2.93-2.64 (m, 2H), 2.54-2.33 (m, 6H), 2.02-1.89 (m, 1H), 1.74-1.63 (m, 1H), 1.45 (d, J = 5.7 Hz, 1H), 1.08 (d, J = 5.7 Hz, 2H). | 486 (M + H)⁺ 484 (M − H)⁻ |
| 65 (chiral A) | 7.84-7.45 (m, 2H), 7.16-6.74 (m, 5H), 6.62-6.57 (m, 1H), 6.27 (brs, 1H), 6.19 (d, J = 2.4 Hz, 1H), 4.82-4.45 (m, 3H), 3.55-2.81 (m, 3H), 2.63-2.39 (m, 6H), 2.33 (s, 3H), 2.00-1.94 (m, 1H), 1.70-1.65 (m, 1H), 1.46 (brs, 1H), 1.10 (brs, 2H). | 499 (M + H)⁺ 497 (M − H)⁻ |
| 66 (chiral A) | 7.84-7.70 (m, 1H), 7.63-7.45 (m, 2H), 7.20-7.01 (m, 3H), 6.91-6.76 (m, 2H), 6.60 (d, J = 6.6 Hz, 1H), 6.27-6.19 (m, 1H), 5.84-5.48 (m, 2H), 4.79-4.73 (m, 1H), 3.57-3.40 (m, 1H), 3.26-2.80 (m, 2H), 2.54-2.33 (m, 6H), 2.27-1.94 (m, 1H), 1.68-1.60 (m, 1H), 1.45 (brs, 1H), 1.07 (brs, 2H). | 403 (M + H)⁺ |
| 67 (chiral A) | 7.84-7.45 (m, 2H), 7.20-7.10 (m, 1H), 7.03 (t, J = 7.7 Hz, 1H), 6.92-6.75 (m, 2H), 6.61 (dd, J = 7.8, 0.9 Hz, 1H), 6.27-6.19 (m, 1H), 5.93-5.91 (m, 1H), 5.64-5.63 (m, 1H), 4.82-4.74 (m, 1H), 4.18-3.58 (m, 3H), 3.49-3.14 (m, 3H), 2.99 (d, J = 13.5 Hz, 1H), 2.82 (d, J = 13.5 Hz, 1H), 2.54-2.33 (m, 6H), 2.06-1.63 (m, 2H), 1.43 (brs, 1H), 1.25-1.05 (m, 3H). | 461 (M + H)⁺ 459 (M − H)⁻ |
| 68 (chiral A) | 7.18-7.13 (m, 1H), 7.05-6.91 (m, 2H), 6.64-6.51 (m, 2H), 6.25-5.97 (m, 3H), 5.71 (brs, 1H), 5.41-5.13 (m, 1H), 4.76 (brs, 1H), 4.55-4.35 (m, 1H), 3.49-3.01 (m, 6H), 2.83-2.77 (m, 1H), 2.40 (s, 3H), 2.40-2.23 (m, 1H), 1.95-1.92 (m, 4H), 1.58-1.56 (m, 1H), 1.43 (brs, 3H), 1.30 (brs, 1H), 1.07 (brs, 2H). | 463 (M + H)⁺ 461 (M − H)⁻ |
| 69 (racemate) | 7.82-6.41 (m, 5H), 6.28-6.07 (m, 1H), 6.02-5.40 (m, 2H), 4.86-4.50 (m, 1H), 4.32-2.99 (m, 10H), 2.86-2.65 (m, 1H), 2.51-1.69 (m, 7H), 1.65-0.79 (m, 7H). | 463 (M + H)⁺ 461 (M − H)⁻ |

TABLE 7-continued

| Example | $^1$H-NMR (400 MHz, CDCl$_3$)δ | ESI/MS (m/z) |
|---|---|---|
| 70 (racemate) | 7.20-6.92 (m, 3H), 6.61-6.51 (m, 2H), 6.22 (s, 1H), 5.96-5.92 (m, 1H), 5.71-5.68 (m, 1H), 4.81-4.73 (m, 1H), 4.15-3.92 (m, 1H), 3.74-3.02 (m, 7H), 2.85-2.74 (m, 2H), 2.40 (s, 3H), 2.36-2.05 (m, 2H), 1.62-1.22 (m, 4H), 1.07 (d, J = 6.6 Hz, 3H), 1.07 (d, J = 6.6 Hz, 3H). | 464 (M + H)$^+$ 462 (M − H)$^−$ |
| 71 (racemate) | 7.78 (s, 1H), 7.49-7.35 (m, 2H), 7.21-6.60 (m, 5H), 6.38-5.29 (m, 3H), 4.84-4.32 (m, 2H), 3.55-3.45 (m, 1H), 3.24-2.73 (m, 2H), 2.54-2.20 (m, 7H), 1.95 (t, J = 12.1 Hz, 1H), 1.47-1.16 (m, 5H), 1.06 (brs, 1H). | 475 (M + H)$^+$ 473 (M − H)$^−$ |
| 72 (chiral A) | 7.84-7.59 (m, 2H), 7.46-6.85 (m, 6H), 6.30-6.22 (m, 1H), 6.03-5.70 (m, 1H), 4.77-4.73 (m, 1H), 4.15-2.73 (m, 7H), 2.84-1.88 (m, 5H), 1.64-1.03 (m, 6H). | 481 (M + H)$^+$ 479 (M − H)$^−$ |
| 73 (racemate) | 7.13-7.10 (m, 1H), 7.05 (t, J = 7.3 Hz, 1H), 6.97-6.84 (m, 3H), 6.78 (s, 1H), 6.54 (d, J = 7.3 Hz, 1H), 6.37-6.14 (m, 1H), 5.74-5.28 (m, 2H), 4.82-4.68 (m, 1H), 4.57 (dt, J = 47.0, 5.8 Hz, 2H), 4.35-4.19 (m, 1H), 3.99 (t, J = 5.8 Hz, 2H), 3.58-3.48 (m, 1H), 3.23-2.71 (m, 2H), 2.40-2.32 (m, 1H), 2.09 (dquin, J = 25.9, 5.8 Hz, 2H), 2.01-1.88 (m, 1H), 1.65-1.61 (m, 1H), 1.41-0.67 (m, 9H). | 518 (M + H)$^+$ 516 (M − H)$^−$ |
| 74 (racemate) | 7.17-6.78 (m, 5H), 6.55-6.15 (m, 2H), 5.88 (brs, 1H), 5.52-5.26 (m, 2H), 4.81-4.68 (m, 1H), 4.58 (dt, J = 47.0, 5.7 Hz, 2H), 4.38-4.11 (m, 1H), 3.98 (t, J = 5.7 Hz, 2H), 3.53-3.14 (m, 1H), 3.01-2.73 (m, 1H), 2.47-2.26 (m, 1H), 2.10 (dquin, J = 26.2, 5.7 Hz, 2H), 2.01-1.94 (m, 1H), 1.43 (brs, 1H), 1.31-1.26 (m, 2H), 1.06-0.83 (m, 6H). | 504 (M + H)$^+$ 502 (M − H)$^−$ |
| 75 (chiral A) | 7.58-6.79 (m, 6H), 6.68-6.53 (m, 1H), 5.90-5.14 (m, 2H), 4.84-4.65 (m, 1H), 4.46-4.19 (m, 2H), 3.67-2.72 (m, 3H), 2.51-0.80 (m, 5H). | 441 (M + H)$^+$ 439 (M − H)$^−$ |
| 76 (chiral A) | 7.58-6.72 (m, 6H), 6.65-5.99 (m, 2H), 5.74-5.06 (m, 2H), 4.83-4.17 (m, 4H), 3.63-2.64 (m, 3H), 2.51-1.87 (m, 2H), 1.70-0.78 (m, 6H). | 512 (M + H)$^+$ 510 (M − H)$^−$ |

TABLE 8

| Example | $^1$H-NMR (400 MHz, CDCl$_3$)δ | ESI/MS (m/z) |
|---|---|---|
| 77 (chiral A) | 7.57-6.77 (m, 6H), 6.65-6.52 (m, 1H), 6.05-5.59 (m, 1H), 4.83-4.65 (m, 1H), 4.45-3.87 (m, 3H), 3.81-1.85 (m, 8H), 1.70-0.81 (m, 6H). | 499 (M + H)$^+$ 497 (M − H)$^−$ |
| 78 (racemate) | 7.18-7.11 (m, 1H), 7.05-6.94 (m, 2H), 6.86-6.81 (m, 1H), 6.75 (d, J = 8.4 Hz, 1H), 6.36 (brs, 1H), 6.12-6.09 (m, 1H), 5.75-5.47 (m, 1H), 4.75-4.71 (m, 1H), 3.55-3.44 (m, 1H), 3.30-2.78 (m, 8H), 2.41-2.19 (m, 1H), 2.03-1.93 (m, 5H), 1.63-1.32 (m, 2H), 1.39 (brs, 2H), 1.02 (brs, 1H), 0.98-0.72 (m, 3H). | 454 (M + H)$^+$ |
| 79 (racemate) | 9.99 (brs, 1H), 7.19-7.14 (m, 1H), 7.08-6.92 (m, 2H), 6.86-6.74 (m, 2H), 6.37-6.35 (m, 1H), 6.13-6.07 (m, 1H), 4.82-4.66 (m, 1H), 3.64-3.53 (m, 1H), 3.29-3.15 (m, 5H), 2.90-2.82 (m, 1H), 2.54-2.39 (m, 4H), 2.04-1.94 (m, 5H), 1.44 (brs, 1H), 1.18 (brs, 2H). | 494 (M + H)$^+$ 492 (M − H)$^−$ |
| 80 (racemate) | 7.23-7.10 (m, 1H), 7.04-6.93 (m, 2H), 6.86-6.74 (m, 2H), 6.59-6.48 (m, 1H), 6.37-6.29 (m, 1H), 6.13-6.09 (m, 1H), 5.85-5.55 (m, 1H), 4.81-4.65 (m, 1H), 3.96-3.75 (m, 1H), 3.57-3.49 (m, 1H), 3.37-3.00 (m, 7H), 2.78-2.73 (m, 1H), 2.44-2.24 (m, 1H), 2.05-1.94 (m, 5H), 1.42 (brs, 1H), 1.28-1.05 (m, 5H). | 497 (M + H)$^+$ 495 (M − H)$^−$ |
| 81 (racemate) | 7.26-7.10 (m, 1H), 7.05-6.96 (m, 2H), 6.93-6.73 (m, 3H), 6.36 (brs, 1H), 6.13-6.09 (m, 1H), 4.78-4.63 (m, 1H), 4.10-3.83 (m, 2H), 3.55-2.75 (m, 1H), 2.46-2.25 (m, 1H), 2.05-1.93 (m, 5H), 1.42 (brs, 1H), 1.25-1.12 (m, 6H), 1.08 (brs, 2H). | 525 (M + H)$^+$ |
| 82 (racemate) | 8.42-8.26 (m, 1H), 7.18-7.12 (m, 1H), 7.07-6.94 (m, 2H), 6.86-6.81 (m, 1H), 6.74-6.72 (m, 1H), 6.36-6.31 (m, 2H), 6.13-6.08 (m, 1H), 4.79-4.51 (m, 3H), 3.53 (d, J = 13.0 Hz, 1H), 3.31-3.00 (m, 5H), 2.80 (d, J = 9.8 Hz, 1H), 2.46-2.25 (m, 1H), 2.05-1.93 (m, 5H), 1.44, (brs, 1H), 1.08 (brs, 2H). | 494 (M + H)$^+$ 492 (M − H)$^−$ |
| 83 (racemate) | 7.19-7.11 (m, 1H), 7.08-7.03 (m, 1H), 6.99-6.82 (m, 3H), 6.77 (d, J = 10.0 Hz, 1H), 6.54-6.51 (m, 1H), 5.92-5.63 (m, 1H), 4.78-4.71 (m, 1H), 4.17-3.93 (m, 1H), 3.80 (t, J = 6.6 Hz, 2H), 3.61-3.32 (m, 3H), 3.22-3.11 (m, 1H), 2.98-2.92 (m, 1H), 2.56-2.22 (m, 2H), 2.09-1.90 (m, 1H), 1.86-1.69 (m, 2H), 1.41 (brs, 2H), 1.25-1.11 (m, 3H), 1.03 (brs, 1H), 0.98 (t, J = 6.6 Hz, 3H). | 459 (M + H)$^+$ |
| 84 (racemate) | 7.23-7.19 (m, 1H), 7.13-6.76 (m, 5H), 6.67-6.35 (m, 2H), 5.95-5.28 (m, 2H), 4.79-4.66 (m, 1H), 4.02 (d, J = 4.8 Hz, 1H), 3.82-3.78 (m, 3H), 3.53 (d, J = 13.6 Hz, 1H), 3.21-3.01 (m, 2H), 2.47-2.26 (m, 1H), 2.00-1.94 (m, 2H), 1.86-1.69 (m, 2H), 1.43 (brs, 2H), 1.07 (brs, 1H), 0.98 (t, J = 7.4 Hz, 3H). | 458 (M + H)$^+$ 456 (M − H)$^−$ |
| 85 (racemate) | 7.95 (d, J = 10.0 Hz, 1H), 7.72-7.68 (m, 2H), 7.21 (d, J = 0.8 Hz, 1H), 7.20-7.03 (m, 3H), 6.97-6.90 (m, 2H), 5.94-5.62 (m, 1H), 4.80-4.73 (m, 1H), 4.18-3.74 (m, 2H), 3.63-3.15 (m, 3H), 2.99-2.79 (m, 1H), 2.52-2.18 (m, 2H), 2.01-1.94 (m, 1H), 1.42 (brs, 1H), 1.28-0.96 (m, 3H), 1.04 (brs, 2H). | 468 (M + H)$^+$ 466 (M − H)$^−$ |
| 86 (racemate) | 7.95 (d, J = 7.8 Hz, 1H), 7.70-7.66 (m, 2H), 7.21 (d, J = 0.8 Hz, 1H), 7.13-6.88 (m, 5H), 6.62-6.33 (m, 1H), 5.91-5.53 (m, 2H), 4.79-4.67 (m, 1H), 4.03 (d, J = 4.8 Hz, 1H), 3.80 (d, J = 4.8 Hz, 1H), 3.58 (d, J = 13.6 Hz, 1H), 3.29-2.74 (m, 2H), 2.50-2.30 (m, 1H), 2.03-1.96 (m, 1H), 1.43 (brs, 1H), 1.07 (brs, 2H). | 467 (M + H)$^+$ 465 (M − H)$^−$ |
| 87 (racemate) | 7.83 (d, J = 2.5 Hz, 1H), 7.69-7.65 (m, 2H), 7.39-7.33 (m, 1H), 7.20-7.03 (m, 3H), 6.98-6.87 (m, 2H), 6.44 (brs, 1H), 6.00-5.68 (m, 1H), 4.80-4.73 (m, 1H), 4.19-3.73 (m, 2H), 3.61-3.31 (m, 2H), 3.23-2.78 (m, 2H), 2.48-2.30 (m, 2H), 1.99-1.92 (m, 1H), 1.42 (brs, 1H), 1.25-0.96 (m, 3H), 1.04 (brs, 2H). | 467 (M + H)$^+$ 465 (M − H)$^−$ |
| 88 (racemate) | 7.83 (d, J = 2.5 Hz, 1H), 7.68-7.65 (m, 2H), 7.38-7.33 (m, 1H), 7.22-6.85 (m, 5H), 6.54-6.20 (m, 1H), 6.45-6.44 (m, 1H), 5.79-5.43 (m, 2H), 4.80-4.67 (m, 1H), 4.02 (d, J = 4.8 Hz, 1H), 3.81 (d, J = 4.8 Hz, 1H), 3.57 (d, J = 13.7 Hz, 1H), 3.29-2.75 | 466 (M + H)$^+$ 464 (M − H)$^−$ |

TABLE 8-continued

| Example | $^1$H-NMR (400 MHz, CDCl$_3$)δ | ESI/MS (m/z) |
|---|---|---|
|  | (m, 2H), 2.49-2.29 (m, 1H), 2.02-1.96 (m, 1H), 1.44 (brs, 1H), 1.07 (brs, 2H). |  |
| 89 (chiral A) | 8.11-7.86 (m, 1H), 7.60-6.75 (m, 6H), 6.32-6.19 (m, 1H), 5.94-5.75 (m, 1H), 4.76-4.73 (m, 1H), 4.18-2.80 (m, 7H), 2.54-1.66 (m, 5H), 1.42-1.04 (m, 6H). | 515 (M + H)$^+$ 513 (M − H)$^-$ |

TABLE 9

| Example | $^1$H-NMR (400 MHz, CDCl$_3$)δ | ESI/MS (m/z) |
|---|---|---|
| 90 (chiral A) | 7.22-7.12 (m, 1H), 7.06-6.91 (m, 2H), 6.80-6.76 (m, 1H), 6.68 (s, 1H), 6.66-6.60 (m, 1H), 6.44-6.04 (m, 3H), 5.39-5.12 (m, 1H), 4.78-4.32 (m, 2H), 3.48-3.33 (m, 1H), 3.23-2.77 (m, 6H), 2.42-2.21 (m, 1H), 2.09-1.87 (m, 5H), 1.45 (d, J = 6.8 Hz, 2H), 1.41 (brs, 2H), 1.29 (d, J = 6.8 Hz, 1H), 1.06 (brs, 1H). | 517 (M + H)$^+$ 515 (M − H)$^-$ |
| 91 (chiral A) | 7.71 (d, J = 2.4 Hz, 1H), 7.47 (d, J = 1.9 Hz, 1H), 7.20-6.90 (m, 5H), 6.80 (d, J = 8.4 Hz, 1H), 6.65 (d, J = 7.7 Hz, 1H), 6.30-6.17 (m, 1H), 6.07-5.86 (m, 1H), 5.49-5.33 (m, 1H), 4.95 (d, J = 13.7 Hz, 1H), 4.59-4.49 (m, 1H), 3.83-3.61 (m, 1H), 3.18-3.02 (m, 2H), 2.87-2.63 (m, 1H), 2.59-2.46 (m, 3H), 2.41-2.30 (m, 3H), 2.19-2.04 (m, 1H), 1.72-1.37 (m, 3H). | 478 (M + H)$^+$ |
| 92 (chiral A) | 7.30-6.92 (m, 4H), 6.81-6.44 (m, 2H), 6.37-5.89 (m, 3H), 5.72-5.53 (m, 1H), 5.12-4.84 (m, 1H), 4.16-3.90 (m, 2H), 3.88-3.61 (m, 1H), 3.40-2.95 (m, 6H), 2.79-2.34 (m, 4H), 2.21-1.85 (m, 5H). | 453 (M + H)$^+$ |
| 93 (chiral A) | 7.21-6.91 (m, 3H), 6.79-6.46 (m, 3H), 6.36-6.19 (m, 1H), 6.10-5.94 (m, 1H), 5.13-4.86 (m, 1H), 4.22-4.04 (m, 1H), 3.91-3.54 (m, 3H), 3.35-2.91 (m, 6H), 2.81-2.54 (m, 1H), 2.50-2.32 (m, 3H), 2.17-1.83 (m, 5H), 1.30-1.18 (m, 3H). | 454 (M + H)$^+$ |
| 94 (racemate) | 7.32-6.13 (m, 7H), 5.93 (brs, 1H), 5.52 (brs, 1H), 5.17-4.88 (m, 1H), 3.91-2.98 (m, 6H), 2.84-1.96 (m, 8H), 1.63-0.76 (m, 4H). | 410 (M + H)$^+$ |
| 95 (racemate) | 7.18-6.97 (m, 4H), 6.69-6.64 (m, 1H), 6.58-6.53 (m, 1H), 6.24 (s, 1H), 5.96 (brs, 2H), 5.50 (brs, 1H), 5.01-4.96 (m, 1H), 4.04 (s, 2H), 3.81-3.68 (m, 2H), 3.37-3.08 (m, 4H), 2.79-2.57 (m, 2H), 2.42 (s, 3H), 2.36-2.27 (m, 1H), 2.12-2.05 (m, 2H), 1.60-1.53 (m, 1H), 1.08 (d, J = 6.5 Hz, 3H). | 467 (M + H)$^+$ 465 (M − H)$^-$ |
| 96 (chiral A) | 7.81-7.70 (m, 1H), 7.62-7.44 (m, 1H), 7.27-6.75 (m, 5H), 6.60-6.58 (m, 1H), 6.32-6.19 (m, 1H), 6.05-5.81 (m, 1H), 4.82-4.57 (m, 1H), 4.17-2.98 (m, 7H), 2.52-2.28 (m, 6H), 2.20-0.83 (m, 10H). | 475 (M + H)$^+$ 473 (M − H)$^-$ |
| 97 (racemate) | 8.07-7.32 (m, 3H), 7.23-6.49 (m, 6H), 6.33-5.37 (m, 4H), 4.96-4.71 (m, 1H), 4.20-3.28 (m, 4H), 2.86-2.29 (m, 7H), 1.40-0.40 (m, 6H). | 474 (M + H)$^+$ 472 (M − H)$^-$ |
| 98 (racemate) | 7.16 (d, J = 7.3 Hz, 1H), 7.06-6.92 (m, 2H), 6.89-6.79 (m, 1H), 6.69 (d, J = 8.5 Hz, 1H), 6.38-6.36 (m, 1H), 6.13-6.04 (m, 1H), 5.77-5.69 (m, 1H), 4.95-4.68 (m, 1H), 4.19-3.94 (m, 1H), 3.77-3.70 (m, 1H), 3.63-3.59 (m, 1H), 3.47-3.30 (m, 1H), 3.17-3.14 (m, 4H), 2.85-2.80 (m, 1H), 2.67-2.62 (m, 1H), 2.48-2.36 (m, 1H), 2.04-1.83 (m, 5H), 1.26-1.21 (m, 4H), 1.10-0.98 (m, 2H). | 470 (M + H)$^+$ |
| 99 (racemate) | 7.15 (d, J = 7.3 Hz, 1H), 7.06-6.92 (m, 2H), 6.90-6.79 (m, 1H), 6.71 (d, J = 8.6 Hz, 1H), 6.55-6.48 (m, 1H), 6.38-6.35 (m, 1H), 6.13-5.94 (m, 2H), 5.49-5.35 (m, 2H), 4.96-4.68 (m, 1H), 4.03 (d, J = 5.6 Hz, 2H), 3.49-3.30 (m, 2H), 3.17-3.15 (m, 4H), 2.85-2.78 (m, 1H), 2.56-2.39 (m, 2H), 2.07-1.93 (m, 5H), 1.07-0.97 (m, 3H). | 469 (M + H)$^+$ |
| 100 (racemate) | 7.15 (d, J = 7.3 Hz, 1H), 7.08-7.01 (m, 2H), 6.88 (d, J = 7.3 Hz, 1H), 6.75 (d, J = 8.5 Hz, 1H), 6.56 (t, J = 7.3 Hz, 1H), 6.38 (d, J = 2.2 Hz, 1H), 6.11 (dd, J = 8.5, 2.2 Hz, 1H), 4.79 (dd, J = 13.6, 3.2 Hz, 1H), 4.22-4.16 (m, 1H), 3.82-3.62 (m, 3H), 3.18-3.15 (m, 4H), 3.06 (d, J = 14.9 Hz, 1H), 2.94-2.70 (m, 2H), 2.31 (brs, 1H), 1.97-1.93 (m, 4H), 1.25 (d, J = 6.6 Hz, 3H), 0.96 (d, J = 6.8 Hz, 3H). | 488 (M + H)$^+$ 486 (M − H)$^-$ |
| 101 (racemate) | 7.16-7.12 (m, 2H), 7.09-7.01 (m, 2H), 6.88 (d, J = 8.1 Hz, 1H), 6.76 (d, J = 8.6 Hz, 1H), 6.37 (d, J = 2.3 Hz, 1H), 6.11 (dd, J = 8.6, 2.3 Hz, 1H), 5.93 (brs, 1H), 5.48 (brs, 1H), 4.79 (dd, J = 13.3, 3.0 Hz, 1H), 4.06 (d, J = 5.2 Hz, 2H), 3.74 (dd, J = 38.8, 15.0 Hz, 1H), 3.32-3.05 (m, 5H), 2.93-2.72 (m, 2H), 1.97-1.93 (m, 4H), 0.98 (d, J = 6.7 Hz, 3H). | 487 (M + H)$^+$ 485 (M − H)$^-$ |

Pharmacological Test
(1) Preparation of Human V2 Receptor Expression Cell

A DNA fragment containing a human V2 receptor code region was inserted into an expression vector of a vertebrate cell. The expression vector was genetically introduced into an animal cell to have the human V2 receptor express in the surface of the cell. Since the expression vector could express a neo gene which functions as a G418 resistance marker, it was cultured in a G418-containing medium, thereby selectively obtaining a human V2 receptor stable expression cell.

(2) cAMP Production Test in V2 Receptor Expression Cell

The human V2 receptor expression cell, which was prepared in the above described method, was recovered and resuspended into an incubation buffer (F-12 medium, 20 mM HEPES), and 5 μl of the cell was then divided into a 384-well plate with a density of 15,000 cells/well. 5 μl of a compound solution or an 8-AVP ((Arg$^8$)-vasopressin) solution, which was diluted with an assay buffer (F-12 medium, 20 mM HEPES, 1 mM IBMX), (total 10 μl/well) was added to each well (final concentration: 15,000 cells/well, 500 μM IBMX, 1% dimethyl sulfoxide). After incubation at room temperature for 30 minutes, a cAMP production amount was measured using a commercially available HTRF cAMP kit (Cisbio Inc.) according to the described protocol. Excel Fit was used in order to find EC$_{50}$ and Emax values of the test compound. The Emax value of the test compound was calculated assuming the maximum reaction by 8-AVP to be 100% and an value showing a 50% reaction from a concentration-reaction curve of the test compound was defined to be the $EC_{50}$ value, and the obtained $EC_{50}$ and Emax values were shown in Table 10.

As a result, all compounds of examples examined in this time were found to have a V2 receptor agonist activity.

TABLE 10

| Example | $EC_{50}$ (nM) | $E_{max}$ (%) |
|---|---|---|
| 31 (racemate) | 7.9 | 102 |
| 32 (racemate) | 9.1 | 104 |
| 33 (racemate) | 20 | 96 |
| 34 (racemate) | 9.8 | 98 |
| 35 (chiral A) | 1.4 | 102 |
| 38 (chiral A) | 0.060 | 101 |
| 42 (racemate) | 0.80 | 103 |
| 43 (racemate) | 0.10 | 102 |
| 45 (chiral A) | 0.34 | 102 |
| 49 (racemate) | 0.50 | 102 |
| 50 (racemate) | 0.90 | 100 |
| 51 (racemate) | 6.0 | 73 |
| 52 (racemate) | 3.9 | 85 |
| 54 (chiral A) | 0.28 | 102 |
| 55 (racemate) | 0.20 | 101 |
| 56 (racemate) | 0.10 | 102 |
| 57 (racemate) | 0.20 | 102 |
| 67 (chiral A) | 2.8 | 102 |
| 68 (chiral A) | 0.74 | 102 |
| 69 (racemate) | 0.53 | 101 |
| 72 (chiral A) | 2.1 | 101 |
| 73 (racemate) | 1.9 | 100 |
| 76 (chiral A) | 0.99 | 102 |
| 79 (racemate) | 0.90 | 100 |
| 80 (racemate) | 2.8 | 101 |
| 81 (racemate) | 6.6 | 100 |
| 82 (racemate) | 1.1 | 101 |
| 83 (racemate) | 3.4 | 100 |
| 84 (racemate) | 2.5 | 100 |
| 85 (racemate) | 15 | 94 |
| 86 (racemate) | 17 | 88 |
| 87 (racemate) | 9.5 | 97 |
| 88 (racemate) | 8.1 | 93 |
| 89 (chiral A) | 1.4 | 102 |
| 90 (chiral A) | 0.39 | 101 |
| 94 (racemate) | 0.41 | 101 |
| 95 (racemate) | 0.99 | 102 |
| 97 (racemate) | 0.56 | 102 |
| 98 (racemate) | 1.0 | 101 |
| 99 (racemate) | 0.40 | 102 |
| 100 (racemate) | 3.0 | 100 |
| 101 (racemate) | 1.1 | 102 |

(3) Rat PK Test

A male Sprague-Dawely (Crj: CD(SD)IGS: CHARLES RIVER LABORATORIES JAPAN, INC.) rat was used between 7 to 8 weeks of age as an experimental animal. A rat fasted for one night was used. A test compound was dissolved into DMSO, thereto were added PEG and physical saline to adjust a concentration to be 0.5 mg/mL (20/20/60, v/v/v), and the solution was administered to the caudal vein in a use amount of 0.5 mg/kg. A blood sample was taken with a syringe treated with heparin from the jugular vein with time from 6 to 8 hours after administration and the taken blood was centrifuged to obtain plasma. A plasma drug concentration was measured using LC/MS/MS. For the sample for the LC/MS/MS measurement, a supernatant obtained by adding an internal standard substance and acetonitrile to the plasma and then deproteinization was used. A PK parameter was analyzed by a non-compartment model. A clearance ($CL_p$) was calculated by dividing an administration amount by $AUC_{0-\infty}$. A distribution volume ($Vd_{ss}$) was calculated by multiplying $CL_p$ by a mean retention time (MRT). The obtained CLp and Vdss were shown in Table 11.

As a result, all compounds of examples examined in this time had preferable plasma clearance and volume of distribution and were found to be excellent in view of the kinetics.

TABLE 11

| Example | AUC (ng · h/mL) | $CL_p$ (mL/h/kg) | $Vd_{ss}$ (mL/kg) |
|---|---|---|---|
| 65 (chiral A) | 641 | 780 | 726 |
| 66 (chiral A) | 368 | 1360 | 27 |
| 67 (chiral A) | 360 | 1390 | 1220 |
| 71 (racemate) | 522 | 958 | 666 |
| 72 (chiral A) | 430 | 1160 | 960 |
| 74 (racemate) | 467 | 1070 | 896 |
| 89 (chiral A) | 371 | 1350 | 1230 |
| 90 (chiral A) | 613 | 816 | 1080 |
| 91 (chiral A) | 449 | 1110 | 1750 |
| 93 (chiral A) | 366 | 1370 | 1330 |
| comparative compound 1 | 176 | 2870 | 4720 |

Note that the comparative compound 1 indicates the compound of Example 4 described in WO No. 2006/104008 (compound: N-(2-hydroxyethyl)-(R)-1-(2-chloro-4-pyrazol-1-ylbenzoyl)-3-methyl-1,2,3,5-tetrahydro-benzo[e]-1,4-diazepine-4-carboxamide).

(4) Test of Inhibition of Cytochrome P450 (3A4) Enzyme

Using a 96 well plate, midazolam (2.5 μM) as a substrate, a test compound (0.21 to 50 μM), human liver microsome with a protein concentration of 0.1 mg protein/mL were added to a 0.1 M phosphoric acid buffer solution (pH=7.4), which contains 1.55 mM $NADP^+$, 3.3 mM glucose-6-phosphate, 3.3 mM $MgCl_2$ and 0.4 Units/ml of glucose-6-phosphate dehydrogenase to form a reaction solution having a total amount of 500 μl. The reaction solution was incubated at 37° C. for 10 minutes and 4-hold amount of cold acetonitrile was added thereto to terminate the reaction. Then, the reaction solution was centrifuged (5000 g×10 minutes×4° C.), and the supernatant was collected to measure a production amount of a metabolized product by LC/MS/MS. An inhibition ratio of each concentration was calculated for a value which does not contain the test compound, and the upper and lower concentration points of the test compound which inhibits 50% of a production amount of a metabolized product were determined. $IC_{50}$ was found by use of these two test compound concentrations and the inhibition ratio. The obtained $IC_{50}$ value was shown in Table 12.

(5) Test of Inhibition of Cytochrome P450 (2C9) Enzyme

Using a 96 well plate, sulfaphenazole (10 μM) as a substrate, a test compound (0.21 to 50 μM), human liver microsome with a protein concentration of 0.1 mg protein/mL were added to a 0.1 M phosphoric acid buffer solution (pH=7.4), which contains 1.55 mM $NADP^+$, 3.3 mM glucose-6-phosphate, 3.3 mM $MgCl_2$ and 0.4 Units/ml of glucose-6-phosphate dehydrogenase to form a reaction solution having a total amount of 5001. The reaction solution was incubated at 37° C. for 10 minutes and 4-hold amount of cold acetonitrile was added thereto to terminate the reaction. Then, the reaction solution was centrifuged (5000 g×10 minutes×4° C.), and the supernatant was collected to measure a production amount of a metabolized product by LC/MS/MS. An inhibition ratio of each concentration was calculated for a value which does not contain the test compound, and the upper and lower concentration points of the test compound which inhibits 50% of a production amount of a metabolized product were determined. $IC_{50}$ was found by use of these two test compound concentrations and the inhibition ratio. The obtained $IC_{50}$ value was shown in Table 12.

As a result, it was found that all compounds of examples examined in this time showed low inhibition actions for drug metabolizing enzymes CYP3A4 and CYP2C9.

TABLE 12

| Example | IC$_{50}$ (μM) | |
|---|---|---|
| | CYP3A4 | CYP2C9 |
| 65 (chiral A) | >50 | 44.2 |
| 67 (chiral A) | >50 | >50 |
| 72 (chiral A) | >50 | 46.8 |
| 89 (chiral A) | >50 | 40.2 |
| 93 (chiral A) | 46.0 | 46.1 |
| comparative compound 2 | 0.4 | 0.2 |

Note that the comparative compound 2 indicates the compound of Example 32 described in WO No. 97/22591 (compound: 2-[(5R)-1-(2-chloro-4-pyrrolidine-1-ylbenzoyl)-2,3,4,5-tetrahydrobenzoazepine-5-yl]-N-isopropylacetoamide).

INDUSTRIAL APPLICABILITY

The compound of the present invention has a V2 receptor agonistic action and is therefore useful as a preventive or therapeutic agent for central diabetes insipidus, nocturnal enuresis, nocturia, overactive bladder, hemophilia, or Von Willebrand disease.

The invention claimed is:

1. A compound represented by the formula (I):

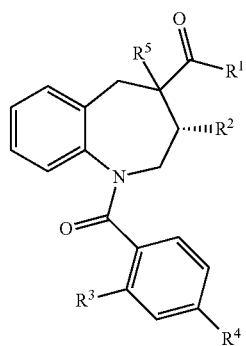

wherein R$^1$ is a hydroxyl group, a lower alkoxy group, or the formula described below:

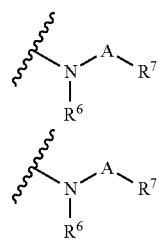

wherein A is absent or is a lower alkylene group which may be substituted with a lower alkyl group; R$^6$ is a hydrogen atom or a lower alkyl group; R$^7$ is a hydrogen atom, a hydroxyl group, an aromatic heterocyclic group which may be substituted with a lower alkyl group, a non-aromatic heterocyclic group which may be substituted with an oxo group, or a carbamoyl group which may be substituted with a lower alkyl group; R$^2$ is a hydrogen atom or a lower alkyl group; R$^3$ is a lower alkyl group which may be substituted with 1 to 3 fluorine atoms, or a halogen atom; R$^4$ is a lower alkoxy group which may be substituted with a halogen atom, a five-membered aromatic monocyclic heterocyclic group, or a five-membered non-aromatic monocyclic heterocyclic group provided that each of these heterocyclic groups contains at least one nitrogen atom and may be substituted with a lower alkyl group; and R$^5$ is a hydrogen atom, a lower alkyl group, or a halogen atom, or a pharmacologically acceptable salt thereof.

2. The compound according to claim 1, wherein R$^1$ is a hydroxyl group, a lower alkoxy group, or the formula described below:

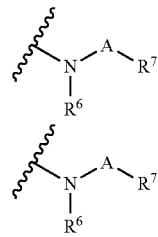

wherein A is absent or is a lower alkylene group which may be substituted with a lower alkyl group; R$^6$ is a hydrogen atom or a lower alkyl group; R$^7$ is a hydrogen atom, a hydroxyl group, an aromatic heterocyclic group which may be substituted with a lower alkyl group, a non-aromatic heterocyclic group which may be substituted with an oxo group, or a carbamoyl group which may be substituted with a lower alkyl group, provided that the case in which A is a lower alkylene group which may be substituted with a lower alkyl group and both R$^6$ and R$^7$ are hydrogen atoms, and the case in which A is absent, R$^6$ is a lower alkyl group, and R$^7$ is a hydrogen atom, are excluded.

3. The compound according to claim 2, wherein R$^1$ is the formula described below:

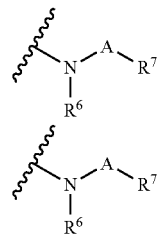

wherein A is absent or is a lower alkylene group which may be substituted with a lower alkyl group; R$^6$ is a hydrogen atom or a lower alkyl group; R$^7$ is a hydrogen atom, a hydroxyl group, an oxadiazole group which may be substituted with a lower alkyl group, a pyrrolidine group which may be substituted with an oxo group, or a carbamoyl group which may be substituted with 1 or 2 lower alkyl groups, provided that the case in which A is a lower alkylene group which may be substituted with a lower alkyl group and both R$^6$ and R$^7$ are hydrogen atoms, and the case in which A is absent, $R^6$ is a lower alkyl group, and $R^7$ is a hydrogen atom, are excluded.

4. The compound according to claim 3, wherein $R^1$ is the formula described below:

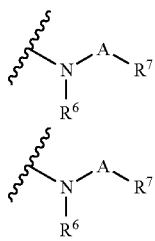

wherein A is a lower alkylene group which may be substituted with a lower alkyl group; $R^6$ is a hydrogen atom; $R^7$ is a hydroxyl group, an oxadiazole group which may be substituted with a lower alkyl group, or a carbamoyl group.

5. The compound according to claim 1, wherein $R^4$ is a lower alkoxy group which may be substituted with 1 to 3 fluorine atoms, a pyrrolidine group which may be substituted with 1 to 4 lower alkyl groups, a pyrazole group which may be substituted with 1 to 3 lower alkyl groups, or an oxazolyl group which may be substituted with 1 or 2 lower alkyl groups.

6. The compound according to claim 5, wherein $R^4$ is a group selected from the following group:

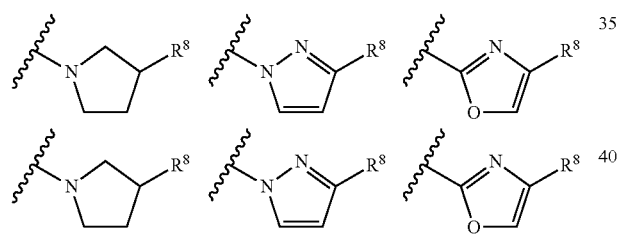

wherein $R^8$ is a hydrogen atom or a lower alkyl group.

7. The compound according to claim 6, wherein $R^4$ is a group selected from the following group:

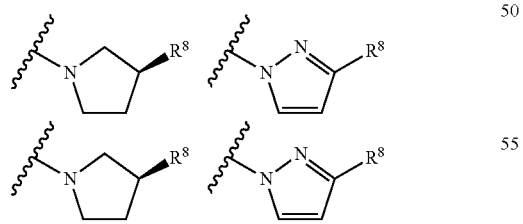

wherein $R^8$ is a lower alkyl group.

8. The compound according to claim 1, wherein $R^5$ is a methyl group or a fluorine atom.

9. The compound according to claim 1, wherein $R^3$ is a methyl group, a trifluoromethyl group, or a chlorine atom.

10. The compound according to claim 1, wherein $R^1$ is the formula described below:

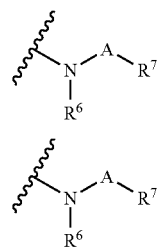

wherein A is a lower alkylene group which may be substituted with a lower alkyl group; $R^6$ is a hydrogen atom; $R^7$ is a hydroxyl group, an oxadiazole group which may be substituted with a lower alkyl group, or a carbamoyl group, $R^2$ is a hydrogen atom, $R^3$ is a methyl group, a trifluoromethyl group, or a chlorine atom, $R^4$ is a group selected from the following group

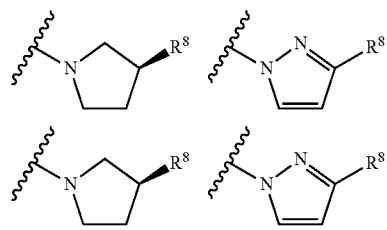

wherein $R^8$ is a lower alkyl group, and $R^5$ is a methyl group or a fluorine atom.

11. A compound represented by the formula (II):

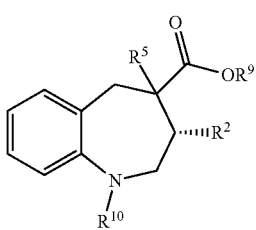

(II)

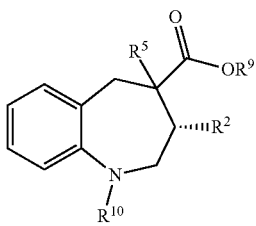

(II)

wherein $R^2$ is a hydrogen atom or a lower alkyl group; $R^5$ is a hydrogen atom, a methyl group, an ethyl group, or a halogen atom; $R^9$ is a hydrogen atom or a protecting group of a carboxy group; and $R^{10}$ is a hydrogen atom or a protecting group of an amino group, provided that the case in which both $R^2$ and $R^5$ are hydrogen atoms is excluded.

12. A pharmaceutical composition comprising the compound according to claim 1 as an active ingredient.

13. A compound represented by the formula (IV):

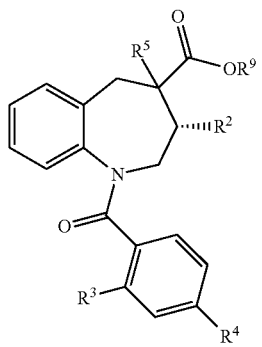

(IV)

wherein $R^2$ is a hydrogen atom or a lower alkyl group; $R^3$ is a lower alkyl group which may be substituted with 1 to 3 fluorine atoms, or a halogen atom; $R^4$ is a lower alkoxy group which may be substituted with a halogen atom, a five-membered aromatic monocyclic heterocyclic group, or a five-membered non-aromatic monocyclic heterocyclic group provided that each of these heterocyclic groups contains at least one nitrogen atom and may be substituted with a lower alkyl group; $R^5$ is a hydrogen atom, a lower alkyl group, or a halogen atom; and $R^9$ is a hydrogen atom or a protecting group of a carboxy group.

14. A method for treating disease selected from the group consisting of central diabetes insipidus, nocturnal enuresis, nocturia and overactive bladder disease, the method comprising administering the pharmaceutical composition according to claim 12.

* * * * *